United States Patent
Xu et al.

(10) Patent No.: US 11,964,948 B2
(45) Date of Patent: Apr. 23, 2024

(54) BIFUNCTIONAL CHELATORS AND CONJUGATES

(71) Applicant: ACTINIUM PHARMACEUTICALS, INC., New York, NY (US)

(72) Inventors: Le-Cun Xu, Yonkers, NY (US); Denis Beckford Vera, Valhalla, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 0 days.

(21) Appl. No.: 18/482,912

(22) Filed: Oct. 8, 2023

(65) Prior Publication Data

US 2024/0051928 A1 Feb. 15, 2024

Related U.S. Application Data

(63) Continuation of application No. PCT/US2023/068062, filed on Jun. 7, 2023.

(60) Provisional application No. 63/487,789, filed on Mar. 1, 2023, provisional application No. 63/408,970, filed on Sep. 22, 2022, provisional application No. 63/349,833, filed on Jun. 7, 2022.

(51) Int. Cl.
  *C07D 257/02* (2006.01)
  *C07K 16/28* (2006.01)

(52) U.S. Cl.
  CPC .......... *C07D 257/02* (2013.01); *C07K 16/283* (2013.01); *C07B 2200/05* (2013.01)

(58) Field of Classification Search
  CPC .. C07D 257/02; C07K 16/283; C07B 2200/05
  See application file for complete search history.

(56) References Cited

U.S. PATENT DOCUMENTS

| | | |
|---|---|---|
| 4,704,692 A | 11/1987 | Ladner |
| 4,946,778 A | 8/1990 | Ladner et al. |
| 6,120,768 A | 9/2000 | Griffiths et al. |
| 6,683,162 B2 | 1/2004 | Scheinberg et al. |
| 7,238,785 B2 | 7/2007 | Govindan et al. |
| 7,615,225 B2 | 11/2009 | Forsberg et al. |
| 7,816,388 B2 | 10/2010 | Carminati et al. |
| 7,829,673 B2 | 11/2010 | De Weers et al. |
| 8,088,896 B2 | 1/2012 | Tesar et al. |
| 8,153,765 B2 | 4/2012 | Park et al. |
| 8,518,405 B2 | 8/2013 | Mukherjee |
| 8,648,176 B2 | 2/2014 | Davis Orcutt et al. |
| 8,846,001 B2 | 9/2014 | Velikyan et al. |
| 9,090,698 B2 | 7/2015 | Mukherjee |
| 9,217,038 B2 | 12/2015 | Goletz et al. |
| 9,492,566 B2 | 11/2016 | Goldenberg et al. |
| 9,546,217 B2 | 1/2017 | Behrens et al. |
| 9,603,954 B2 | 3/2017 | Simon et al. |
| 9,606,123 B2 | 3/2017 | Slack-Davis et al. |
| 9,828,635 B2 | 11/2017 | Vincent et al. |
| 10,017,580 B2 | 7/2018 | Van Berkel et al. |
| 10,195,517 B2 | 2/2019 | Fechser |
| 10,314,910 B2 | 6/2019 | Nathan et al. |
| 10,420,851 B2 | 9/2019 | Dave et al. |
| 10,494,441 B2 | 12/2019 | Vincent et al. |
| 10,507,251 B2 | 12/2019 | Morinaka et al. |
| 10,517,966 B2 | 12/2019 | Morinaka et al. |
| 10,919,973 B2 | 2/2021 | Clausen et al. |
| 11,116,846 B2 | 9/2021 | Goldenberg et al. |
| 11,136,410 B2 | 10/2021 | Kufe et al. |
| 11,161,911 B2 | 11/2021 | White |
| 11,191,854 B2 | 12/2021 | Burak et al. |
| 11,225,496 B2 | 1/2022 | Berkman et al. |
| 11,344,638 B2 | 5/2022 | Taub |
| 2004/0258614 A1 | 12/2004 | Line et al. |
| 2009/0304710 A1 | 12/2009 | Park et al. |
| 2010/0204117 A1 | 8/2010 | Bevec |
| 2010/0297003 A1 | 11/2010 | De Santis et al. |
| 2011/0165074 A1 | 7/2011 | Gruell et al. |
| 2012/0213698 A1 | 8/2012 | Petersen et al. |
| 2012/0321619 A1 | 12/2012 | Linden et al. |
| 2013/0129636 A1 | 5/2013 | Kamaly et al. |
| 2014/0314670 A1 | 10/2014 | D'Addona et al. |
| 2015/0030618 A1 | 1/2015 | Lerchen et al. |
| 2016/0228587 A1 | 8/2016 | Eder et al. |
| 2016/0297890 A1 | 10/2016 | Agatsuma et al. |
| 2017/0158775 A1 | 6/2017 | Linden et al. |
| 2018/0031566 A1 | 2/2018 | Couto et al. |
| 2020/0061216 A1 | 2/2020 | Mukherjee |
| 2020/0069706 A1 | 3/2020 | Slusher et al. |
| 2020/0101160 A1 | 4/2020 | Nathan et al. |
| 2020/0306391 A1 | 10/2020 | Ray et al. |
| 2020/0339625 A1 | 10/2020 | Lin et al. |

(Continued)

FOREIGN PATENT DOCUMENTS

| CN | 101991867 A | 3/2011 |
|---|---|---|
| CN | 102406949 A | 4/2012 |

(Continued)

OTHER PUBLICATIONS

Bendre, Molecules, 2020, 25(17), 3854, 1-21. (Year: 2020).*
Uehara, Clinical Cancer research, 2018, 24(14), 3309-3316. (Year: 2018).*
Bendre et al., Evaluation of Met-Val-Lys as a renal brush border enzyme-cleavable linker to reduce kidney uptake of 68Ga-labeled DOTA-conjugated peptides and peptidomimetics, Molecules (2020), 25(17), 3854.
Suzuki et al., Copper-64-Labeled Antibody Fragments for Immuno-PET/Radioimmunotherapy with Low Renal Radioactivity Levels and Amplified Tumor-Kidney Ratios, ACS Omega (2021), 6(33), 21556-21562.
Uehara et al., A Gallium-67/68-Labeled Antibody Fragment for Immuno-SPECT/PET Shows Low Renal Radioactivity Without Loss of Tumor Uptake, Clinical Cancer Research (2018), 24(14), 3309-3316.

(Continued)

*Primary Examiner* — D Margaret M Seaman
(74) *Attorney, Agent, or Firm* — Dentons Cohen & Grigsby P.C.

(57) ABSTRACT

Provided are new bifunctional chelators for use in the manufacture of radiolabeled targeting agents for therapeutic or diagnostic use. Also provided are conjugates of the new bifunctional chelators with various cancer antigen targeting agents.

23 Claims, 15 Drawing Sheets

Specification includes a Sequence Listing.

(56) References Cited

U.S. PATENT DOCUMENTS

| | | | |
|---|---|---|---|
| 2021/0008232 A1 | 1/2021 | Chen et al. |
| 2021/0025006 A1 | 1/2021 | Xue et al. |
| 2021/0154338 A1 | 5/2021 | Bander |
| 2021/0161911 A1 | 6/2021 | Armour |
| 2021/0164985 A1 | 6/2021 | Couto et al. |
| 2021/0171653 A1 | 6/2021 | Risse et al. |
| 2021/0196844 A1 | 7/2021 | Bander |
| 2021/0238292 A1 | 8/2021 | Holland et al. |
| 2021/0238303 A1 | 8/2021 | Agatsuma et al. |
| 2021/0309711 A1 | 10/2021 | Li et al. |
| 2021/0369877 A1 | 12/2021 | Rosch et al. |
| 2021/0393809 A1 | 12/2021 | Haberkorn et al. |
| 2021/0395281 A1 | 12/2021 | Mahoney et al. |
| 2022/0024904 A1 | 1/2022 | Zeglis et al. |
| 2022/0062446 A1 | 3/2022 | Perrin et al. |
| 2022/0064312 A1 | 3/2022 | Yoshikawa et al. |
| 2022/0096653 A1 | 3/2022 | Akaiwa et al. |
| 2022/0220085 A1 | 7/2022 | Vlahov et al. |
| 2022/0403051 A1 | 12/2022 | Powell et al. |
| 2023/0047529 A1 | 2/2023 | Imura |
| 2023/0072421 A1 | 3/2023 | Bohnke et al. |
| 2023/0081720 A1 | 3/2023 | Burger et al. |
| 2023/0106083 A1 | 4/2023 | Murphy et al. |
| 2023/0119066 A1 | 4/2023 | Lan et al. |
| 2023/0190796 A1 | 6/2023 | Huss et al. |
| 2023/0201383 A1 | 6/2023 | Kjaer et al. |
| 2023/0250178 A1 | 8/2023 | Berndt et al. |

FOREIGN PATENT DOCUMENTS

| | | |
|---|---|---|
| CN | 102600489 A | 7/2012 |
| CN | 102626522 A | 8/2012 |
| CN | 102671217 A | 9/2012 |
| CN | 103529210 A | 1/2014 |
| CN | 104353087 A | 2/2015 |
| CN | 104815336 A | 8/2015 |
| CN | 106075484 A | 11/2016 |
| CN | 107096044 A | 8/2017 |
| CN | 108148012 A | 6/2018 |
| CN | 109134602 A | 1/2019 |
| CN | 110251695 A | 9/2019 |
| CN | 110743017 A | 2/2020 |
| CN | 111228521 A | 6/2020 |
| CN | 112237638 A | 1/2021 |
| CN | 112457401 A | 3/2021 |
| CN | 112546247 A | 3/2021 |
| CN | 112962125 A | 6/2021 |
| CN | 113368264 A | 9/2021 |
| CN | 113730613 A | 12/2021 |
| CN | 113730614 A | 12/2021 |
| CN | 114099719 A | 3/2022 |
| CN | 114404618 A | 4/2022 |
| DE | 102012019714 A1 | 4/2014 |
| EP | 4186926 A1 | 5/2023 |
| EP | 4227315 A1 | 8/2023 |
| JP | 2008222804 A | 9/2008 |
| JP | 2009269855 A | 11/2009 |
| JP | 2016020316 A | 2/2016 |
| KR | 20140014579 A | 2/2014 |
| KR | 101743727 B1 | 6/2017 |
| WO | 2005065724 A1 | 7/2005 |
| WO | 2007044756 A2 | 4/2007 |
| WO | 2013106824 A1 | 7/2013 |
| WO | 2021175147 * | 9/2021 |
| WO | 2022040607 A1 | 2/2022 |
| WO | 2022072292 A1 | 4/2022 |
| WO | 2022072293 A2 | 4/2022 |
| WO | 2022087156 A1 | 4/2022 |
| WO | 2022235676 A1 | 11/2022 |

OTHER PUBLICATIONS

Zhang et al., Improving the Theranostic Potential of Exendin 4 by Reducing the Renal Radioactivity through Brush Border Membrane Enzyme-Mediated Degradation, Bioconjugate Chemistry (2019), 30(6), 1745-1753.

International Search Report and Written Opinion dated Dec. 14, 2023 for corresponding International Application No. PCT/US2023/068062.

Kang et al., Recent developments in chemical conjugation strategies targeting native amino acids in proteins and their applications in antibody-drug conjugates, Chem. Sci., 12, (2021): 13613-13647.

Sneddon, et al., "Emerging chelators for nuclear imaging." Current Opinion in Chemical Biology, 63 (2021): 152-162.

Yang et al., "Harnessing a-Emitting Radionuclides for Therapy: Radiolabeling Method Review", J Nucl Med, (2022) 63:5-13.

* cited by examiner

BIFUNCTIONAL CHELATORS AND CONJUGATES

CROSS-REFERENCE TO RELATED APPLICATIONS

This application is a continuation of International Application No. PCT/US2023/068062 filed on Jun. 7, 2023, entitled BIFUNCTIONAL CHELATORS AND CONJUGATES, which claims priority to and the benefit of U.S. Provisional Patent Application No. 63/349,833 filed on Jun. 7, 2022, entitled BIFUNCTIONAL CHELATORS, U.S. Provisional Patent Application No. 63/408,970 filed on Sep. 22, 2022, entitled BIFUNCTIONAL CHELATORS, and U.S. Provisional Patent Application No. 63/487,789 filed on Mar. 1, 2023, entitled BIFUNCTIONAL CHELATORS AND CONJUGATES, which are expressly incorporated herein by reference in their entireties.

SEQUENCE LISTING

The present disclosure contains a Sequence Listing which has been submitted electronically in XML format and is hereby incorporated by reference in its entirety. Said XML copy, created on Jun. 7, 2023, is named PT23-045PCT_SL_ST26.xml and is 184,148 bytes in size.

FIELD OF THE INVENTION

The present disclosure relates to the field of bifunctional chelators and linkers.

BACKGROUND

Bifunctional chelators are compounds that include a metal (or metalloid) chelating moiety and a reactive group that can mediate conjugation to a target molecule such as a protein. Dodecane tetraacetic acid (DOTA), IUPAC name 2,2',2'',2'''-(1,4,7,10-Tetraazacyclododecane-1,4,7,10-tetrayl)tetraacetic acid, is a macrocyclic compound capable of chelating radiometals such as $^{90}Y$, $^{225}Ac$, and $^{177}Lu$. Bifunctional DOTA chelators known in the art include, for example, S-2-(4-Isothiocyanatobenzyl)-1,4,7,10-tetraazacyclododecane tetraacetic acid (also known as p-SCN-Bn-DOTA) and 1,4,7,10-Tetraazacyclododecane-1,4,7,10-tetraacetic acid mono-N-hydroxysuccinimide ester (also known as DOTA-NHS-ester).

BRIEF SUMMARY

The present disclosure provides novel bifunctional chelator compounds of formula (A), or a metal complex thereof:

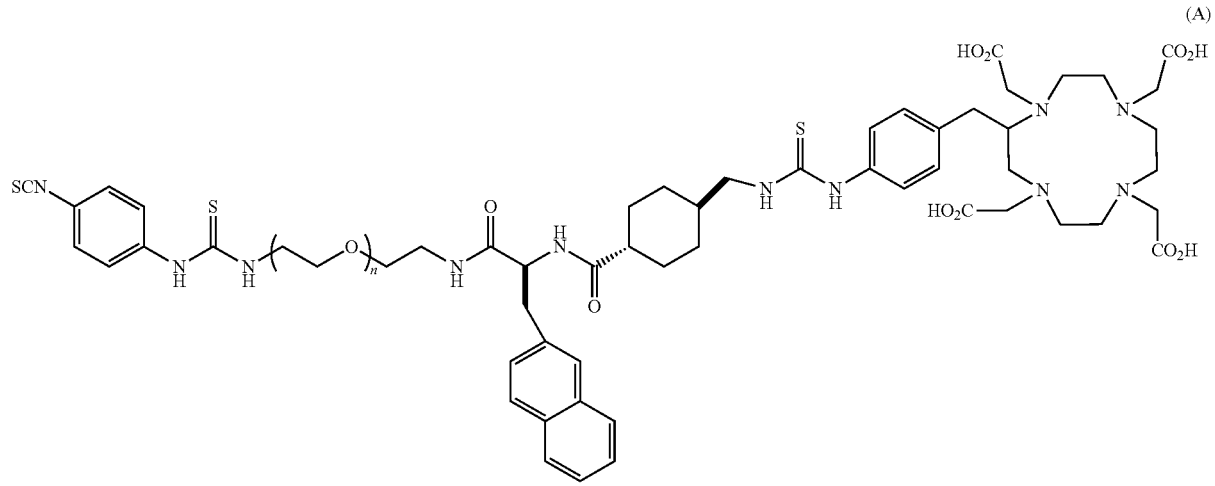

(A)

wherein n is 1 or an integer greater than 1, such as an integer from 1 to 1000 or any integer value therein or any subrange of integers therein, such as from 1 to 100 or 1 to 20. For example, n may be 1, 2, 3, 4, 5, 6, 7, 8, 9, or 10.

The present disclosure provides novel bifunctional chelator compounds of formula (B), or a metal complex thereof:

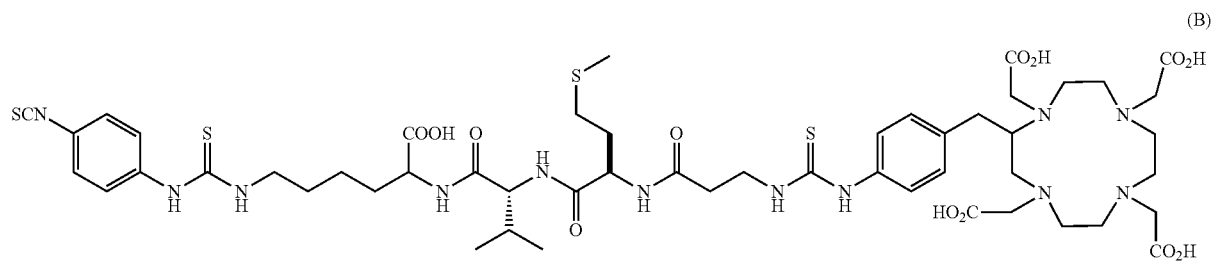

(B)

The present disclosure provides novel bifunctional chelator compounds having a formula including a metal chelator and at least one component selected from: a reactive group for conjugation of the bifunctional chelator to a target molecule such as a protein or a peptide, a benzyl group, at least one amino acid and/or amino acid derivative, a chelator moiety, a PEG spacer, a non-aromatic cyclic hydrocarbon, ethyleneamine, and thiourea, wherein when more than one component is included, the reactive group is a terminal component and any additional components may be in any order.

The present disclosure further provides novel bifunctional chelator compounds having a formula as shown in any one of FIGS. 3-17, i.e., compounds C-Q, or metal complexes thereof.

The present disclosure further provides a conjugated molecule formed by reacting one of the aforementioned bifunctional chelator compounds that includes a N-hydroxysuccinimide ester/NHS ester (abbreviated "NHS" herein) or thiocyanate (abbreviated "SCN" herein) reactive group and a molecule including one or more primary amine groups, including, but not limited to, a peptide, such as a synthetic peptide, or a protein, such as a recombinant protein.

The present disclosure provides a method for conjugating a chelator to a molecule including one or more primary amine groups, such as a protein or a peptide that includes the step of reacting the molecule with one of the aforementioned bifunctional chelator compounds that includes a NHS or SCN reactive group to form a chelator-conjugated molecule.

The present disclosure provides a conjugated molecule formed by reacting one of the aforementioned bifunctional chelator compounds that includes a phenyloxadiazolyl methylsulfone (abbreviated "PODS" herein) reactive group or derivative thereof and a molecule including one or more free thiol groups, including, but not limited to, a peptide, such as a synthetic peptide, or a protein, such as a recombinant protein.

Also provided by this disclosure is a method for conjugating a chelator to a molecule including one or more free thiol groups, such as a protein or a peptide, that includes the step of reacting the molecule with one of the aforementioned bifunctional chelator compounds that includes a PODS reactive group or derivative thereof to form a chelator-conjugated molecule. The method may include a prior or concurrent step of forming a free thiol group for reaction with a PODS reactive group by reducing a disulfide bond present in a molecule or connecting different molecules.

The molecules that are conjugated with the bifunctional chelator compounds may include antibodies such as monoclonal antibodies, or antibody chains, such as immunoglobulin heavy chains and/or immunoglobulin light chains, and/or the variable regions of such heavy or light chains. The molecules that are conjugated with the bifunctional chelator compounds may include antigen binding fragments of monoclonal antibodies such as Fab fragments or $Fab_2$ fragments, or corresponding scFv molecules.

Additional features, advantages, and aspects of the present disclosure may be set forth or apparent from consideration of the following detailed description, drawings if any, and claims. Moreover, it is to be understood that both the foregoing summary of the present disclosure and the following detailed description are exemplary and intended to provide further explanation without limiting the scope of the invention as claimed.

DETAILED DESCRIPTION

The present disclosure provides bifunctional chelator compounds. The bifunctional chelator compounds of the present disclosure may be used for the manufacture of radiolabeled targeting agents for therapeutic and/or diagnostic use. The present disclosure further provides methods of conjugation of the bifunctional chelator compounds to primary amines or thiols, such as amines or thiols of a peptide or protein, and compositions including the resulting conjugates, and methods for radiolabeling the resulting conjugates.

Figure 1:
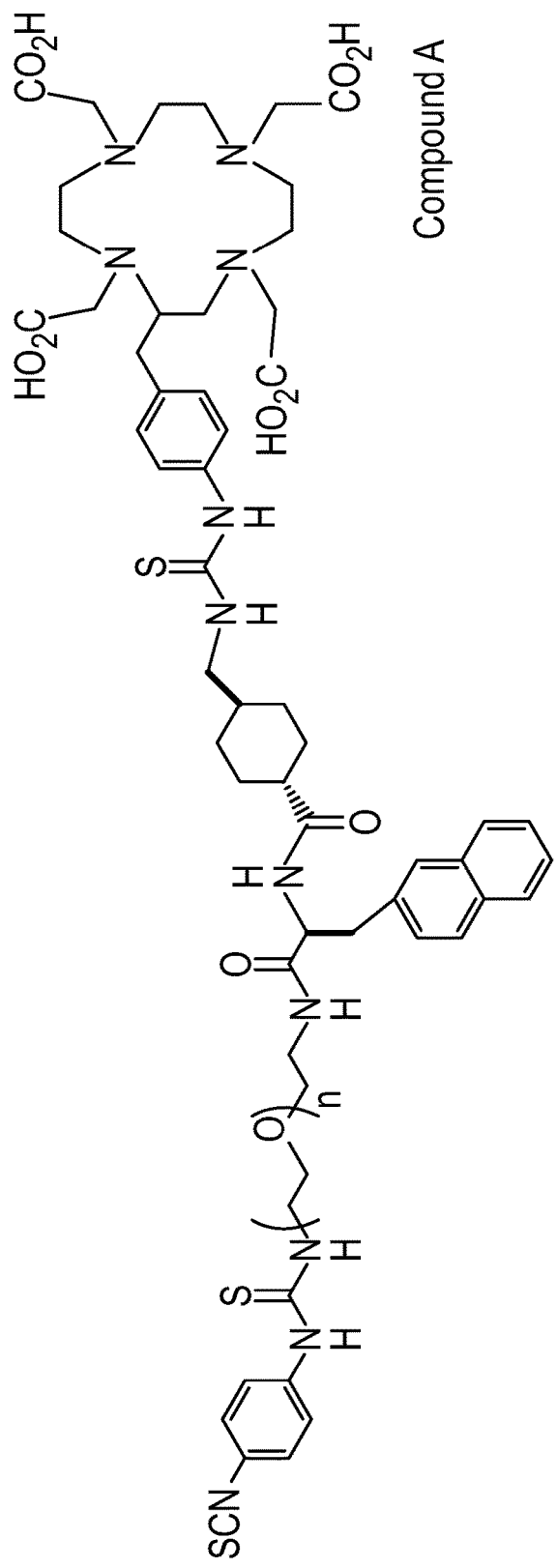
FIG. 1 shows a bifunctional chelator compound of Formula A.

The bifunctional chelator compounds of the present disclosure may include a compound having the formula (A) (FIG. 1), or a metal complex thereof:

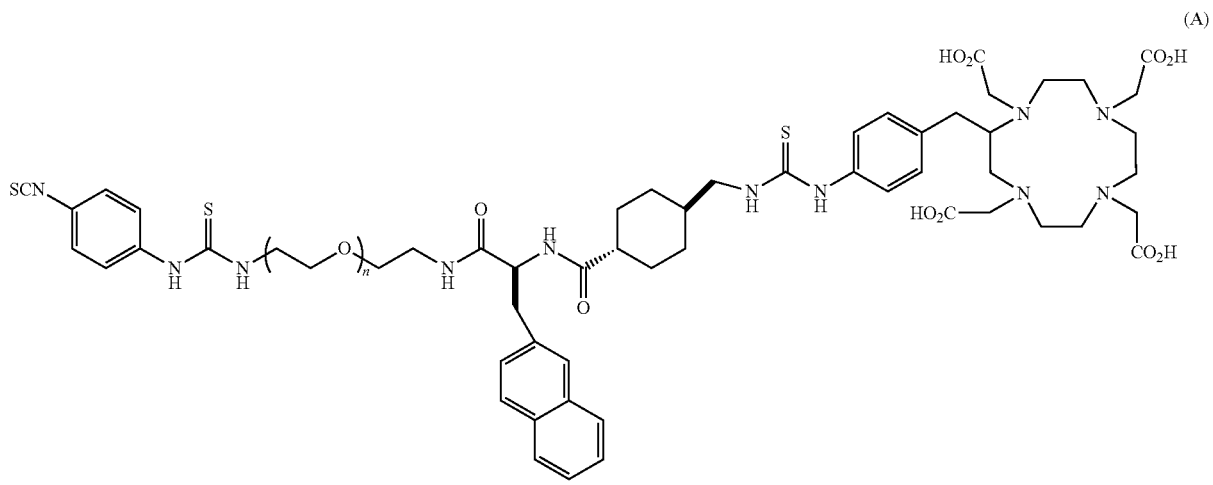

(A)

having a PEG$_n$ spacer, wherein n is 1 or an integer greater than 1, such as from 1 to 1000 or any integer value therein or any subrange of integers therein, such as from 1 to 100 or 1 to 20. The PEG$_n$ spacer may in addition or alternatively be defined by molecular weight or average molecular weight. For example, the average molecular weight of the PEG element may be 0.1 KD to 1 KD, 1 KD to 5 KD, 5 KD to 15 KD, 15 KD to 25 KD, 25 KD to 35 KD, or 35 KD to 50 KD.

Figure 2:
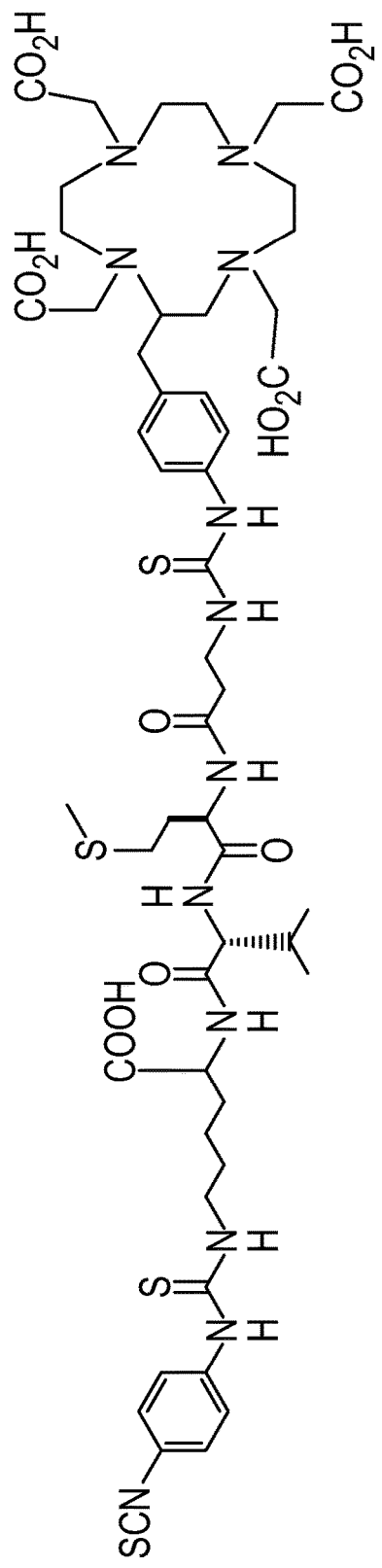
FIG. 2 shows a bifunctional chelator compound of Formula B.

The bifunctional chelator compounds of the present disclosure may include a compound having the formula (B) (FIG. 2), or a metal complex thereof:

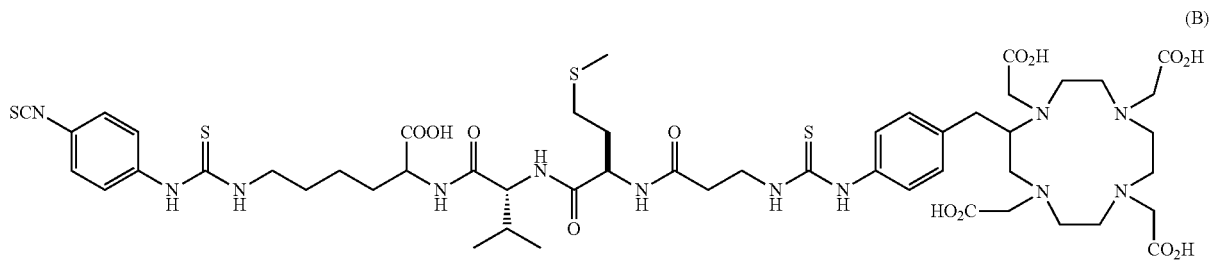

(B)

Figure 3:
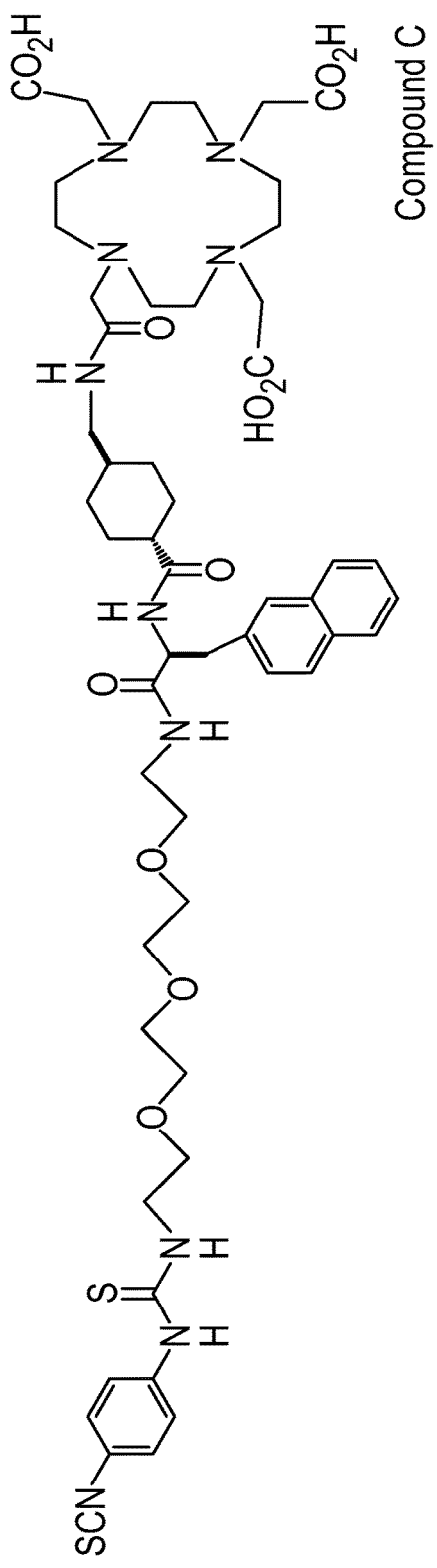
FIG. 3 shows a bifunctional chelator compound of Formula C.

The bifunctional chelator compounds of the present disclosure may include a compound having the formula (C) (FIG. 3), or a metal complex thereof:

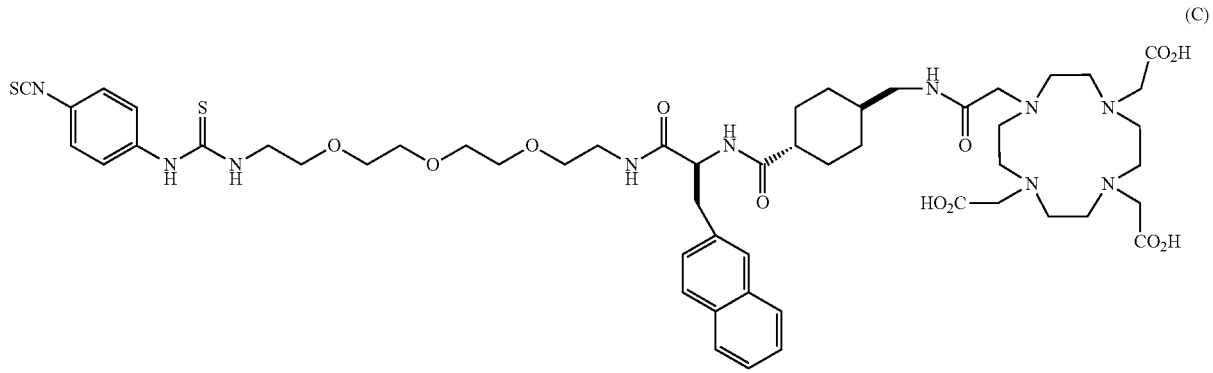

(C)

Figure 4:
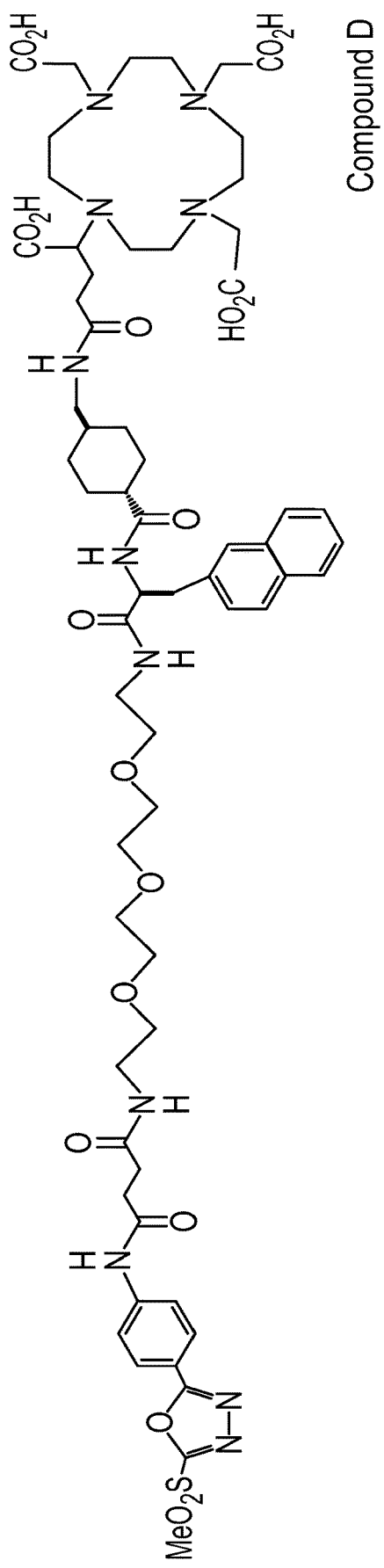
FIG. 4 shows a bifunctional chelator compound of Formula D.

The bifunctional chelator compounds of the present disclosure may include a compound having the formula (D) (FIG. 4), or a metal complex thereof:

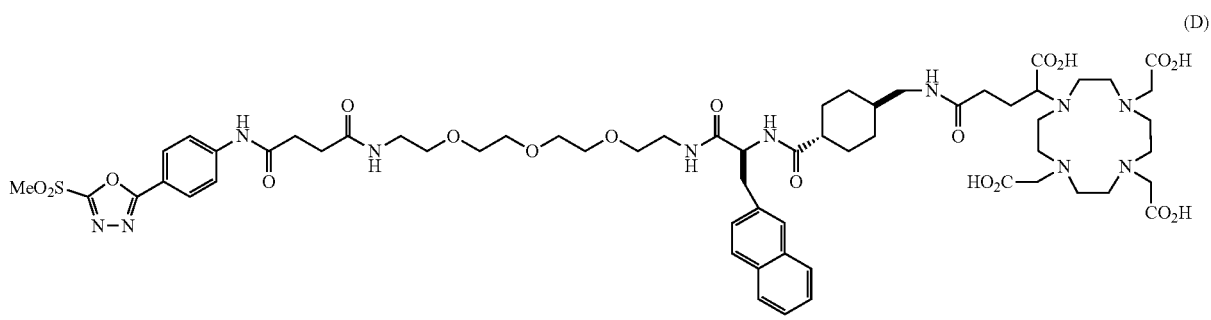 [SMILES: CS(=O)(=O)c1nnc(-c2ccc(NC(=O)CCC(=O)NCCOCCOCCOCCNC(=O)[C@H](Cc3ccc4ccccc4c3)NC(=O)[C@H]3CC[C@H](CNC(=O)CCC(C(=O)O)N4CCN(CC(=O)O)CCN(CC(=O)O)CCN(CC(=O)O)CC4)CC3)cc2)o1]

(D)

Figure 5:
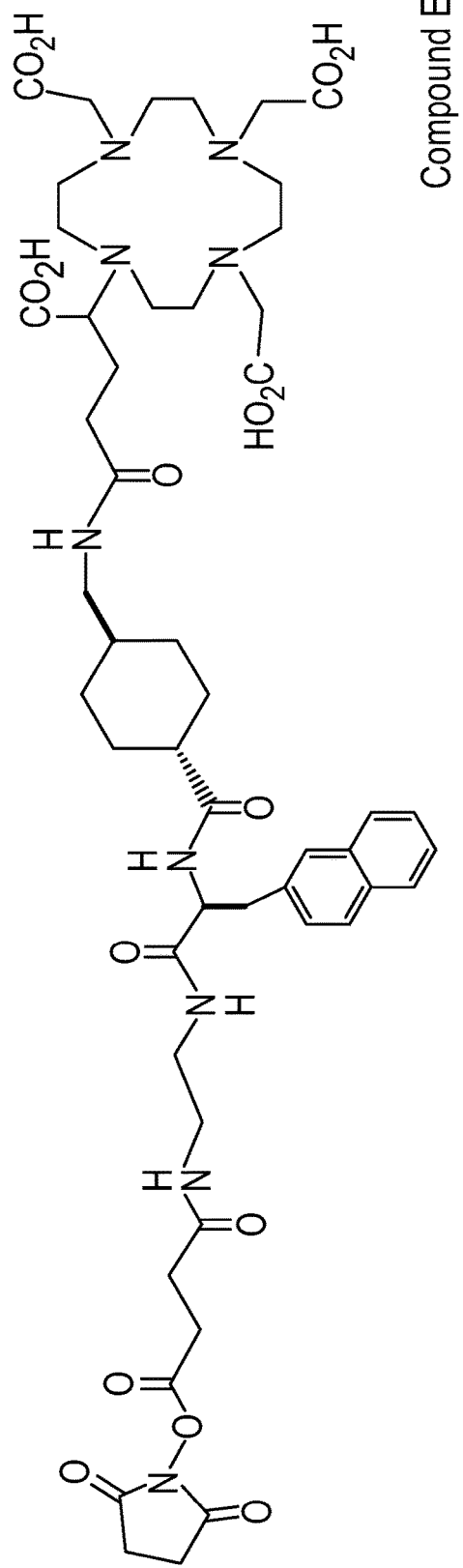
FIG. 5 shows a bifunctional chelator compound of Formula E.

The bifunctional chelator compounds of the present disclosure may include a compound having the formula (E) (FIG. 5), or a metal complex thereof:

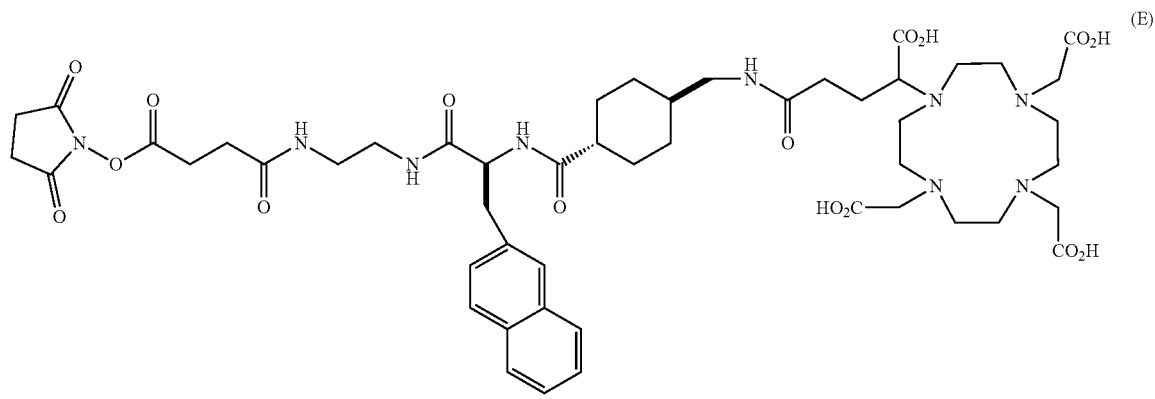 [SMILES: O=C(O)CN1CCN(CC(=O)O)CCN(C(CCC(=O)NC[C@H]2CC[C@H](C(=O)N[C@@H](Cc3ccc4ccccc4c3)C(=O)NCCNC(=O)CCC(=O)ON3C(=O)CCC3=O)CC2)C(=O)O)CCN(CC(=O)O)CC1]

(E)

Figure 6:
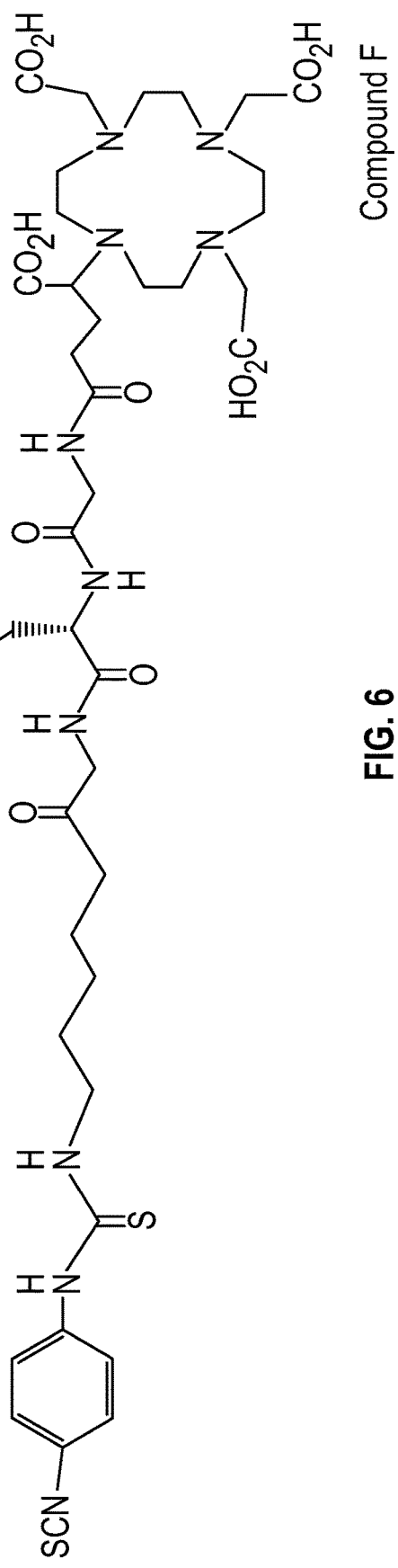
FIG. 6 shows a bifunctional chelator compound of Formula F.

The bifunctional chelator compounds of the present disclosure may include a compound having the formula (F) (FIG. 6), or a metal complex thereof:

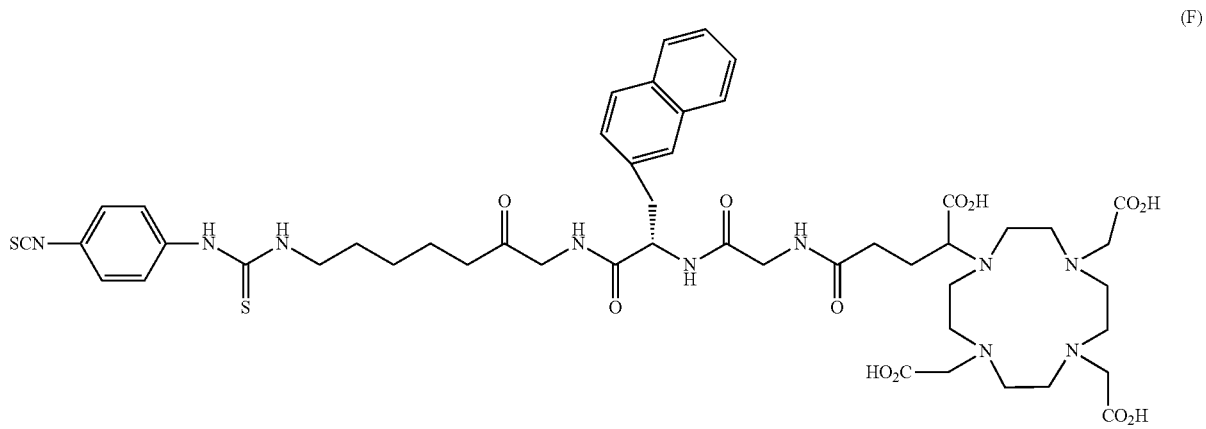

(F)

Figure 7:
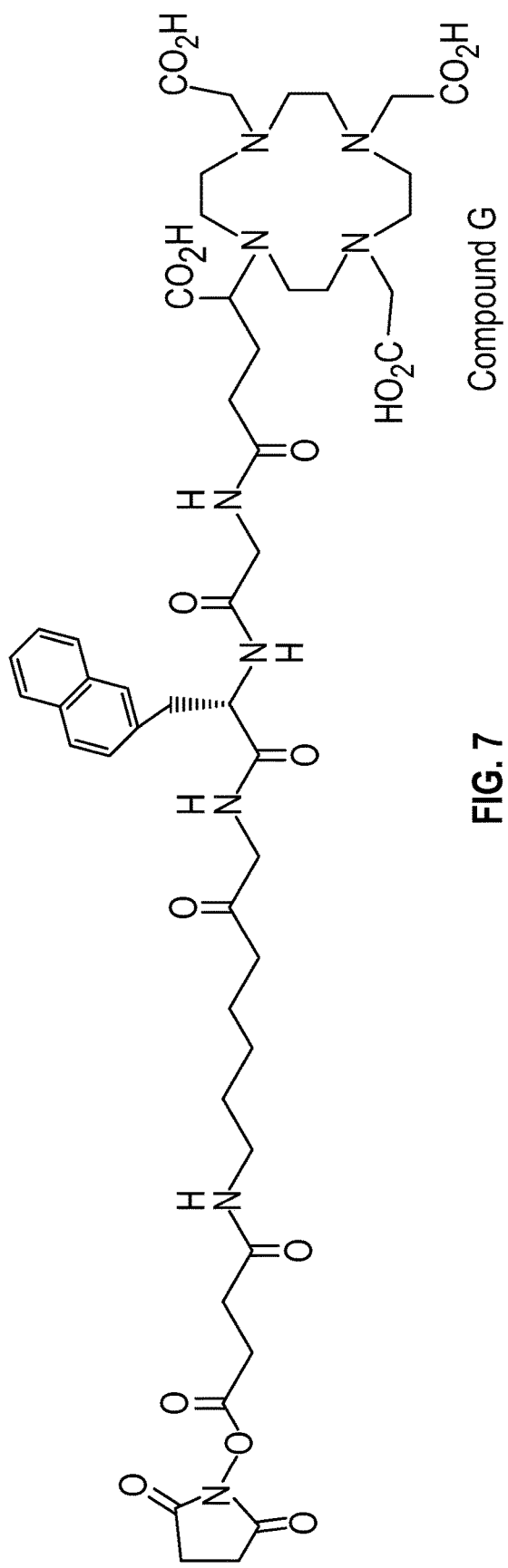
FIG. 7 shows a bifunctional chelator compound of Formula G.

The bifunctional chelator compounds of the present disclosure may include a compound having the formula (G) (FIG. 7), or a metal complex thereof:

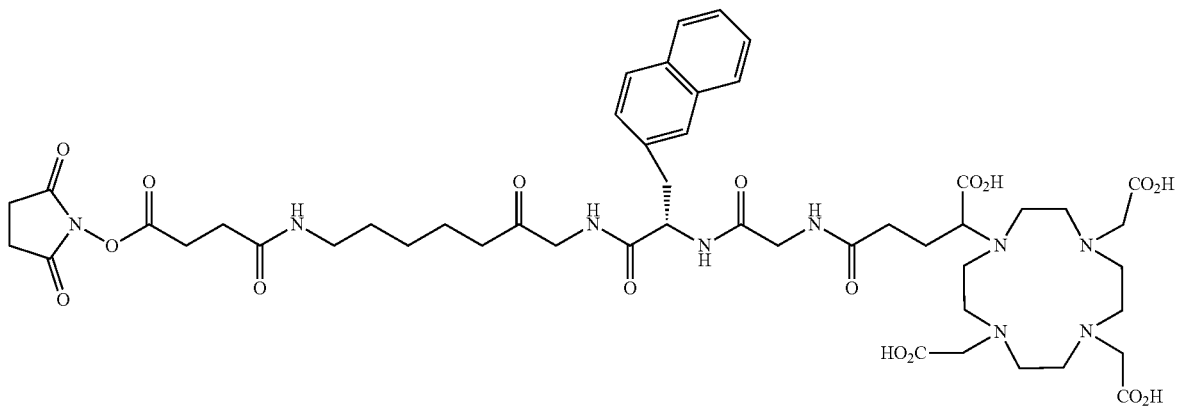

(G)

Figure 8:
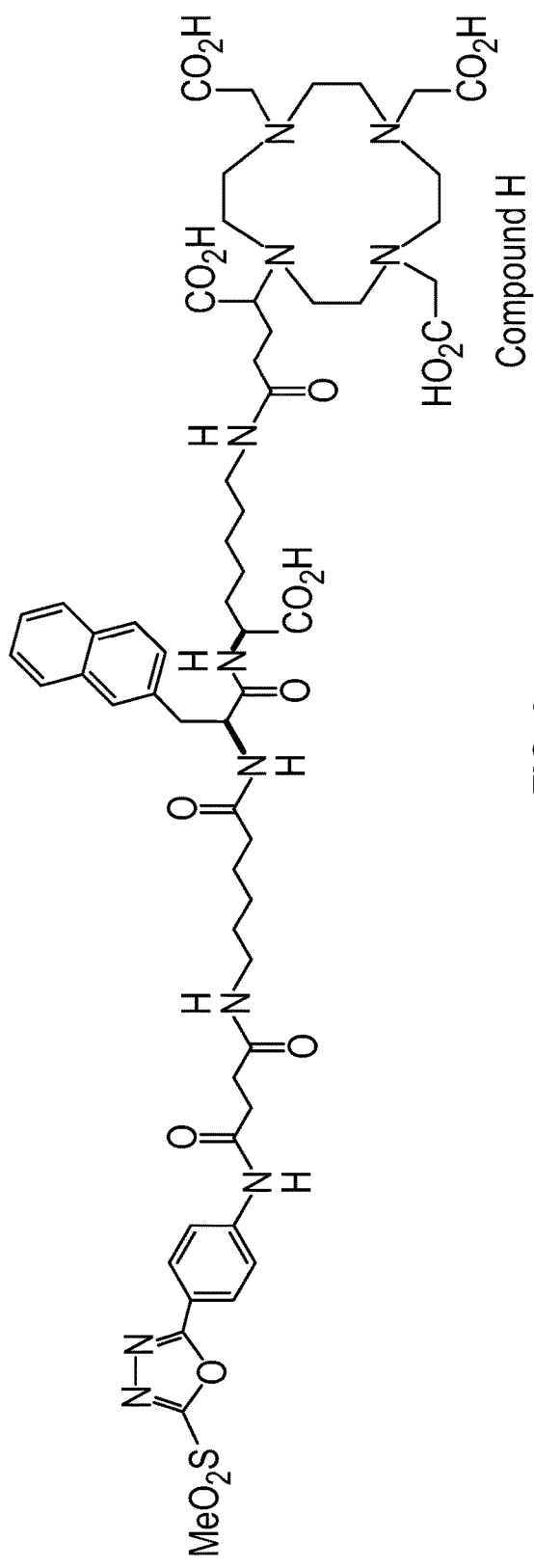
FIG. 8 shows a bifunctional chelator compound of Formula H.

The bifunctional chelator compounds of the present disclosure may include a compound having the formula (H) (FIG. 8), or a metal complex thereof:

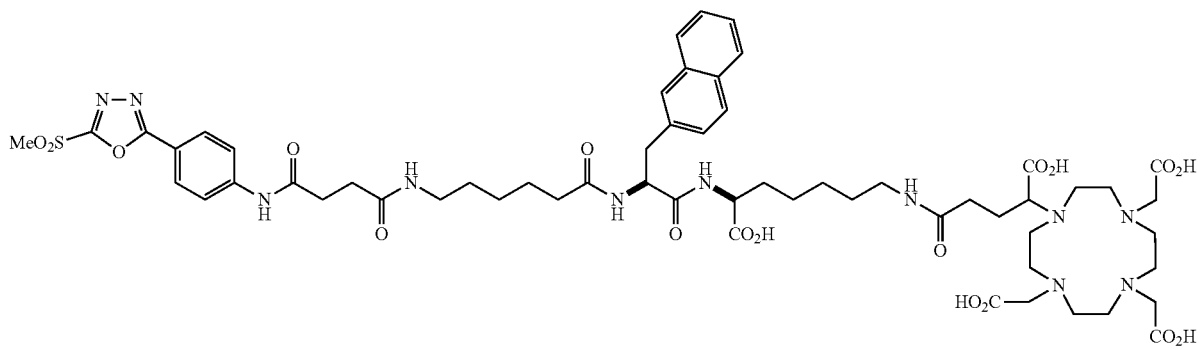

(H)

Figure 9:
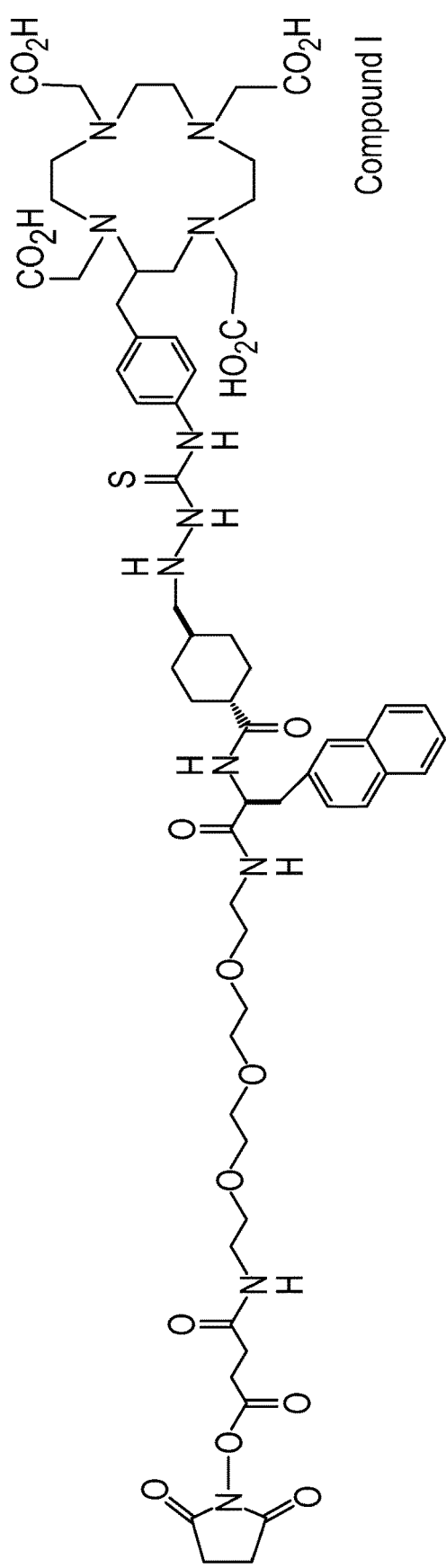
FIG. 9 shows a bifunctional chelator compound of Formula I.

The bifunctional chelator compounds of the present disclosure may include a compound having the formula (I) (FIG. 9), or a metal complex thereof:

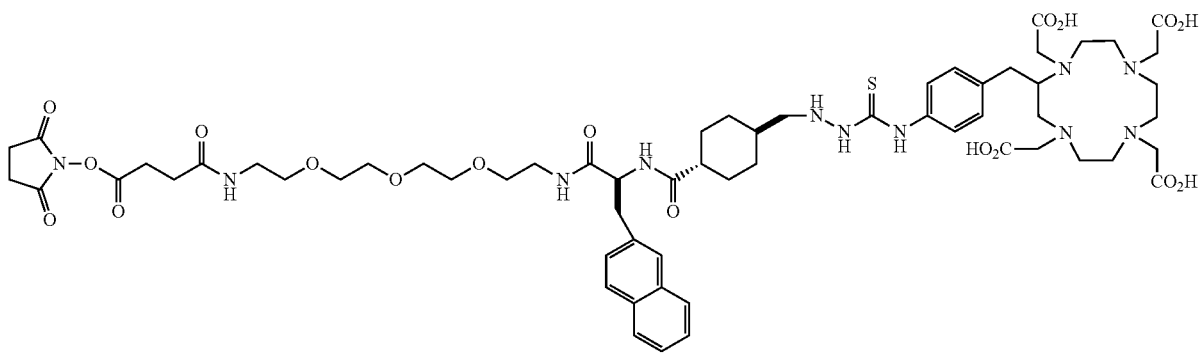

(I)

Figure 10:
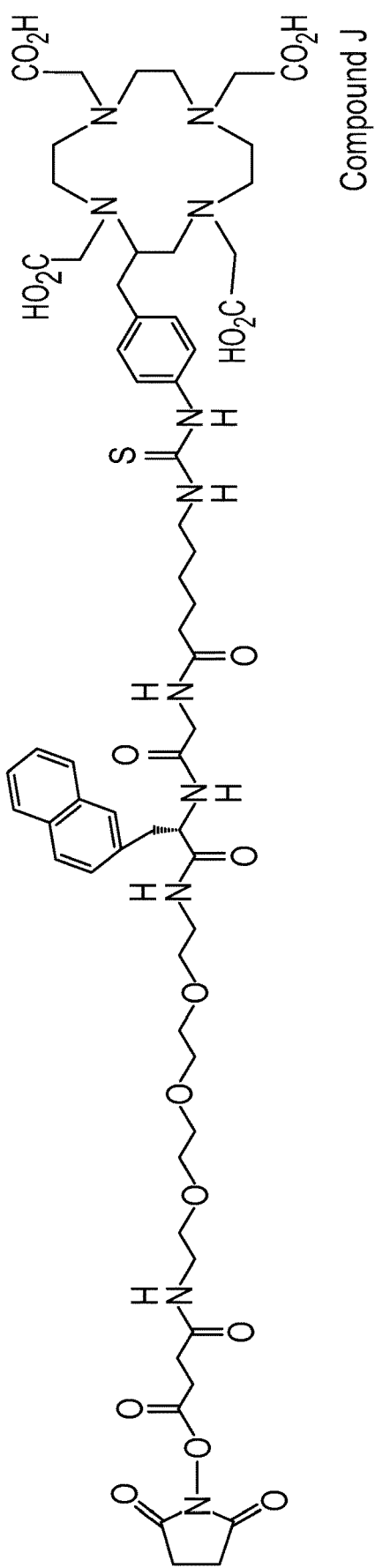
FIG. 10 shows a bifunctional chelator compound of Formula J.

The bifunctional chelator compounds of the present disclosure may include a compound having the formula (J) (FIG. 10), or a metal complex thereof:

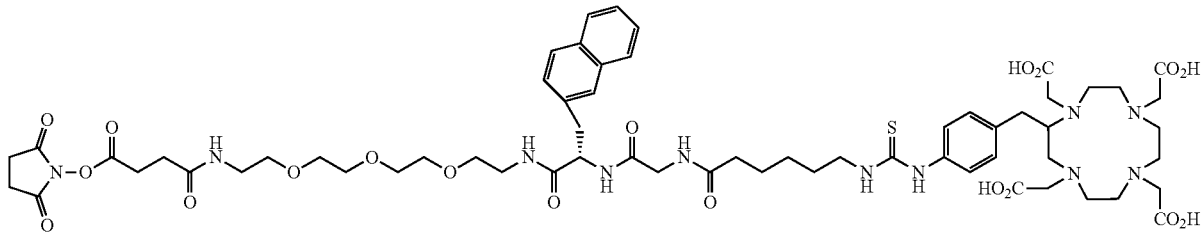

(J)

Figure 11:
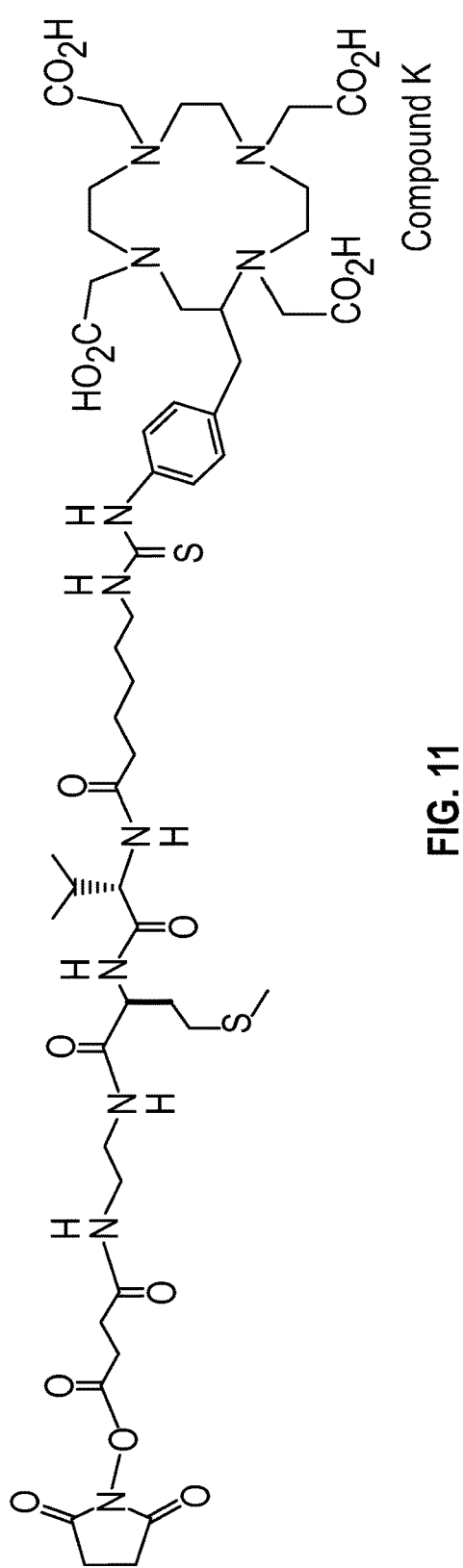
FIG. 11 shows a bifunctional chelator compound of Formula K.

The bifunctional chelator compounds of the present disclosure may include a compound having the formula (K) (FIG. 11), or a metal complex thereof:

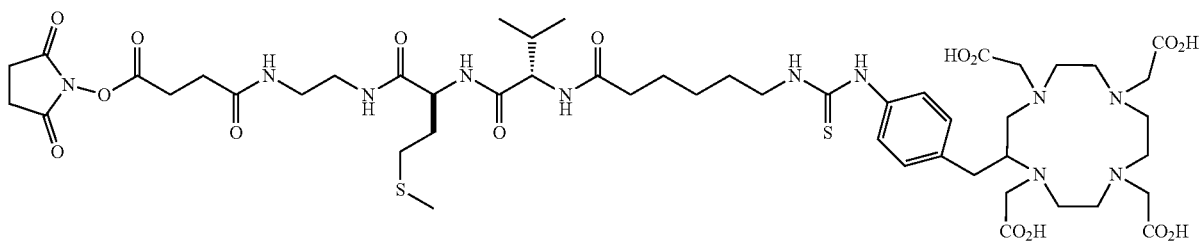

(K)

Figure 12:
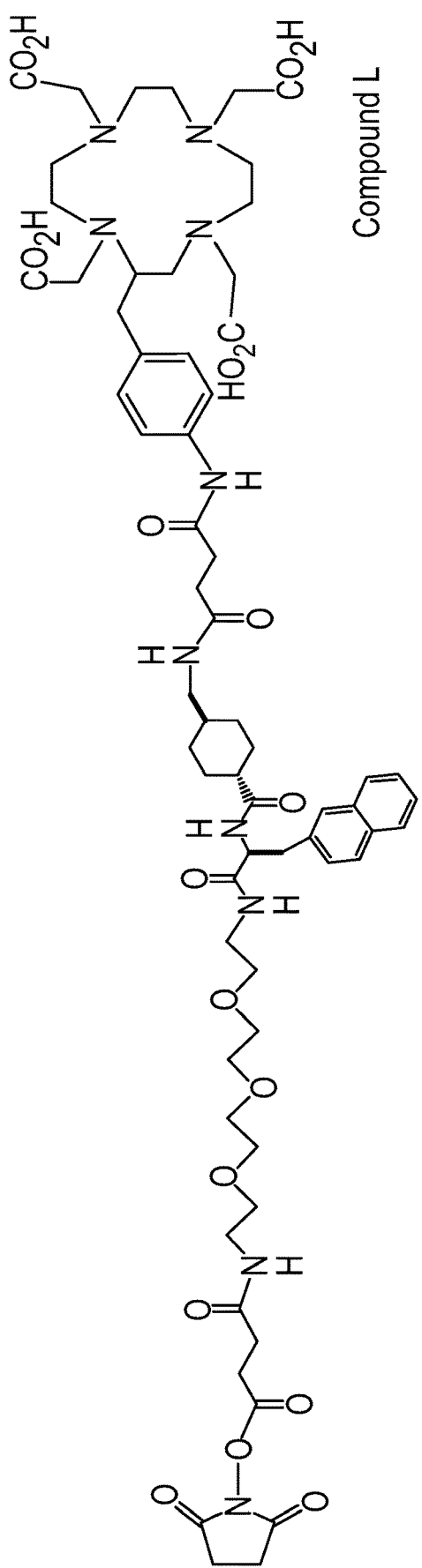
FIG. 12 shows a bifunctional chelator compound of Formula L.

The bifunctional chelator compounds of the present disclosure may include a compound having the formula (L) (FIG. 12), or a metal complex thereof:

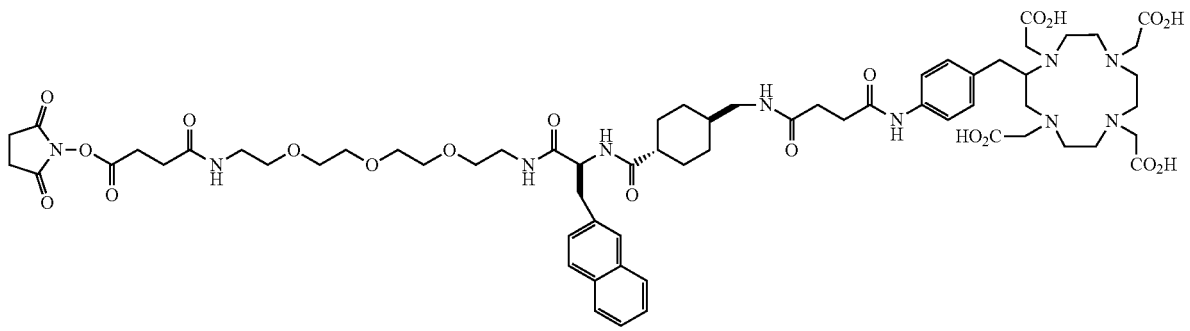

(L)

Figure 13:
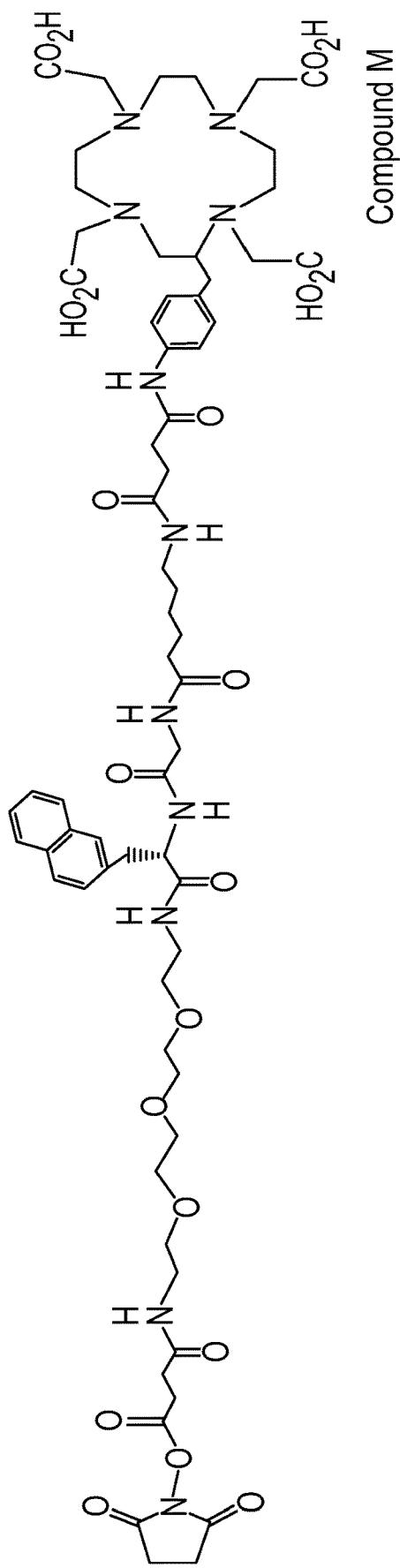
FIG. 13 shows a bifunctional chelator compound of Formula M.

The bifunctional chelator compounds of the present disclosure may include a compound having the formula (M) (FIG. 13), or a metal complex thereof:

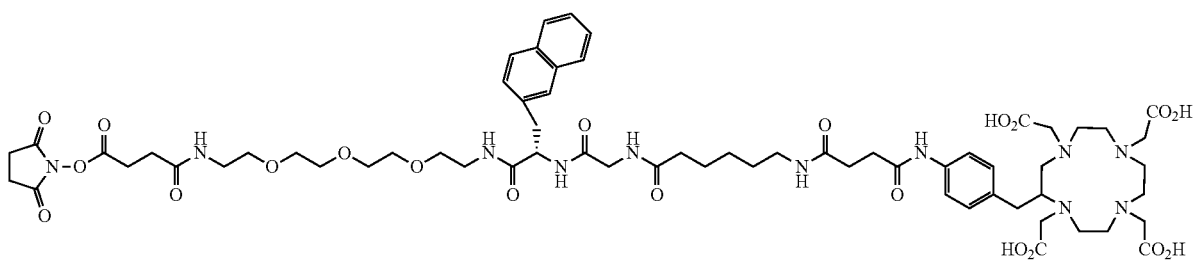

(M)

Figure 14:
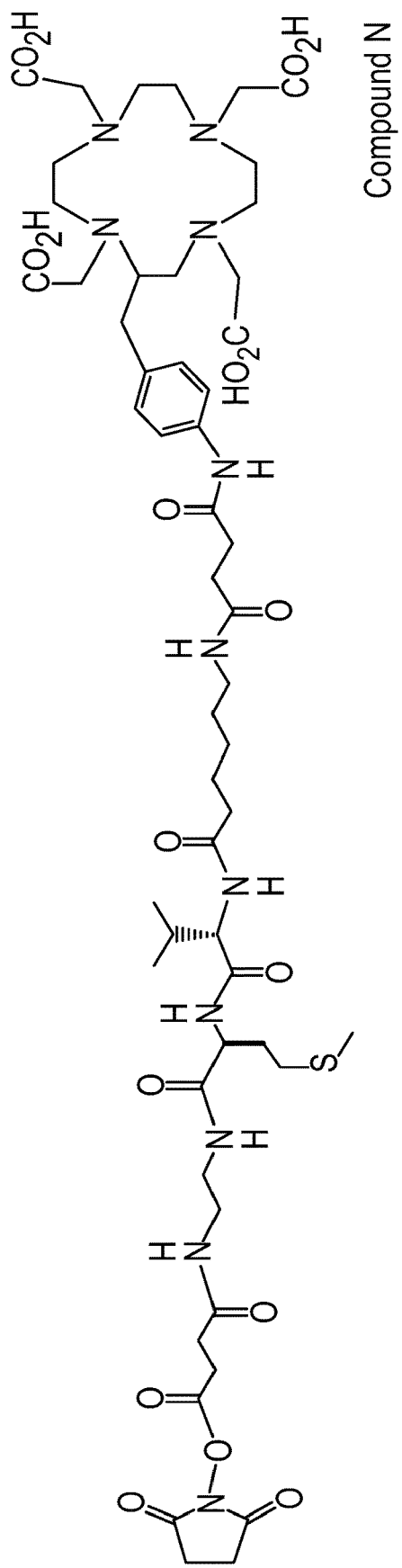
FIG. 14 shows a bifunctional chelator compound of Formula N.

The bifunctional chelator compounds of the present disclosure may include a compound having the formula (N) (FIG. 14), or a metal complex thereof:

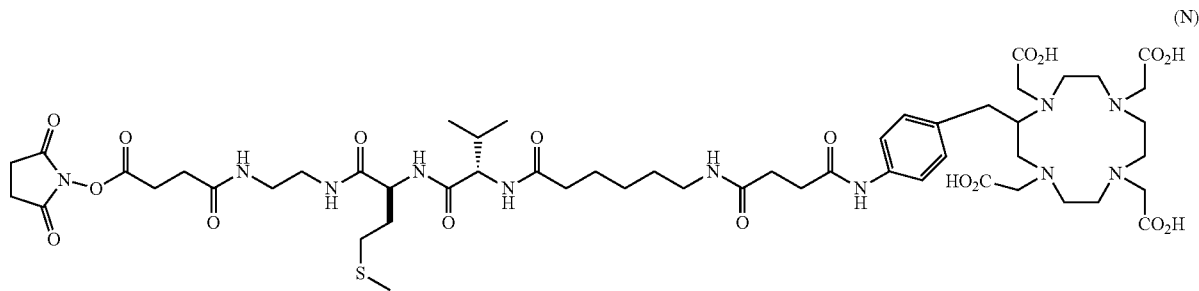 [SMILES: CSCC[C@H](NC(=O)[C@@H](NC(=O)CCCCCNC(=O)CCC(=O)Nc1ccc(CC2CN(CC(=O)O)CCN(CC(=O)O)CCN(CC(=O)O)CCN2CC(=O)O)cc1)C(C)C)C(=O)NCCNC(=O)CCC(=O)ON1C(=O)CCC1=O]

(N)

Figure 15:
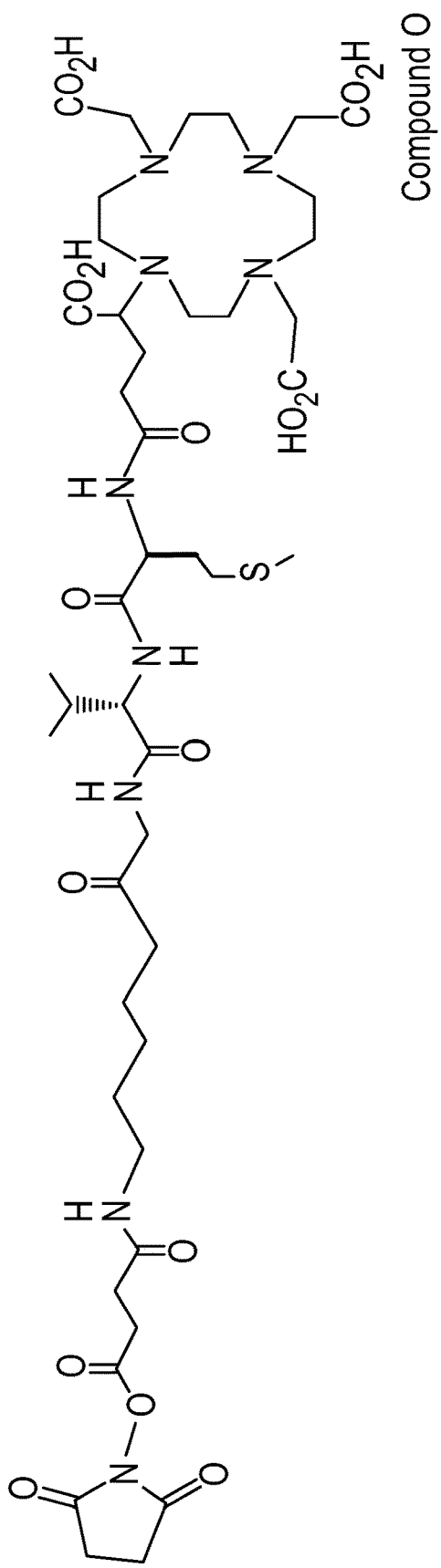
FIG. 15 shows a bifunctional chelator compound of Formula O.

The bifunctional chelator compounds of the present disclosure may include a compound having the formula (O) (FIG. 15), or a metal complex thereof:

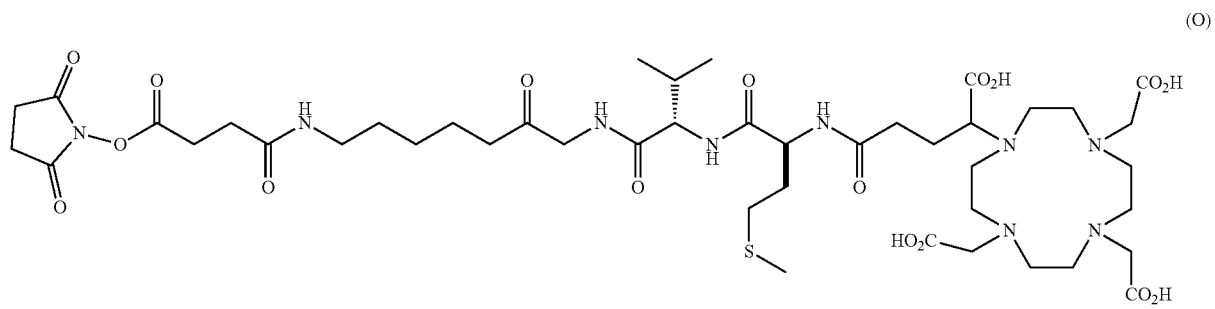 [SMILES: CSCC[C@H](NC(=O)CCC(C(=O)O)N1CCN(CC(=O)O)CCN(CC(=O)O)CCN(CC(=O)O)CC1)C(=O)N[C@H](C(=O)NCC(=O)CCCCCNC(=O)CCC(=O)ON1C(=O)CCC1=O)C(C)C]

(O)

Figure 16:
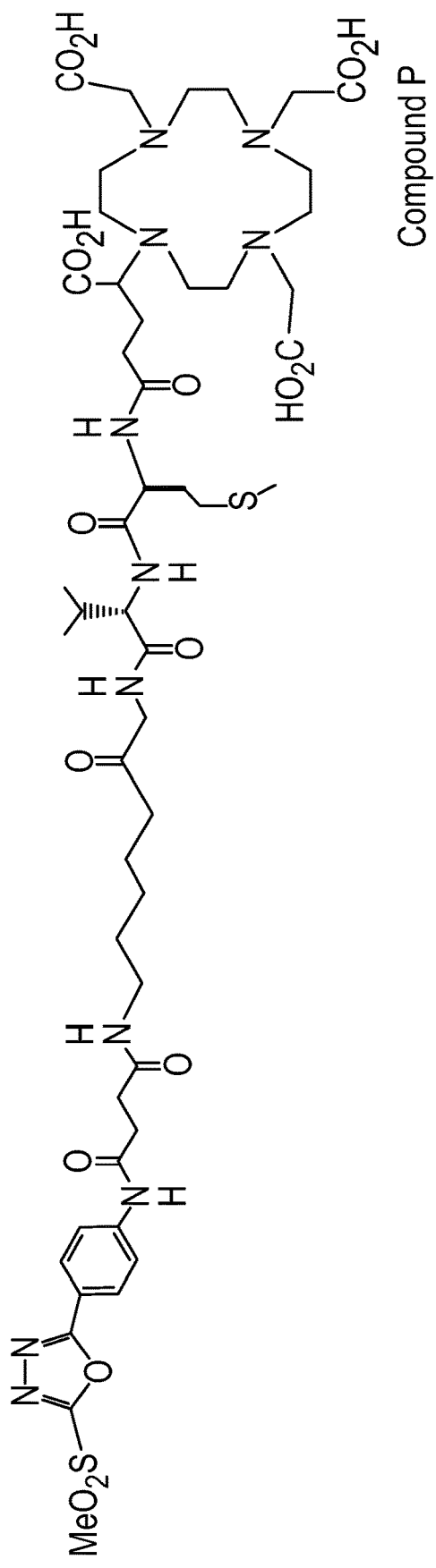
FIG. 16 shows a bifunctional chelator compound of Formula P.

The bifunctional chelator compounds of the present disclosure may include a compound having the formula (P) (FIG. 16), or a metal complex thereof:

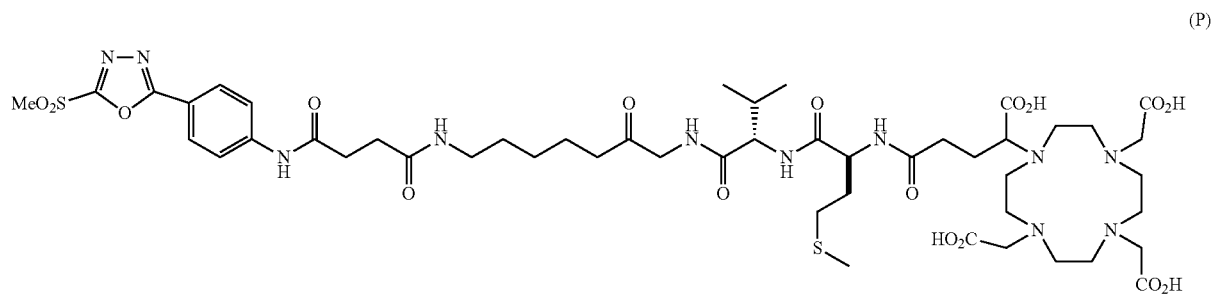 [SMILES: CSCC[C@H](NC(=O)CCC(C(=O)O)N1CCN(CC(=O)O)CCN(CC(=O)O)CCN(CC(=O)O)CC1)C(=O)N[C@H](C(=O)NCC(=O)CCCCCNC(=O)CCC(=O)Nc1ccc(-c2nnc(S(C)(=O)=O)o2)cc1)C(C)C]

(P)

Figure 17:
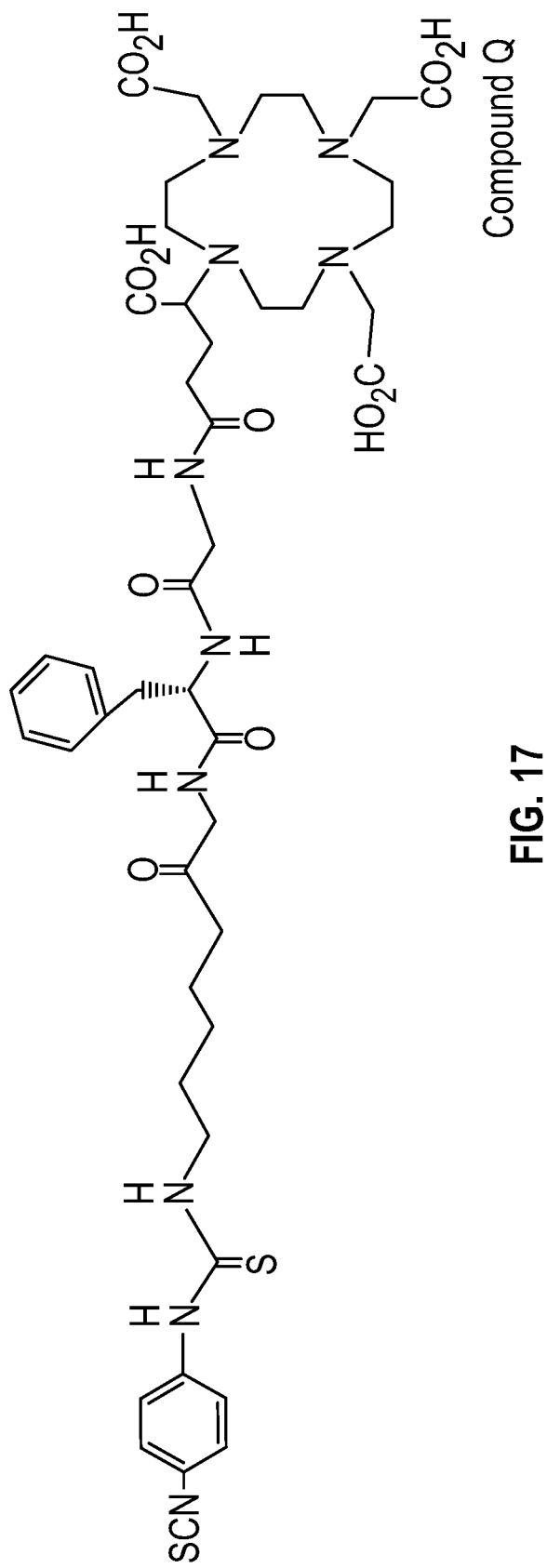
FIG. 17 shows a bifunctional chelator compound of Formula Q.

The bifunctional chelator compounds of the present disclosure may include a compound having the formula (Q) (FIG. 17), or a metal complex thereof:

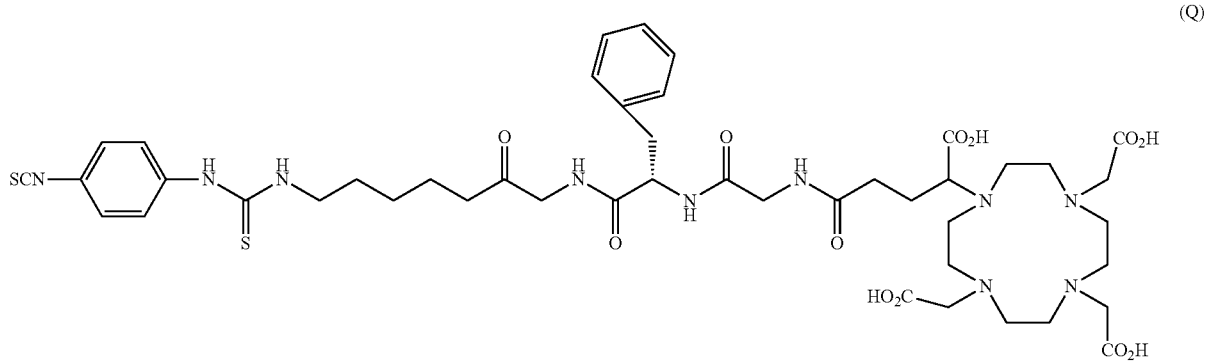

The bifunctional chelator compounds of the present disclosure may include a compound having the formula (I), or a metal complex thereof:

$$M—L_1—R \qquad (I)$$

wherein R is a reactive group, $L_1$ is a linker group, and M is a chelator moiety.

The reactive group R may include any suitable reactive group for conjugation of the bifunctional chelator to a target molecule, such as a protein or a peptide. A reactive group may include, but is not limited to, N-hydroxysuccinimide ester/NHS ester (herein "NETS"), thiocyanate (hereinafter "SCN"), a phenyloxadiazolyl methylsulfone (hereinafter "PODS"), and the like. The present disclosure also provides the corresponding ethylsulfone and propylsulfone analogs of the phenyloxadiazolyl methylsulfone (PODS) bifunctional chelator compounds. The NHS or SCN reactive groups may be used for conjugation to molecules having primary amine groups. The PODS reactive group may be used for conjugation to molecules having free thiols. The present disclosure also provides corresponding bifunctional chelator compounds having, instead, a 4-pyridyl reactive group for conjugation to molecules including primary amine groups, such as via the Zincke reaction.

The chelator moiety M may include DOTA, DOTA-GA, DOTA derivative chelator moieties, or any of the chelator moieties disclosed herein.

The linker group $L_1$ may include at least one component selected from: a benzyl group, at least one amino acid and/or amino acid derivative, a PEG spacer, a non-aromatic cyclic hydrocarbon, a linear hydrocarbon, ethyleneamine, thiourea, and the like, wherein when more than one component is included, the reactive group is a terminal component and any additional components may be in any order.

$L_1$ may include the formula (IA):

—CH$_2$(C$_6$H$_4$)NH—R$_2$—(R$_3$)$_{n2}$—(R$_4$)$_{n3}$—(C(O))$_{n4}$—(R$_5$)$_n$—(NHCH$_2$CH$_2$)$_{n5}$—(OCH$_2$CH$_2$)$_{n6}$—R$_6$—(C$_6$H)$_{n7}$— wherein n2-n7 is 0 or 1; $R_2$ is —C(S)—, —C(S)NH—, —C(O)CH$_2$CH$_2$—, C(O)CH$_2$CH$_2$C(O)—; $R_3$ is CH$_2$, NHCH$_2$, or (CH$_2$)$_{n1}$, where n1 is 1 to 5; $R_4$ is a cyclic alkane having 5 to 8 carbons or linear alkane having 1 to 6 carbons; $R_5$ is an amino acid or amino acid derivative, wherein n is 1, 2, or 3; and $R_6$ is —NHC(S)NH—, —C(S)NH—, —C(O)NH—, NH(CH$_2$)$_2$NHC(O)(CH$_2$)$_2$, or NHC(O)(CH$_2$)$_2$—.

For Compound A, $L_1$ may include:
—CH$_2$(C$_6$H$_4$)NH—C(S)NH—CH$_2$—(C$_6$H$_6$)—C(O)—R$_5$—NHCH$_2$CH$_2$—(OCH$_2$CH$_2$)$_n$—NHC(S)NH—C$_6$H$_4$— wherein $R_5$ is naphthylalanine.

For Compound B, $L_1$ may include:
—CH$_2$(C$_6$H$_4$)NH—C(S)NH—CH$_2$—CH$_2$—C(O)—(R$_5$)$_3$ —C(S)NH—(C$_6$H$_4$)n— wherein $R_5$ is -methionine-valine-lysine-.

For Compound I, $L_1$ may include:
—CH$_2$(C$_6$H$_4$)NH—C(S)NH—NHCH$_2$—(C$_6$H$_6$)—C(O)—R$_5$—NHCH$_2$CH$_2$—(OCH$_2$CH$_2$)$_3$—NHC(O)CH$_2$CH$_2$— wherein $R_5$ is naphthylalanine.

For Compound I, $L_1$ may include:
—CH$_2$(C$_6$H$_4$)NH—C(S)—(R$_5$)$_3$—NHCH$_2$CH$_2$—(OCH$_2$CH$_2$)$_3$—NHC(O)CH$_2$CH$_2$— wherein $R_5$ is -naphthylalanine-glycyl-lysine-.

For Compound K, $L_1$ may include:
—CH$_2$(C$_6$H$_4$)NH—C(S)—(R$_5$)$_3$—NHCH$_2$CH$_2$—NHC(O)CH$_2$CH$_2$— wherein $R_5$ is -methionine-valine-lysine-.

For Compound L, $L_1$ may include:
—CH$_2$(C$_6$H$_4$)NH—C(O)CH$_2$CH$_2$C(O)—NHCH$_2$—(C$_6$H$_6$)—C(O)—R$_5$—NHCH$_2$CH$_2$—(OCH$_2$CH$_2$)$_3$—NHC(O)CH$_2$CH$_2$— wherein $R_5$ is naphthylalanine.

For Compound M, $L_1$ may include:
—CH$_2$(C$_6$H$_4$)NH—C(O)CH$_2$CH$_2$—C(O)—(R$_5$)$_3$—(OCH$_2$CH$_2$)$_3$—NHC(O)CH$_2$CH$_2$— wherein $R_5$ is naphthylalanine-glycyl-lysine.

For Compound N, $L_1$ may include:
—CH$_2$(C$_6$H$_4$)NH—C(O)CH$_2$CH$_2$—C(O)—(R$_5$)$_3$—NHCH$_2$CH$_2$—NHC(O)CH$_2$CH$_2$— wherein $R_5$ is -methionine-valine-lysine-.

The bifunctional chelator compounds of the present disclosure may include a compound having the formula (II), or a metal complex thereof:

$$M—L_2—R \qquad (II)$$

wherein R is a reactive group according to the present disclosure, $L_2$ is a linker group of the present disclosure, and M is a chelator moiety of the present disclosure.

The linker group $L_2$ may include the formula (IIA):

—R$_1$—(R$_2$)$_{n1}$—(C(O))$_{n2}$—(R$_3$)$_n$—(NHCH$_2$CH$_2$)$_{n3}$—(OCH$_2$CH$_2$)$_{n4}$—R$_5$—(C$_6$H$_4$)$_{n4}$— (IIA)

wherein: n1-n5 is 0 or 1; $R_1$ is —$CH_2C(O)NHCH_2$—, —$C(CO_2H)CH_2CH_2C(O)NHCH_2$—, —$C(CO_2H)CH_2CH_2C(O)$—, or —$C(CO_2H)CH_2CH_2$—; $R_2$ is a cyclic alkane having 5 to 8 carbons or linear alkane having 1 to 6 carbons; $R_3$ is an amino acid or amino acid derivative; n is 1, 2, or 3; and $R_4$ is —NHC(S)NH—, —C(S)NH—, —NHC(O)$CH_2CH_2$C(O)NH—, —NHC(O)$CH_2CH_2$C(O)—, —NHC(O)$CH_2CH_2$—, —C(O)$CH_2CH_2$C(O)NH—, or —C(O)$CH_2CH_2$C(O)—.

For Compound C, $L_2$ may include:
—$CH_2C(O)NHCH_2$—($C_6H_6$)—C(O)—$R_3$—NHCH$_2$CH$_2$—(OCH$_2$CH$_2$)$_3$—NHC(S)NH—($C_6H_4$)—
wherein $R_3$ is naphthylalanine.

For Compound D, $L_2$ may include:
—C(CO$_2$H)CH$_2$CH$_2$C(O)NHCH$_2$—(O$_6H_6$)—C(O)—$R_3$—NHCH$_2$CH$_2$—(OCH$_2$CH$_2$)$_3$—NHC(O)CH$_2$CH$_2$C(O)NH—($C_6H_4$)—
wherein $R_3$ is naphthylalanine.

For Compound E, $L_2$ may include:
—C(CO$_2$H)CH$_2$CH$_2$C(O)NHCH$_2$—(O$_6H_6$)—C(O)—$R_3$—NHCH$_2$CH$_2$—(OCH$_2$CH$_2$)$_3$—NHC(O)CH$_2$CH$_2$C(O)—
wherein $R_3$ is naphthylalanine.

For Compound F, $L_2$ may include:
—C(CO$_2$H)CH$_2$CH$_2$—C(O)—$R_3$—C(S)NH—($C_6H_4$)—
wherein $R_3$ is naphthylalanine-lysine.

For Compound G, $L_2$ may include:
—C(CO$_2$H)CH$_2$CH$_2$C(O)NHCH$_2$—C(O)—$R_3$—C(O)CH$_2$CH$_2$C(O)—
wherein $R_3$ is naphthylalanine-lysine.

For Compound H, $L_2$ may include:
—C(CO$_2$H)CH$_2$CH$_2$—C(O)—$R_3$—C(O)CH$_2$CH$_2$C(O)NH—($C_6H_4$)—
wherein $R_3$ is lysine-naphthylalanine-lysine.

For Compound O, $L_2$ may include:
—C(CO$_2$H)CH$_2$CH$_2$—C(O)—$R_3$—C(O)CH$_2$CH$_2$C(O)—
wherein $R_3$ is methionine-valine-lysine.

For Compound P, $L_2$ may include:
—C(CO$_2$H)CH$_2$CH$_2$—C(O)—$R_3$—C(O)CH$_2$CH$_2$C(O)NH—($C_6H_4$)—
wherein $R_3$ is methionine-valine-lysine.

For Compound Q, $L_2$ may include:
—C(CO$_2$H)CH$_2$CH$_2$—C(O)—$R_3$—C(S)NH—($C_6H_4$)—
wherein $R_3$ is glycyl-phenyalanyl-lysine.

The bifunctional chelator compounds of the present disclosure may include a compound having the formula (III), or a metal complex thereof:

$$M_1—L_a—R \quad \text{(III)}$$

wherein R is a reactive group according to the present disclosure, $L_a$ is a linker group of the present disclosure, and $M_1$ is a chelator moiety of the present disclosure.

A chelator moiety $M_1$ may include, but is not limited to, a chelator moiety having the formula (IIIA), (IIIB), or (IIIC):

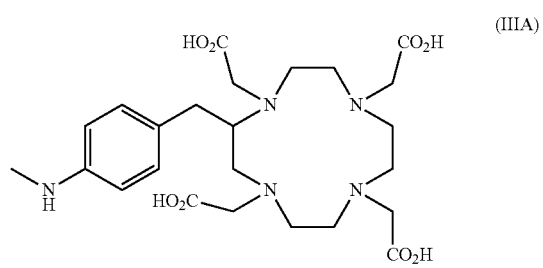

(IIIA)

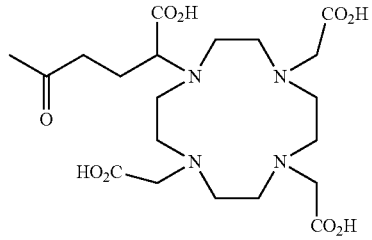

(IIIB)

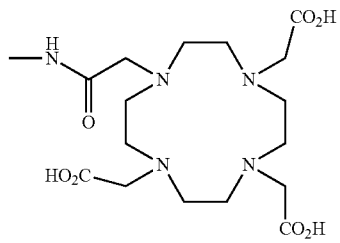

(IIIC)

wherein IIIA is S-2-(4-aminobenzyl)-1,4,7,10-tetraazacyclododecane tetraacetic acid (i.e., p-NH$_2$-Bn-DOTA); IIIB is (R)-5-(tert-butoxy)-5-oxo-4-(4,7,10-tris(2-(tert-butoxy)-2-oxoethyl)-1,4,7,10-tetraazacyclododecan-1-yl)pentanoic acid (i.e., (R)-DOTA-GA(tBu)$_4$); and IIIC is 5-(tert-butoxy)-5-oxo-4-(4,7,10-tris(2-(tert-butoxy)-2-oxoethyl)-1,4,7,10-tetraazacy cl odode cane-1-yl)-methylamine.

A reactive group R may include, but is not limited to, a reactive group having the formula (IIID), (TILE), or (IIIF):

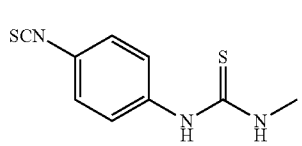

(IIID)

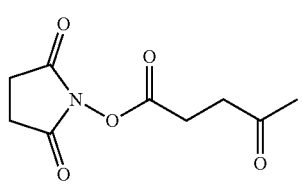

(IIIE)

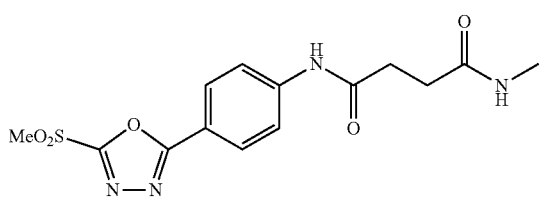

(IIIF)

The linker group $L_a$ may include the formula (IIIG):

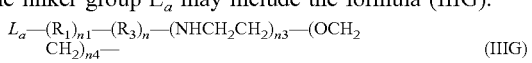

$$L_a—(R_1)_{n1}—(R_3)_n—(NHCH_2CH_2)_{n3}—(OCH_2CH_2)_{n4}— \quad \text{(IIIG)}$$

wherein: n1-n4 is 0 or 1; $R_1$ is —C(S)NHCH$_2$—$(R_2)_{n2}$—C(O), —C(S)NHNHCH$_2$—$(R_2)_{n2}$—C(O), —NHCH$_2$—$(R_2)_{n2}$—C(O), —C(S)NH, —C(O)CH$_2$CH$_2$C(O)NH(R$_2$)C(O)—, —C(O)CH$_2$CH$_2$C(O)NHCH$_2$(R$_2$)C(O)—, —R$_2$C(O), or —C(O)CH$_2$CH$_2$C(O)NH—, wherein $R_2$ is a cyclohexane or CH$_2$; $R_3$ is an amino acid or amino acid derivative; and n is 1, 2, or 3.

Exemplary linker groups $L_a$ include:
—C(S)NHCH$_2$(C$_6$H$_6$)C(O)—R$_3$—(NHCH$_2$CH$_2$)—(OCH$_2$CH$_2$)$_3$—, wherein R$_3$ is naphthylalanine;
—C(S)NHCH$_2$(CH$_2$)C(O)—R$_3$—, wherein R$_3$ is -methionine-valine-lysine-;
—(C$_6$H$_6$)C(O)—R$_3$—(NHCH$_2$CH$_2$)—(OCH$_2$CH$_2$)$_3$—, wherein R$_3$ is naphthylalanine;
—NHCH$_2$—(C$_6$H$_6$)—C(O)—R$_3$—(NHCH$_2$CH$_2$)—(OCH$_2$CH$_2$)$_3$—, wherein R$_3$ is naphthylalanine;
—NHCH$_2$—(C$_6$H$_6$)—C(O)—R$_3$—(NHCH$_2$CH$_2$)—, wherein R$_3$ is naphthylalanine;
—NHCH$_2$—C(O)—R$_3$—, wherein R$_3$ is naphthylalanine-lysine or glycyl-phenylalanyl-lysine;
—R$_3$—, wherein R$_3$ is lysine-naphthylalanine-lysine or methionine-valine-lysine or glycyl-phenylalanyl-lysine;
—C(S)NHNHCH$_2$(C$_6$H$_6$)C(O)—R$_3$—(NHCH$_2$CH$_2$)—(OCH$_2$CH$_2$)$_3$—, wherein R$_3$ is naphthylalanine;
—C(S)NH—R$_3$—(NHCH$_2$CH$_2$)—(OCH$_2$CH$_2$)$_3$—, wherein R$_3$ is -naphthylalanine-glycyl-lysine-;
—C(S)NH—R$_3$—(NHCH$_2$CH$_2$)—, wherein R$_5$ is -methionine-valine-lysine-;
—C(O)CH$_2$CH$_2$C(O)NHCH$_2$(C$_6$H$_6$)C(O)—R$_3$—(OCH$_2$CH$_2$)$_3$—, wherein R$_3$ is naphthylalanine;
—C(O)CH$_2$CH$_2$C(O)NH—R$_3$—(OCH$_2$CH$_2$)$_3$—, wherein R$_3$ is naphthylalanine-glycyl-lysine; and
—C(O)CH$_2$CH$_2$C(O)NH—R$_3$—(NHCH$_2$CH$_2$)—, wherein R$_3$ is methionine-lysine-valine.

The bifunctional chelator compounds may include a PEG spacer, wherein a PEG spacer may include any inert spacer that does not affect the conformational properties of the compound to which the spacer is attached. A PEG spacer of the present disclosure may include, but is not limited to, a PEG linker having an average molecular weight from 0.1 KD to 50 KD. The average molecular weight may be at least 0.1 KD, including, but not limited to, at least 0.5, 1, 5, 10, 15, 20, 25, 30, 35, 40, 45, and at least 50 KD. The average molecular weight may be no more than 50 KD, including, but not limited to, 45, 40, 35, 30, 25, 20, 15, 10, 5, 1, 0.5, and 0.1 KD. Any combination of lower and upper limits may define the average molecular weight, including, but not limited to, 0.1 KD to 1 KD, 1 KD to 5 KD, 5 KD to 15 KD, 15 KD to 25 KD, 25 KD to 35 KD, and 35 KD to 50 KD. The PEG spacer of the present disclosure may include (PEG)$_n$, wherein n is 1 or an integer greater than 1, such as an integer from 1 to 1000 or any integer value therein or any subrange of integers therein, such as from 1 to 100 or 1 to 20. For example, n may be 1, 2, 3, 4, 5, 6, 7, 8, 9, or 10.

The bifunctional chelator compounds of the present disclosure may include at least one amino acid or amino acid derivative. The at least one amino acid or amino acid derivative, may include, but is not limited to, Naphthylalanine, lysine, valine, methionine, glycyl, phenylalanyl, and the like.

The bifunctional chelator compounds of the present disclosure may include a chelator moiety, which may include, but it not limited to, dodecane tetraacetic acid (hereinafter "DOTA"), DOTA-GA, DOTA derivative chelator moieties, and the like. As used herein, "GA" may refer to glutaric acid. The present disclosure provides bifunctional chelator compounds in which the chelator moiety includes 1,4,7,10-tetraazacyclododecane-1,4,7-triacetic acid (DO3A) or a derivative thereof; 1,4,7-triazacyclononane-1,4-diacetic acid (NODA) or a derivative thereof; 1,4,7-triazacyclononane-1,4,7-triacetic acid (NOTA) or a derivative thereof; 1,4,7,10-tetraazacyclododecane-1,4,7,10-tetraacetic acid (DOTA) or a derivative thereof; 1,4,7-triazacyclononane, 1-glutaric acid-4,7-diacetic acid (NODAGA) or a derivative thereof; 1,4,7,10-tetraazacyclodecane, 1-glutaric acid-4,7,10-triacetic acid (DOTAGA) or a derivative thereof; 1,4,8,11-tetraazacyclotetradecane-1,4,8,11-tetraacetic acid (TETA) or a derivative thereof; 1,4,8,11-tetraazabicyclo[6.6.2]hexadecane-4,11-diacetic acid (CB-TE2A) or a derivative thereof; diethylene triamine pentaacetic acid (DTPA), its diester, or a derivative thereof; 2-cyclohexyl diethylene triamine pentaacetic acid (CHX-A"-DTPA) or a derivative thereof; deforoxamine (DFO) or a derivative thereof; 1,2-[[6-carboxypyridin-2-yl]methylamino]ethane (H2dedpa) or a derivative thereof; DADA or a derivative thereof; 1,4,7,10-Tetraazacyclododecane-1,4,7,10-tetra(methylene phosphonic acid) (DOTP) or a derivative thereof; 4-amino-[[16-[(6-carboxypyridin-2-yl)methyl]-1,4,10,13-tetraoxa-7,16-diazacyclooctadec-7-yl]methyl]pyridine-2-carboxylic acid (MACROPA-NH2) or a derivative thereof; MACROPA or a derivative thereof; 1,4,7,10-tetrakis(carbamoylmethyl)-1,4,7,10-tetraazacyclododecane (TCMC) or a derivative thereof; {4-[2-(bis-carboxymethylamino)-ethyl]-7-carboxymethyl-[1,4,7]triazonan-1-yl}-acetic acid (NETA) or a derivative thereof; Diamsar or a derivative thereof; 1,4,7-triazacyclononane-1,4,7-tris[methyl(2-carboxyethyl)phosphinic acid (TRAP, PRP9, TRAP-Pr) or a derivative thereof; N,N'-bis(6-carboxy-2-pyridylmethyl)ethylenediamine-N,N'-diacetic acid (H4octapa) or a derivative thereof; N,N'-[1-benzyl-1,2,3-triazole-4-yl]methyl-N,N'46-(carboxy)pyridin-2-yl]-1,2-diaminoethane (H2azapa) or a derivative thereof; N,N"-[[6-(carboxy)pyridin-2-yl]methyl]diethylenetriamine-N,N',N"-triacetic acid (H5decapa) or a derivative thereof; N,N'-bis(2-hydroxy-5-sulfobenzyl)ethylenediamine-N,N'-diacetic acid (SHBED) or a derivative thereof; N,N'-bis(2-hydroxybenzyl)ethylenediamine-N,N'-diacetic acid (HBED) or a derivative thereof; 3,6,9,15-tetraazabicyclo[9.3.1]pentadeca-1(15),11,13-triene-3,6,9,-triacetic acid (PCTA) or a derivative thereof; desferrioxamine B (DFO) or a derivative thereof; N,N'-(methylenephosphonate)-N,N'[6-(methoxycarbonyl)pyridin-2-yl]methyl-1,2-diaminoethane (H6phospa) or a derivative thereof; 1,4,7,10,13,16-hexaazacyclohexadecane-N,N',N",N''',N'''',N'''''-hexaacetic acid (HEHA) or a derivative thereof; 1,4,7,10,13-pentaazacyclopentadecane-N,N',N",N''',N''''-pentaacetic acid (PEPA) or a derivative thereof; or 3,4,3-LI(1,2-HOPO) or a derivative thereof.

The protein or peptide may be a cancer cell targeting agent that binds to an antigen/target molecule that is preferentially expressed or overexpressed on mammalian cancer cells such as human cancer cells. The protein may be an antibody, such as a monoclonal antibody, or an antigen-binding fragment thereof such as a Fab fragment, Fab2 fragment, or scFv molecule, a minibody, a diabody, or a nanobody, or an antibody mimetic protein such as a designed ankyrin repeat proteins (DARPin).

The present disclosure provides compositions including, but not limited to, radiopharmaceutical compositions and/or radiodiagnostic (radio-imaging) compositions, and the like. Radiopharmaceutical compositions and/or radiodiagnostic compositions may include one or more pharmaceutically acceptable carriers or excipients. Such carriers and excipients are well known in the art. As a non-limiting example, injectable drug delivery systems include solutions, suspensions, gels, microspheres and polymeric injectables, and may include excipients such as solubility-altering agents (e.g., ethanol, propylene glycol and sucrose) and polymers (e.g., polycaprylactones and PLGA's). Radioconjugate aspects of the present disclosure may be formulated with excipients as substantially described in U.S. Pat. No. 10,420, 851 or International Pub. No. WO 2017/155937, which are hereby incorporated by reference in their entirety. The formulation may include 0.5% to 5.0% (w/v) of one or more excipients, including, but not limited to, ascorbic acid, polyvinylpyrrolidone (PVP), human serum albumin (HSA), a water-soluble salt of HSA, any combination thereof, and the like. As a non-limiting example, the formulation may include 0.5-5% ascorbic acid; 0.5-4% polyvinylpyrrolidone (PVP); and a chelator conjugated affinity reagent protein such as an antibody, such as a monoclonal antibody, which may be radiolabeled or a chelated radionuclide in a buffered solution, such as in 50 mM PBS buffer, pH 7.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, radioprotectants, sorbents, suspending or dispersing agents, sweeteners, or waters of hydration. Exemplary excipients include, but are not limited to: ascorbic acid, histidine, phosphate buffer, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

As used herein, the term "antibody" includes, without limitation, (a) an immunoglobulin molecule including two heavy chains and two light chains and which recognizes an antigen; (b) polyclonal and monoclonal immunoglobulin molecules; (c) monovalent and divalent fragments thereof, such as Fab, di-Fab, as well as scFv molecules, diabodies, minibodies, single domain antibodies (sdAb), and nanobodies (VHH); (d) naturally occurring and non-naturally occurring, such as wholly synthetic antibodies, IgG-Fc-silent, and chimeric; and (e) bi-specific and multi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies may be human, humanized or nonhuman. When the present disclosure refers to or recites an "antibody," it is intended as referring to any of the full-length antibodies or fragments thereof disclosed herein, unless explicitly denoted otherwise. Further, wherever in this disclosure specific antibodies are disclosed, aspects directed to antigen binding fragments of such antibodies, such as Fab or $Fab_2$ fragments, or corresponding scFv molecules are intended to be provided and disclosed. Similarly, wherever in this disclosure specific antibodies are disclosed, corresponding aspects directed to full-length antibodies, antigen-binding antibody fragments, such as Fab or $Fab_2$ fragments, or scFv molecules that have the same immunoglobulin heavy chain CDRs and/or immunoglobulin light chain CDRs are also intended to be provided and disclosed. Such corresponding aspects may include one or both of the heavy chain variable region amino acid sequence and the light chain variable region amino acid sequence of the recited reference antibody. Antibody heavy chain and light chain complementarity determining regions (CDRs) and regions may be defined/delineated according to the Kabat or IMGT numbering conventions. Further, wherever in this disclosure antibody heavy chain or light chain sequences are disclosed that include N-terminal leader sequences, corresponding aspects including or consisting of the respective light chains without its leader sequence, e.g., beginning instead with the first amino acid residue of its respective variable region, are also intended to be provided and disclosed.

Single chain Fv molecules (scFv) are single polypeptide chain antibody molecules that include an immunoglobulin light chain variable region domain (VL domain) and an immunoglobulin heavy chain variable region domain (VH domain) joined by a peptide linker (L). An scFv molecule represents either VL-L-VH if the VL domain is the N-terminal part of the scFv molecule or VH-L-VL if the VH domain is the N-terminal part of the scFv molecule. Methods for making scFv molecules and for designing suitable peptide linkers are disclosed in U.S. Pat. Nos. 4,704,692 and 4,946,778, where are hereby incorporated by reference in their entirety.

The present disclosure provides a conjugate of any of the bifunctional chelators disclosed herein and a protein, such as a scFv molecule or a protein including at least one scFv molecule segment, that may include, in consecutive order (from amino to carboxyl terminal end), amino acids 1-120 of an immunoglobulin heavy chain variable region as disclosed herein (as a non-limiting example, where amino acid residue 1 is the first residue of the heavy chain variable region according to the Kabat numbering convention), followed by a linker amino acid sequence, followed by the amino acid sequence of a light chain variable region disclosed herein. The sequence of either or both of the heavy chain variable region portion and the light chain variable region portion of the scFv molecule may be minus 1, 2, 3, 4, or 5 amino acids at one or both ends with respect to the full-length variable region sequence. Such conjugates may be radiolabeled by chelation of a radionuclide to the chelator moiety of the conjugate.

The scFv linker amino acid sequence may, for example, include any of the amino acid sequences:

```
                                            (SEQ ID NO: 122)
     KISGGGGSGGGGSGGGGSGGGGSGGGGSS, (SEQ ID NO: 123)
     SPNSASHSGSAPQTSSAPGSQ,
```

($G_3S$)n where, for example, n is 1, 2, 3, 4, 5, 6, 7, 8, 9, or 10, such as $(G_3S)_4$, or ($G_4S$)n where, for example, n is 1, 2, 3, 4, 5, 6, 7, 8, 9, or 10, such as $(G_4S)_5$.

It should be further understood herein that wherever in the sequences of this disclosure an immunoglobulin heavy chain sequence or an immunoglobulin light chain sequence are provided that may include an amino terminal signal peptide sequence, corresponding amino acid sequences without the signal peptide sequences are also intended to be disclosed and that the various aspects of the present disclosure may be embodied with either the versions of the proteins with the signal peptide sequence or corresponding versions without the signal peptide sequences, and in any combination.

A protein, such as an antibody or fragment thereof or scFv molecule, or an antibody mimetic or a peptide that is conjugated to any of the bifunctional linkers disclosed herein may specifically bind to target antigens specifically expressed by or overexpressed by various types of cancer cells, such as one or more cancer antigens, including, but not limited to, the human forms thereof: CD33, DR5, 5T4 (trophoblast glycoprotein), HER2 (ERBB2; Her2/neu), HER3, TROP2 (TROP-2, EGP1, EGP-1), mesothelin, TSHR, CD19, CD123, CD22, CD30, CD45, CD171, CD138, CS-1, CLL-1, GD2, GD3, B-cell maturation antigen (BCMA), Tn Ag, prostate specific membrane antigen (PSMA), ROR1, FLT3, fibroblast activation protein (FAP), a Somatostatin receptor, Somatostatin Receptor 2 (SSTR2), Somatostatin Receptor 5 (SSTR5), gastrin-releasing peptide receptor (GRPR), NKG2D ligands (such as MICA, MICB, RAET1E/ULBP4, RAET1G/ULBP5, RAET1H/ULBP2, RAET1/ULBP1, RAET1L/ULBP6, and RAET1N/ULBP3), LYPD3 (C4.4A), Nectin-4, urokinase plasminogen activator receptor (uPAR), Folate receptor alpha (FOLR1), CUB-domain containing protein 1 (CDCP1), Glypican-3 (GPC3), tenascin, tenascin-C, CEACAM5, Cadherin-3, CCK2R, Neurotensin receptor type 1 (NTSR1), human Kallikrein 2 (hK2), norepinephrine transporter, Integrin alpha-V-beta-6, CD37, CD66, CXCR4, Fibronectin extradomain B (EBD), LAT-1, Carbonic anhydrase IX (CAIX), B7-H3 (a/k/a CD276), Disialoganglioside GD2 Antigen (GD2), calreticulin, phosphatidylserine, GRP78 (BiP), TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (Fra), MUC1, epidermal growth factor receptor (EGFR), EGFRvIII, NCAM, Prostase, PAP, ELF2M, Ephrin B2, IGF-I receptor, CAIX, LMP2, gp100, bcr-abl, tyrosinase, EphA2, Fucosyl GM1, sLe, GM3, DR5, 5T4, TGSS, HMW-MAA, o-acetyl-GD2, Folate receptor beta, TEM1/CD248, TEM7R, CLDN6, GPRC5D, CXORF61, CD97, CD 179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-A1, legumain, HPV E6,E7, MAGE A1, MAGEA3, MAGEA3/A6, ETV6-AML, sperm protein 17, XAGE1, Tie 2, MAD-CT-1, MAD-CT-2, Fos-related antigen 1, prostein, survivin and telomerase, PCTA-l/Galectin 8, KRAS, MelanA/MART1, Ras mutant, hTERT, sarcoma translocation breakpoints, ML-IAP, ERG (TMPRSS2 ETS fusion gene), NA17, PAX3, Androgen receptor, Cyclin B 1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GPA7, IGLL1, FGFR2, FGFR2b, Six-transmembrane epithelial antigen of prostate 1 (STEAP1), MUC17, claudin-18 isoform 2 (CLDN18.2), and Sortilin (Neurotensin receptor-3). Such conjugates radiolabeled by chelation with a radionuclide may be used to treat and/or diagnostically image a cancer in a mammalian subject such as a human patient. Targeting agents that are conjugated with a bifunctional chelator as disclosed herein may also include those that bind antigens expressed by immunosuppressive cells found in or associated with cancers such as CCR8 antigen expressed by tumor associated regulatory T-cells (Tregs) and CD33 antigen expressed by myeloid-derived suppressor cells (MDSCs) and tumor-associated macrophages (TAMs).

CD38 targeting agents that may be conjugated with any of the bifunctional chelators disclosed herein and radiolabeled for use as a radioconjugate include the monoclonal antibodies daratumumab (Darzalex®, Janssen Biotech, Inc.; heavy chain (SEQ ID NO:124), CDR-H1 (SEQ ID NO:125), CDR-H2 (SEQ ID NO:126), CDR-H3 (SEQ ID NO:127), light chain (SEQ ID NO:128), CDR-L1 (SEQ ID NO: 129), CDR-L2 (SEQ ID NO:130) and CDR-L3 (SEQ ID NO:131)), isatuximab (Sarclisa®, a/k/a SAR650984, Sanofi; reported heavy chain SEQ ID NO:132, CDR-H1 (SEQ ID NO:133), CDR-H2 (SEQ ID NO:134), CDR-H3 (SEQ ID NO:135), reported light chain SEQ ID NO:136, CDR-L1 (SEQ ID NO:137), CDR-L2 (SEQ ID NO:138), CDR-L3 (SEQ ID NO:139)), and MOR202 (MorphoSys AG; U.S. Pat. No. 8,088,896), as well as CD38-binding fragments thereof and antibodies having the same CDRs as daratumumab, isatuximab, or MOR202. CD38 targeting agents that may be conjugated with any of the bifunctional chelators disclosed herein and radiolabeled for use as a radioconjugate may include, but are not limited to, any of the anti-CD38 monoclonal antibodies disclosed in any of U.S. Pat. Nos. 8,088,896, 7,829,673, Int'l Pub. No. WO 2008/047242, U.S. Pat. No. 8,153,765 and U.S. Pub. No. 20210171653, CD38-binding fragments of any of said antibodies, and antibodies including the same CDRs as said antibodies.

The present disclosure provides a conjugate of any of the bifunctional chelators disclosed herein with a protein, such as an antibody, immunoglobulin heavy chain, immunoglobulin light chain, antibody fragment such as Fab fragment, Fab2 fragment or scFv molecules or fusion proteins, that include any of the amino acid sequences or combinations thereof set forth in SEQ ID NOS:1-139. The present disclosure provides a conjugate of any of the bifunctional chelators disclosed herein with any of the proteins, including, but not limited to, the antibodies, immunoglobulin heavy chains, immunoglobulin light chains, antibody fragments, such as Fab fragments, Fab2 fragments or scFv molecules, or fusion proteins that recognize cancer-or cancer-related antigens, disclosed in International Pub. No. WO2022235676 (of Int'l App. No. PCT/US2022/027479), which is hereby incorporated by reference in its entirety.

The protein that is conjugated with any of the bifunctional chelators disclosed herein may also be a modification of any one of the sequences set forth in any SEQ ID NOS: 1-139 that comprises one or more amino acid substitutions that have little to no effect on the structure or function of the sequence (e.g., conservative substitutions). In some aspects, two sequences are considered to be "homologous" to one another if the percent amino acid sequence identity is at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

DR5 targeting agents that may be conjugated with any of the bifunctional chelators disclosed herein and radiolabeled for use as a radioconjugate, may include, but are not limited to, any one or more of the monoclonal anti-DR5 antibodies mapatumumab, conatumumab, lexatumumab, tigatuzumab, drozitumab, and LBY-135.

5T4 targeting agents that may be conjugated with any of the bifunctional chelators disclosed herein and radiolabeled for use as a radioconjugate may include, but are not limited to, any one or more of the monoclonal anti-5T4 antibodies MED10641, ALG.APV-527, Tb535, H6-DM5, and ZV0508.

HER2 targeting agents that may be conjugated with any of the bifunctional chelators disclosed herein and radiolabeled for use as a radioconjugate may include the monoclonal antibodies trastuzumab and pertuzumab. The amino acid sequences of the light chain and the heavy chain of Trastuzumab reported by DrugBank Online are: light chain (SEQ ID NO:86) and heavy chain (SEQ ID NO:87). The amino acid sequences of the light chain and the heavy chain of Pertuzumab reported by DrugBank Online are: light chain (SEQ ID NO:88) and heavy chain (SEQ ID NO:89). The HER2 targeting agent used may be the ADC fam-trastuzumab deruxtecan-nxki (Enhertu®; Daiichi Sankyo, Japan).

HER3 targeting agents that may be conjugated with any of the bifunctional chelators disclosed herein and radiolabeled for use as a radioconjugate may include any one or more of the monoclonal antibodies patritumab, seribantumab, lumretuzumab, elgemtumab, GSK2849330, or AV-203 (Aveo Oncology) or any of the anti-HER3 antibodies disclosed in U.S. Pat. Nos. 10,494,441; 9,828,635; or U.S. Pub. No. 20210025006. An HER3 antibody may include, but is not limited to, an immunoglobulin heavy chain variable region including a CDRH1 including SEQ ID NO:56, a CDRH2 including SEQ ID NO:57, and a CDRH3 including SEQ ID NO:58, an immunoglobulin light chain variable region including a CDRL1 including SEQ ID NO:59, a CDRL2 including SEQ ID NO:60, and a CDRL3 including SEQ ID NO:61. An exemplary HER3 antibody includes an immunoglobulin heavy chain variable region including SEQ ID NO:62 and/or an immunoglobulin light chain variable region including SEQ ID NO:63. An exemplary HER3 antibody includes an immunoglobulin heavy chain amino acid sequence of SEQ ID NO:64 and/or an immunoglobulin light chain amino acid sequence of SEQ ID NO:65. The HER3 targeting agent used may be the ADC patritumab deruxtecan.

TROP2 targeting agents that may be conjugated with any of the bifunctional chelators disclosed herein and radiolabeled for use as a radioconjugate may include, but are not limited to, the monoclonal antibodies Sacituzumab and Datopotamab, antibodies having one or both of the heavy chain and light chain of said antibodies, antibodies having one or both of the heavy chain variable region and the light chain variable region of said antibodies, and antibodies having one or both of the heavy chain CDRs and the light chain CDRs of said antibodies, or TROP2-binding fragments of any of the aforementioned antibodies, such as Fab fragments, $Fab_2$ fragments, or corresponding scFv molecules. Sacituzumab biosimilar is commercially available as Catalog No. A2175 from BioVision Incorporated (an Abcam company, Waltham, MA, USA). Datopotamab biosimilar is commercially available as Catalog No. PX-TA1653 from ProteoGenix (Schiltigheim, France). The TROP2 targeting agent used may be the ADC Sacituzumab govitecan-hziy (Trodelvy®, Gilead Sciences, Inc., Foster City, CA, USA).

Further TROP2 targeting agents that may be conjugated with any of the bifunctional chelators disclosed herein and radiolabeled for use as a radioconjugate may include a monoclonal antibody having a heavy chain SEQ ID NO:66 and/or a light chain SEQ ID NO:71 (reported as the heavy and light chains of Sacituzumab), or an antibody including one or both of the heavy chain variable region (SEQ ID NO:67) or the light chain variable region (SEQ ID NO:72) of said chains, or an antibody including 1, 2, or 3 of the heavy chain CDRs of said heavy chain (CDR H1-3: SEQ ID NOS:68-70 respectively) and/or 1, 2 or 3 of the light chain CDRs of said light chain (CDR L1-3: SEQ ID NOS:73-75 respectively), and any of the anti-human TROP antibodies disclosed in U.S. Pat. No. 7,238,785 (such as mAb hRS7), U.S. Pat. Nos. 9,492,566, 10,195,517, or U.S. Pat. No. 11,116,846, or an antibody including one or both of the heavy chain and light chain variable regions of said antibodies, or an antibody including a heavy chain including 1, 2 or 3 of the heavy chain CDRs of any of said antibodies and/or a light chain including 1, 2, or 3 of the light chain CDRs of any of said antibodies.

TROP2 targeting agents that may be conjugated with any of the bifunctional chelators disclosed herein and radiolabeled for use as a radioconjugate may include, but are not limited to, a monoclonal antibody heavy chain SEQ ID NO:76 and/or a light chain SEQ ID NO:81 (reported as the heavy and light chains of Datopotamab), or an antibody including one or both of the variable region of said heavy chain (SEQ ID NO:77) and the variable region of said light chain (SEQ ID NO:82), or an antibody including 1, 2, or 3 of the heavy chain CDRs of said heavy chain (CDRs 1-3: SEQ ID NOS:78-80 respectively) and/or 1, 2 or 3 of the light chain CDRs of the said light chain (CDR H1-3: SEQ ID NOS:83-85 respectively), and any of the anti-human TROP antibodies disclosed in Int'l Pub. No. WO2015098099 or U.S. Pub. No. 20210238303, or an antibody including one or both of the heavy chain and light chain variable regions of said antibodies, or an antibody including a heavy chain including 1, 2 or 3 of the heavy chain CDRs of any of said antibodies and/or a light chain including 1, 2, or 3 of the light chain CDRs of any of said antibodies.

CD33 targeting agents that may be conjugated with any of the bifunctional chelators disclosed herein and radiolabeled for use as a radioconjugate may include the monoclonal antibodies lintuzumab (HuM195), gemtuzumab, and vadastuximab.

MUC1 targeting agents that may be conjugated with any of the bifunctional chelators disclosed herein and radiolabeled for use as a radioconjugate include hTABOO4 (OncoTAb, Inc.) and any of the anti-MUC1 antibodies or antibody fragments disclosed in any of U.S. Pub. No. 20200061216 and U.S. Pat. Nos. 8,518,405; 9,090,698; 9,217,038; 9,546,217; 10,017,580; 10,507,251 10,517,966; 10,919,973; 11,136,410; and 11,161,911.

LYPD3 (C4.4A) targeting agents that may be conjugated with any of the bifunctional chelators disclosed herein and radiolabeled for use as a radioconjugate may include, but are not limited to, BAY 1129980 (a/k/a Lupartumab amadotin; Bayer AG, Germany) an Auristatin-based anti-C4.4A (LYPD3) ADC or its antibody component Lupartumab, IgGi mAb GT-002 (Glycotope GmbH, Germany) and any of those disclosed in U.S. Pub. No. 20210309711, 20210238292, 20210164985, 20180031566, 20170158775, or 20150030618, 20120321619, Canadian Patent Application No. CA3124332A1, Taiwan Application No. TW202202521A, or Int'l Pub. No. WO2021260208, WO2007044756, WO2022042690, or WO2020138489.

5T4 targeting agents that may be conjugated with any of the bifunctional chelators disclosed herein and radiolabeled for use as a radioconjugate may include, but are not limited to, 5T4-binding, single chain, chimeric antibody-superantigen fusion proteins such as C215Fab-SEA (SEQ ID NO:93), 5T4Fab-SEA$_{D227A}$ (SEQ ID NO:94), and 5T4Fab-SEA/E-120 (SEQ ID NO:95). For example, naptumomab estafenatox is SEQ ID NO:96 (chimeric heavy chain component) non-covalently bound to SEQ ID NO:97 (light chain component). The heavy chain may include a 5T4 Fab heavy chain component (corresponding to residues 1 to 222 of SEQ ID NO:95), the SEA/E-120 superantigen (corresponding to residues 226 to 458 of SEQ ID NO:95), and a GGP tripeptide linker (corresponding to residues 223-225 of SEQ ID NO:95) covalently linking the Fab heavy chain and SEA/E-120 components. The light chain may include residues 459 to 672 of SEQ ID NO:95.

5T4 targeting agents that may be conjugated with any of the bifunctional chelators disclosed herein and radiolabeled for use as a radioconjugate may include, but are not limited to, C215Fab-SEA (SEQ ID NO:93), 5T4Fab-SEAD227A (SEQ ID NO:94), 5T4Fab-SEA/E-120 (SEQ ID NO:95); SEQ ID NO:96, Naptumomab estafenatox reported as SEQ ID NO:96 (heavy chain component) non-covalently associated with SEQ ID NO:97 (light chain component), an antibody including the Fab component of Naptumomab estafenatox, an antibody including the heavy chain component of any one of SEQ ID NOS:93-96 (for example, lacking the enterotoxin components thereof), a 5T4-binding antibody including the heavy chain component of any one of SEQ ID NOS:93-96 and an associated light chain component such as the light chain component of SEQ ID NO:97, a 5T4-binding antibody (such as a single- or multi-chain antibody, such as but not limited to a human or humanized IgG, such as IgG1) including a heavy chain component that includes 2 or 3 of the heavy chain CDRs present in any one of SEQ ID NOS:93-96, Naptumomab estafenatox modified by covalent linkage of the heavy chain and light chain components to each other by disulfide bonds (between cysteine residues in the manner of a Fab) and/or by a bifunctional thiol reactive crosslinking agent which may include and introduce a chelating moiety (such as DOTA), any of the chimeric 5T4-binding superantigen fusion proteins of U.S. Pat. Nos. 7,615,225, 10,314,910 and U.S. Pub. No. 20200101160, any of the preceding 5T4 targeting agents in which the antibody component(s) is/are humanized, any of the preceding in which an amino acid (for example, of a heavy chain and/or of a light chain) is substituted to a cysteine, and any of the preceding further including at least one additional amino acid (for example, in a heavy chain and/or in a light chain thereof) of which at least one is a cysteine and/or at least one is a lysine (for example, one or more additional C-terminal amino acids of which one or more are cysteines and/or of which one or more are lysines).

Light chain variations that may also be used include, but are not limited to, SEQ ID NO:99 (SEQ ID NO:97 with C-terminal lysine), SEQ ID NO:100 (SEQ ID NO: 97 with C-terminal cysteine), SEQ ID NO:101 (SEQ ID NO:97 with C-terminal lys-cys), and a light chain or light chain segment including 2 or 3 of the CDRs of the light chain of SEQ ID NO:97 — namely CDR-L1 KASQSVSNDVA (SEQ ID NO:119), CDR-L2 YTSSRYA (SEQ ID NO:120), and CDR-L3 QQDYNSPPT (SEQ ID NO:121).

Further 5T4 targeting agents that may be conjugated with any of the bifunctional chelators disclosed herein, and optionally radiolabeled, include proteins having or consisting of the following:

SEQ ID NO:102 [heavy chain portion only of SEQ ID NO:96];
an immunoglobulin heavy chain or heavy chain segment including 2 or 3 of the heavy chain CDRs found in SEQ ID NO:20, namely CDR-H1 GYYMH (SEQ ID NO:116), CDR-H2 RINPNNGVTLYNQKFKD (SEQ ID NO:117), and CDR-H3 STMITNYVMDY (SEQ ID NO:118);
SEQ ID NO:103 [SEQ ID NO:96 including linker, excluding enterotoxin portion];
SEQ ID NO:104 [SEQ ID NO:102 with C-terminal lysine];
SEQ ID NO:105 [SEQ ID NO:103 with C-terminal lysine];
SEQ ID NO:106 [SEQ ID NO:102 with C-terminal cysteine];
SEQ ID NO:107 [SEQ ID NO:103 with C-terminal cysteine];
SEQ ID NO:108 [SEQ ID NO:102 with C-terminal lys-cys];
SEQ ID NO:109 [SEQ ID NO:103 with C-terminal lys-cys];
SEQ ID NO:110 [5T4Fab-SEA/E-120 (SEQ ID NO:95) with C-terminal lysine];
SEQ ID NO:111 [SEQ ID NO:96 with C-terminal lysine];
SEQ ID NO:112 [5T4Fab-SEA/E-120 (SEQ ID NO:95) with C-terminal cysteine];
SEQ ID NO:113 [SEQ ID NO:96 with C-terminal cysteine];
SEQ ID NO:114 [5T4Fab-SEA/E-120 (SEQ ID NO:95) with C-terminal lys-cys];
SEQ ID NO:115 [SEQ ID NO:96 with C-terminal lys-cys]; and
any of SEQ ID NOS:96, 102-109, 111, 113 and 115 in non-covalent association with any of light chain SEQ ID NOS:97 and 99-101 to form a Fab without covalent cross-linking between chains, or a disulfide-bonded (cross-linked) form of such a Fab, or a form of such a Fab covalently cross-linked by a bifunctional cross-linker that may include a chelator such as DOTA.

The 5T4 targeting agent that may be conjugated to any of the bifunctional chelators disclosed herein may include, but is not limited to, an antibody, an antigen-binding antibody fragment, such as Fab or $Fab_2$, or an scFv molecule or a fusion protein, that includes immunoglobulin heavy chain CDRs 1, 2 and 3 as set forth in SEQ ID NOS:116, 117 and 118 respectively, and/or immunoglobulin light chain CDRs 1, 2 and 3 as set forth in SEQ ID NOS:119, 120 and 121 respectively. Such 5T4 targeting agents may further include an enterotoxin portion as disclosed herein, such as any of the modified enterotoxins SEA/E-120 (SEQ ID NO:91), SEAD227A (SEQ ID NO:92), and SEQ ID NO:98.

Where the 5T4 targeting agent includes a heavy chain and a light chain, one or both of the heavy chain and the light chain may be radiolabeled, for example, by chemical conjugation to any of the bifunctional chelators disclosed herein, and chelation of a radionuclide, such as $^{225}$AC or $^{177}$Lu, by the chelator.

Figure 22:
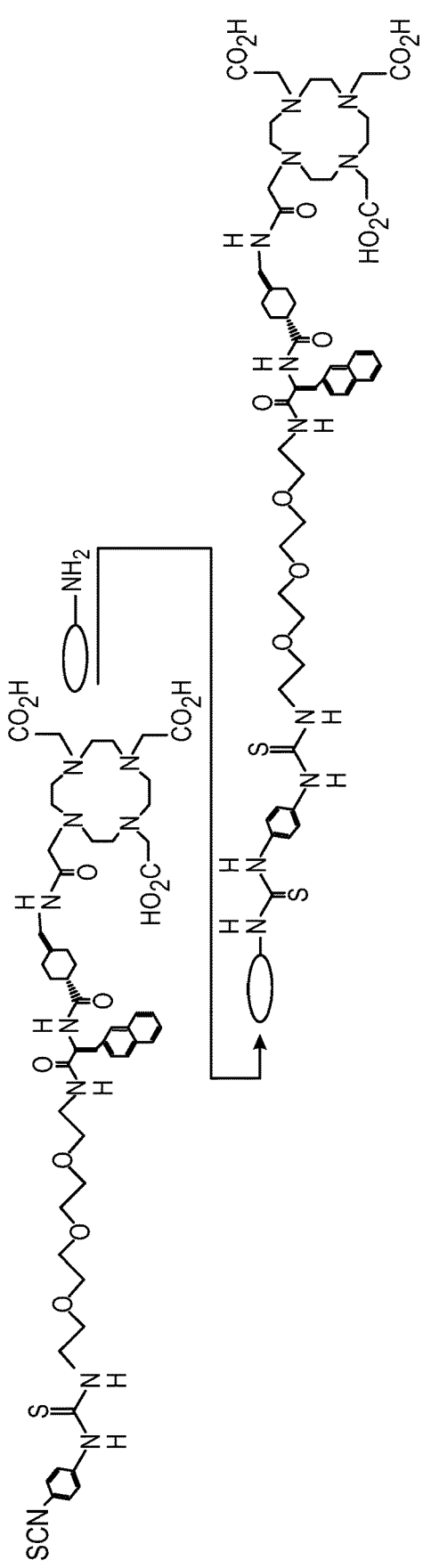
FIG. 22 shows conjugation of a bifunctional chelator molecule having a SCN reactive group to a primary amine of an amine presenting molecule.
Figure 23:
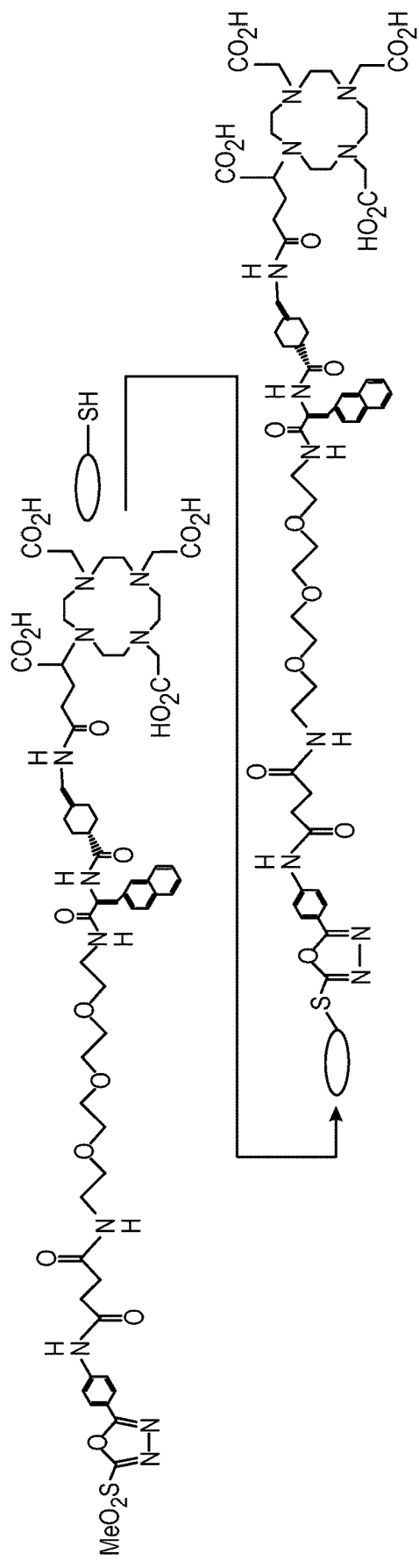
FIG. 23 shows conjugation of a bifunctional chelator molecule having a PODS reactive group to a thiol of a thiol presenting molecule.
Figure 24:
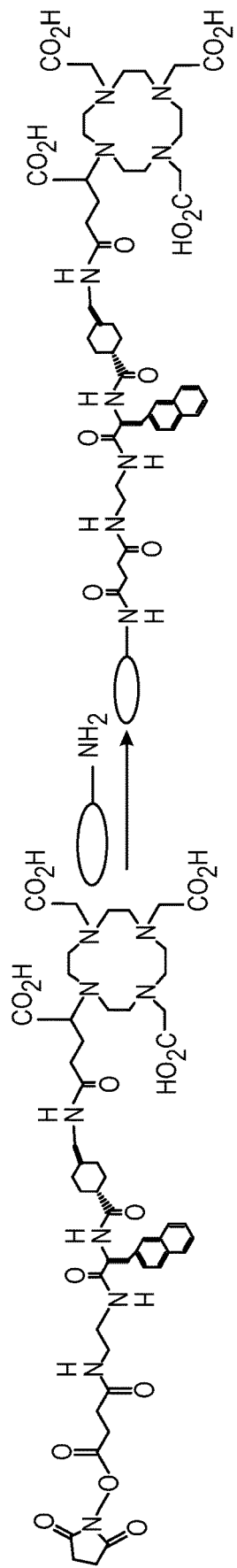
FIG. 24 shows conjugation of a bifunctional chelator molecule having a NHS reactive group to a primary amine of an amine presenting molecule.

The present disclosure provides a method for manufacturing a chelator-conjugated molecule, including the steps: reacting a molecule having at least one primary amine group with a bifunctional chelator compound of the present disclosure having an NHS or SCN reactive group to conjugate a chelator moiety of the bifunctional chelator compound to the molecule and/or reacting a molecule having at least one free thiol group with a bifunctional chelator compound of the present disclosure having a PODS reactive group to conjugate the bifunctional chelator compound to the molecule. Exemplary conjugation reactions are shown in FIGS. 22-24. The molecule may include, but is not limited to, a peptide, a synthetic peptide, a protein, a peptide ligand of a receptor protein, or a recombinant protein. The molecule may include, but is not limited to, an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

The method may include chelating one or more radionuclides to the chelator moiety of the bifunctional chelator compound before and/or after performing the conjugation. One or more radionuclide includes, but is not limited to, one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th. Accordingly, the molecule may include, but is not limited to, a 5T4 targeting agent of the present disclosure, wherein the 5T4 targeting agent binds human 5T4, such as naptumomab estafenatox. The molecule may include, but is not limited to, a CD38 targeting agent of the present disclosure.

The 5T4 targeting agent may include, but is not limited to, an antibody, an antibody fragment or an scFv molecule including an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

The present disclosure further provides a method of manufacturing a chelator-conjugated molecule according to Example 1.

The present disclosure provides a method of synthesizing a bifunctional chelator compound of the present disclosure according to Example 2, as shown in FIGS. 18-21.

Definitions

Unless otherwise defined, all terms (including technical and scientific terms) used herein have the same meaning as commonly understood by one of ordinary skill in the art to which this disclosure belongs.

As used herein, the term "and/or" includes any and all combinations of one or more of the associated listed items. Likewise, as used in the following detailed description, the term "or" is intended to mean an inclusive "or" rather than an exclusive "or." That is, unless specified otherwise, or clear from context, "X employs A or B" is intended to mean any of the natural inclusive permutations. Thus, if X employs A; X employs B; or X employs both A and B, then "X employs A or B" is satisfied under any of the foregoing instances.

The terminology used herein is for the purpose of describing particular examples only and is not intended to be limiting. As used herein, the singular forms "a", "an", and "the" may be intended to include the plural forms as well, unless the context clearly dictates otherwise. As example, "a" compound may comprise one or more compounds, and the like.

The terms "comprises", "comprising", "including", "having", and "characterized by", may be inclusive and therefore specify the presence of stated features, elements, compositions, steps, integers, operations, and/or components, but do not preclude the presence or addition of one or more other features, integers, steps, operations, elements, components, and/or groups thereof. Although these open-ended terms may be to be understood as a non-restrictive term used to describe and claim various aspects set forth herein, in certain aspects, the term may alternatively be understood to instead be a more limiting and restrictive term, such as "consisting of" or "consisting essentially of" Thus, for any given embodiment reciting compositions, materials, components, elements, features, integers, operations, and/or process steps, described herein also specifically includes embodiments consisting of, or consisting essentially of, such recited compositions, materials, components, elements, features, integers, operations, and/or process steps. In the case of "consisting of", the alternative embodiment excludes any additional compositions, materials, components, elements, features, integers, operations, and/or process steps, while in the case of "consisting essentially of", any additional compositions, materials, components, elements, features, integers, operations, and/or process steps that materially affect the basic and novel characteristics may be excluded from such an embodiment, but any compositions, materials, components, elements, features, integers, operations, and/or process steps that do not materially affect the basic and novel characteristics may be included in the embodiment.

Any method steps, processes, and operations described herein may not be construed as necessarily requiring their performance in the particular order discussed or illustrated, unless specifically identified as an order of performance. Thus, where a particular order is exemplified in this disclosure, corresponding aspects or embodiments having different ordering are also intended to be provided and disclosed. It is also understood that additional or alternative steps may be employed, unless otherwise indicated.

In addition, features described with respect to certain example embodiments may be combined in or with various other example embodiments in any permutational or combinatory manner. Different aspects or elements of example embodiments, as disclosed herein, may be combined in a similar manner. The term "combination", "combinatory," or "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included may be combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

In the description, certain details are set forth in order to provide a better understanding of various aspects of the systems and methods disclosed herein. However, one skilled in the art will understand that these aspects may be practiced without these details and/or in the absence of any details not described herein. In other instances, well-known structures, methods, and/or techniques associated with methods of practicing the various embodiments may not be shown or described in detail to avoid unnecessarily obscuring descriptions of other details of the various embodiments.

While specific aspects of the disclosure have been provided hereinabove, the disclosure may, however, be embodied in many different forms and should not be construed as necessarily being limited to only the embodiments disclosed herein. Rather, these embodiments may be provided so that this disclosure is thorough and complete, and fully conveys various concepts of this disclosure to skilled artisans.

All numerical quantities stated herein may be approximate, unless stated otherwise. Accordingly, the term "about" may be inferred when not expressly stated. The numerical quantities disclosed herein may be to be understood as not being strictly limited to the exact numerical values recited. Instead, unless stated otherwise, each numerical value stated herein is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding processes. Typical exemplary degrees of error may be within 20%, 10%, or 5% of a given value or range of values. Alternatively, the term "about" refers to values within an order of magnitude, potentially within 5-fold or 2-fold of a given value. Notwithstanding the approximations of numerical quantities stated herein, the numerical quantities described in specific examples of actual measured values may be reported as precisely as possible. Any numerical values, however, inherently contain certain errors necessarily resulting from the standard deviation found in their respective testing measurements.

All numerical ranges stated herein include all sub-ranges subsumed therein. For example, a range of "1 to 10" or "1-10" is intended to include all sub-ranges between and including the recited minimum value of 1 and the recited maximum value of 10 because the disclosed numerical ranges may be continuous and include every value between the minimum and maximum values. Any maximum numerical limitation recited herein is intended to include all lower numerical limitations. Any minimum numerical limitation recited herein is intended to include all higher numerical limitations.

Features or functionality described with respect to certain example aspects may be combined and sub-combined in and/or with various other example aspects. Also, different aspects and/or elements of example aspects, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, may be at least partially performed via at least one entity or actor in any manner.

All documents cited herein may be incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular aspects have been illustrated and described, it would be obvious to those skilled in the art that various other changes and modifications may be made without departing from the spirit and scope of the invention. Those skilled in the art will recognize or be able to ascertain using no more than routine experimentation, numerous equivalents to the specific apparatuses and methods described herein, including alternatives, variants, additions, deletions, modifications, and substitutions. This application including the appended claims is therefore intended to cover all such changes and modifications that may be within the scope of this application.

The term "functionally equivalent variant" or "functionally active variant" of an amino acid sequence of the present disclosure refers to a sequence resulting from modification of the amino acid sequence of the present disclosure by insertion, deletion, or substitution of one or more amino acids or nucleotides within the sequence or at either or both distal ends of the sequence, and which modification does not affect (in particular impair) a function of the amino acid sequence. The functionally active variant may be obtained by sequence alterations in the amino acid sequence, wherein the sequence alterations retain a function of the unaltered amino acid sequence. Such sequence alterations may include, but are not limited to, (conservative) substitutions, additions, deletions, mutations, and insertions.

The variant of the peptide is functionally active in the context of this disclosure if the activity of the amino acid sequence amounts to at least 10%, preferably at least 25%, more preferably at least more preferably 50%, even more preferably at least 70%, still more preferably at least 80%, especially at least 90%, particularly at least 95%, and most preferably at least 99% of the biological activity of the amino acid sequence as used according to the present disclosure, including the amino acid sequence without sequence alteration (i.e. the original sequence).

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with unchanged polar side chains, with small side chains, with large side chains, etc.

In another aspect of the present disclosure, the amino acid sequences as defined above may be modified by a variety of chemical techniques to produce derivatives having essentially the same activity (as defined above for fragments and variants) as the amino acid sequences, and optionally having other desirable properties.

As used herein, "percent (%) amino acid sequence identity" with respect to the amino acid sequences identified herein is defined as the percentage of amino acid residues in a candidate sequence that are identical with the amino acid residues in the specific amino acid sequence, after aligning the sequence and introducing gaps, if necessary, to achieve the maximum percent sequence identity, and not considering any conservative substitutions as part of the sequence identity. Those skilled in the art may determine appropriate parameters for measuring alignment, including any algorithms such as BLAST needed to achieve maximal alignment over the full length of the sequences being compared.

ASPECTS

Aspect 1: A bifunctional chelator compound comprising a formula (A)

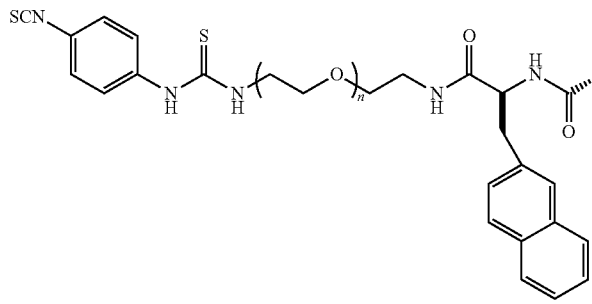

wherein n is 1 or an integer greater than 1.

Aspect 2: The bifunctional chelator of aspect 1, further comprising at least one radionuclide, wherein the radionuclide is chelated by the bifunctional chelator.

Aspect 3: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 4: A bifunctional chelator compound comprising a formula (B)

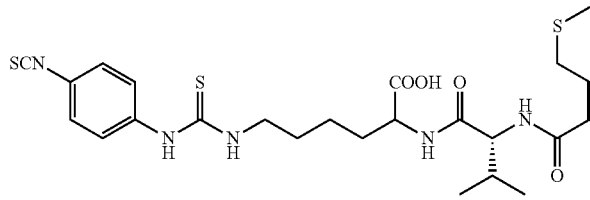

Aspect 5: The bifunctional chelator of aspect 4, further comprising at least one radionuclide, wherein the radionuclide is chelated by the bifunctional chelator.

Aspect 6: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 7: A bifunctional chelator compound comprising a formula (C) through formula (Q).

Aspect 8: The bifunctional chelator of aspect 7, further comprising at least one radionuclide, wherein the radionuclide is chelated by the bifunctional chelator.

Aspect 9: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 10: A bifunctional chelator compound comprising a formula (I)

$$M-L_1-R \qquad (I)$$

wherein R is a reactive group, wherein $L_1$ is a linker group, and wherein M is a chelator moiety.

Aspect 11: The bifunctional chelator of aspect 10, wherein $L_1$ comprises a formula (IA):

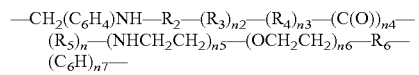

wherein n2-n7 is 0 or 1;

$R_2$ is —C(S)—, —C(S)NH—, —C(O)CH$_2$CH$_2$—, C(O)CH$_2$CH$_2$C(O)—;

$R_3$ is CH$_2$, NHCH$_2$, or (CH$_2$)$_{n1}$, wherein n1 is 1 to 5;

$R_4$ is a cyclic alkane having 5 to 8 carbons or linear alkane having 1 to 6 carbons;

$R_5$ is an amino acid or amino acid derivative, wherein n is 1, 2, or 3; and $R_6$ is —NHC(S)NH—, —C(S)NH, —C(O)NH—, NH(CH$_2$)$_2$NHC(O)(CH$_2$)$_2$, or NHC(O)(CH$_2$)$_2$—.

Aspect 12: The bifunctional chelator compound according to any of the foregoing aspects, further comprising at least one radionuclide, wherein the radionuclide is chelated by the bifunctional chelator.

Aspect 13: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 14: A bifunctional chelator compound comprising a formula (II)

$$M-L_2-R \qquad (II)$$

wherein R is a reactive group, wherein $L_2$ is a linker group, and wherein M is a chelator moiety.

Aspect 15: The bifunctional chelator of aspect 14, wherein $L_2$ may include the formula (IIA):

$$-R_1-(R_2)_{n1}-(C(O))_{n2}-(R_3)_n-(NHCH_2CH_2)_{n3}-(OCH_2CH_2)_{n4}-R_5-(C_6H_4)_{n4}-$$

wherein n1-n5 is 0 or 1;

$R_1$ is $-CH_2C(O)NHCH_2-$, $-C(CO_2H)CH_2CH_2C(O)NHCH_2-$, $-C(CO_2H)CH_2CH_2C(O)-$, or $-C(CO_2H)CH_2CH_2$;

$R_2$ is a cyclic alkane having 5 to 8 carbons or linear alkane having 1 to 6 carbons;

$R_3$ is an amino acid or amino acid derivative, wherein n is 1, 2, or 3; and $R_4$ is $-NHC(S)NH-$, $-C(S)NH-$, $-NHC(O)CH_2CH_2C(O)NH-$, $-NHC(O)CH_2CH_2C(O)-$, $-NHC(O)CH_2CH_2-$, $-C(O)CH_2CH_2C(O)NH-$, or $-C(O)CH_2CH_2C(O)-$.

Aspect 16: The bifunctional chelator compound according to any of the foregoing aspects, further comprising at least one radionuclide, wherein the radionuclide is chelated by the bifunctional chelator.

Aspect 17: The bifunctional chelator compound according to any of the foregoing aspects wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 18: A bifunctional chelator compound comprising a formula (III):

$$M_1-L_a-R \qquad (III)$$

wherein R is a reactive group, wherein $L_a$ is a linker group, and wherein $M_1$ is a chelator moiety.

Aspect 19: The bifunctional chelator compound according to aspect 18, wherein $L_a$ may include the formula (IIIG):

$$L_a=-(R_1)_{n1}-(R_3)_n-(NHCH_2CH_2)_{n3}-(OCH_2CH_2)_{n4}-$$

wherein n1-n4 is 0 or 1;

$R_1$ is $-C(S)NHCH_2-(R_2)_{n2}-C(O)$, $-C(S)NHNHCH_2-(R_2)_{n2}-C(O)$, $-NHCH_2-(R_2)_{n2}-C(O)$, $-C(S)NH$, $-C(O)CH_2CH_2C(O)NH(R_2)C(O)-$, $-C(O)CH_2CH_2C(O)NHCH_2(R_2)C(O)-$, $-R_2C(O)$, or $-C(O)CH_2CH_2C(O)NH-$;

$R_2$ is a cyclohexane or $CH_2R_2$ is a cyclohexane or $CH_2$; and $R_3$ is an amino acid or amino acid derivative, wherein n is 1, 2, or 3.

Aspect 20: The bifunctional chelator compound according to any of the foregoing aspects, wherein the chelator moiety is selected from:

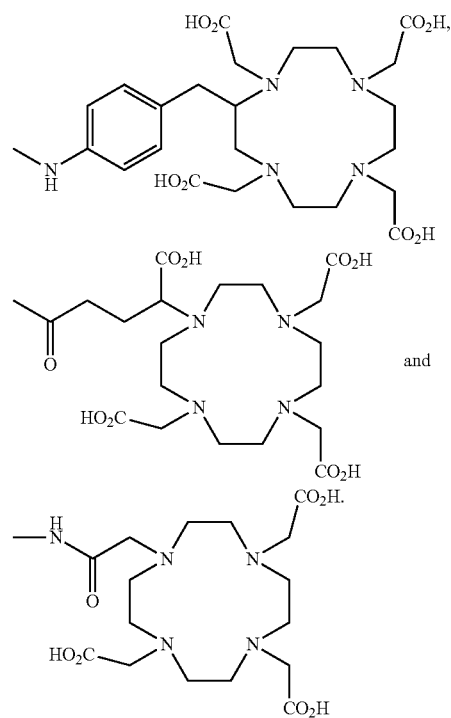

Aspect 21: The bifunctional chelator of claim according to any of the foregoing aspects, wherein the reactive group is selected from:

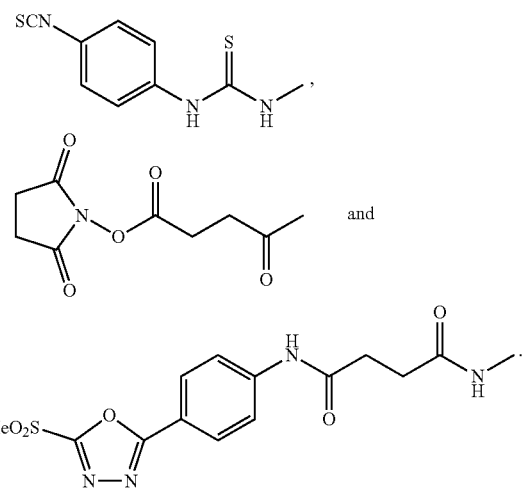

Aspect 22: The bifunctional chelator compound according to any of the foregoing aspects, further comprising at least one radionuclide, wherein the radionuclide is chelated by the bifunctional chelator.

Aspect 23: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Th, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 24: A conjugate of the bifunctional chelator compound of aspects 1-23 with a molecule comprising either of a primary amine group or a free thiol group.

Aspect 25: The conjugate of aspect 24, wherein the molecule comprises a peptide, a synthetic peptide, a protein, a recombinant protein, an antibody, a monoclonal antibody, an antigen-binding fragment of an antibody, an antigen-binding fragment of a monoclonal antibody, an immunoglobulin heavy chain, an immunoglobulin heavy chain variable region, immunoglobulin light chain, an immunoglobulin light chain variable region, a nanobody, a scFv molecule, or an antibody mimetic protein.

Aspect 26: The conjugate according to any of the foregoing aspects, wherein the molecule is a CD38 targeting agent.

Aspect 27: The conjugate according to any of the foregoing aspects, wherein the CD38 targeting agent is daratumumab, isatuximab, or MOR202.

Aspect 28: The conjugate according to any of the foregoing aspects, wherein the CD38 targeting agent is an antibody or an antibody fragment, comprising:
  an immunoglobulin heavy chain having the amino acid sequence as set forth in SEQ ID NO:124 and/or an immunoglobulin light chain having an amino acid sequence as set forth in SEQ ID NO:128;
  an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
  an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
  an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 29: The conjugate according to any of the foregoing aspects, wherein the molecule is a TROP2 targeting agent, wherein the TROP2 targeting agent binds human TROP2.

Aspect 30: The conjugate according to any of the foregoing aspects, wherein the TROP2 targeting agent is an antibody, an antibody fragment, or an scFv molecule, comprising:
  an immunoglobulin heavy chain having complementarity determining regions 1-3 of Sacituzumab and/or an immunoglobulin light chain having complementarity determining regions 1-3 of Sacituzumab;
  an immunoglobulin heavy chain having complementarity determining regions 1-3 with amino acid sequences as set forth in SEQ ID NOS:68-70, respectively, and/or an immunoglobulin light chain having complementarity determining regions 1-3 with amino acid sequences as set forth in SEQ ID NOS:73-75, respectively;
  an immunoglobulin heavy chain having complementarity determining regions 1-3 of Datopotamab and/or an immunoglobulin light chain having complementarity determining regions 1-3 of Datopotamab; or
  an immunoglobin heavy chain having complementarity determining regions 1-3 with amino acid sequences as set forth in SEQ ID NOS: 78-80, respectively, and/or an immunoglobulin light chain having complementarity determining regions 1-3 with amino acid sequences as set forth in SEQ ID NOS: 83-85, respectively.

Aspect 31: The conjugate according to any of the foregoing aspects, comprising the immunoglobulin heavy chain having complementarity determining regions with amino acid sequences as set forth in SEQ ID NOS:68-70 and/or the immunoglobulin light chain having complementarity determining regions with amino acid sequences as set forth in SEQ ID NOS:73-75; or comprising the immunoglobulin heavy chain having complementarity determining regions with amino acid sequences as set forth in SEQ ID NOS: 78-80 and/or the immunoglobulin light chain having complementarity determining regions with amino acid sequences as set forth in SEQ ID NOS: 83-85.

Aspect 32: The conjugate according to any of the foregoing aspects, wherein the molecule is a 5T4 targeting agent, wherein the 5T4 targeting agent binds human 5T4.

Aspect 33: The conjugate according to any of the foregoing aspects, wherein the 5T4 targeting agent is naptumomab estafenatox.

Aspect 34: The conjugate according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

Aspect 35: A composition comprising:
  a quantity of a conjugate according to any of the foregoing aspects; and
  at least one excipient.

Aspect 36: A composition comprising:
  a quantity of a conjugate according to any of the foregoing aspects,
  wherein the quantity of the conjugate comprises:
    a radiolabeled fraction, wherein the bifunctional chelator compound comprises a chelator moiety, wherein the chelator moiety chelates one or more radionuclides, and
    a non-radiolabeled fraction wherein the chelator moiety does not chelate a radionuclide.

Aspect 37: The composition according to any of the foregoing aspects, wherein the at least one radionuclide comprises one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 38: The composition according to any of the foregoing aspects, further comprising at least one excipient.

Aspect 39: A method for manufacturing a chelator-conjugated molecule, comprising the steps:
  reacting a molecule comprising at least one primary amine group with a bifunctional chelator compound having a NHS or SCN reactive group according to any one of claims 1 through 23 to conjugate the bifunctional chelator compound to the molecule.

Aspect 40: The method of aspect 39, wherein the molecule comprises a peptide, a synthetic peptide, a protein, or a recombinant protein.

Aspect 41: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 42: The method according to any of the foregoing aspects, wherein the molecule is a CD38 targeting agent.

Aspect 43: The method according to any of the foregoing aspects, wherein the CD38 targeting agent is daratumumab, isatuximab, or MOR202.

Aspect 44: The method according to any of the foregoing aspects, wherein the molecule comprises a peptide ligand of a receptor protein.

Aspect 45: The method according to any of the foregoing aspects, further comprising the step of chelating one or more radionuclides to the chelator moiety of the bifunctional chelator compound before and/or after performing the conjugation.

Aspect 46: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 47: The method according to any of the foregoing aspects, wherein the molecule is a 5T4 targeting agent, wherein the 5T4 targeting agent binds human 5T4.

Aspect 48: The method according to any of the foregoing aspects, wherein the 5T4 targeting agent is naptumomab estafenatox.

Aspect 49: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

Aspect 50: The method according to any of the foregoing aspects, wherein the CD38 targeting agent is an antibody or an antibody fragment, comprising:
an immunoglobulin heavy chain having the amino acid sequence as set forth in SEQ ID NO:124 and/or an immunoglobulin light chain having an amino acid sequence as set forth in SEQ ID NO:128;
an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 51: The method according to any of the foregoing aspects, wherein the CD38 targeting agent is an antibody or an antibody fragment, comprising any of the amino acid sequences as set forth in SEQ ID NOS: 124-139.

Aspect 52: A method for manufacturing a chelator-conjugated molecule, comprising the steps:
reacting a molecule comprising at least one free thiol group with a bifunctional chelator compound having a PODS reactive group according to any one of claims 7 through 23 to conjugate the bifunctional chelator compound to the molecule.

Aspect 53: The method of aspect 52, wherein the molecule comprises a peptide, a synthetic peptide, a protein, or a recombinant protein.

Aspect 54: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 55: The method according to any of the foregoing aspects, wherein providing the molecule comprising at least one free thiol group further comprises reducing a disulfide bond to generate the at least one free thiol group of the molecule.

Aspect 56: The method according to any of the foregoing aspects, wherein the molecule comprises a peptide ligand of a receptor protein.

Aspect 57: The method according to any of the foregoing aspects, wherein the molecule is a CD38 targeting agent.

Aspect 58: The method according to any of the foregoing aspects, wherein the CD38 targeting agent is daratumumab.

Aspect 59: The method according to any of the foregoing aspects, wherein the CD38 targeting agent is an antibody or an antibody fragment, comprising:
an immunoglobulin heavy chain having the amino acid sequence as set forth in SEQ ID NO:124 and/or an immunoglobulin light chain having an amino acid sequence as set forth in SEQ ID NO:128;
an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 60: The method according to any of the foregoing aspects, further comprising the step of chelating one or more radionuclides to the chelator moiety of the bifunctional chelator compound before and/or after performing the conjugation.

Aspect 61: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 62: The method according to any of the foregoing aspects, wherein the molecule is a 5T4 targeting agent, wherein the 5T4 targeting agent binds human 5T4.

Aspect 63: The method according to any of the foregoing aspects, wherein the 5T4 targeting agent is naptumomab estafenatox.

Aspect 64: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 65: The method according to any of the foregoing aspects, wherein the CD38 targeting agent is an antibody or an antibody fragment, comprising any of the amino acid sequences as set forth in SEQ ID NOS: 124-139.

Aspect 66: A method for manufacturing a chelator-conjugated molecule, comprising the steps:
reacting a molecule comprising at least one primary amine group with a bifunctional chelator compound having a NHS or SCN reactive group according to any one of claims 1 through 23 to conjugate the bifunctional chelator compound to the molecule; and
reacting a molecule comprising at least one free thiol group with a bifunctional chelator compound having a PODS reactive group according to any one of claims 7 through 23 to conjugate the bifunctional chelator compound to the molecule.

Aspect 67: The method according to aspect 66, wherein the molecule comprises a peptide, a synthetic peptide, a protein, or a recombinant protein.

Aspect 68: The method according to any of the foregoing aspects, wherein the method comprises reacting the molecule comprising at least one free thiol group, the method further comprises reducing a disulfide bond to generate the at least one free thiol group of the molecule.

Aspect 69: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 70: The method according to any of the foregoing aspects, wherein the molecule comprises a peptide ligand of a receptor protein.

Aspect 71: The method according to any of the foregoing aspects, wherein the molecule is a CD38 targeting agent.

Aspect 72: The method according to any of the foregoing aspects, wherein the CD38 targeting agent is daratumumab.

Aspect 73: The method according to any of the foregoing aspects, wherein the CD38 targeting agent is an antibody or an antibody fragment, comprising:
an immunoglobulin heavy chain having the amino acid sequence as set forth in SEQ ID NO:124 and/or an immunoglobulin light chain having an amino acid sequence as set forth in SEQ ID NO:128;
an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 74: The method according to any of the foregoing aspects, further comprising the step of chelating one or more radionuclides to the chelator moiety of the bifunctional chelator compound before and/or after performing the conjugation.

Aspect 75: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 76: The method according to any of the foregoing aspects, wherein the molecule is a 5T4 targeting agent, wherein the 5T4 targeting agent binds human 5T4.

Aspect 77: The method according to any of the foregoing aspects, wherein the 5T4 targeting agent is naptumomab estafenatox.

Aspect 78: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 79: The method according to any of the foregoing aspects, wherein the CD38 targeting agent is an antibody or an antibody fragment, comprising any of the amino acid sequences as set forth in SEQ ID NOS: 124-139.

Aspect 80: A chelator-conjugated molecule prepared according to the method of any one of aspects 39-79.

Aspect 81: The chelator-conjugated molecule of aspect 80, wherein the molecule is a 5T4 targeting agent that binds human 5T4.

Aspect 82: The chelator-conjugated molecule according to any of the foregoing aspects, wherein the 5T4 targeting agent is naptumomab estafenatox.

Aspect 83: The chelator-conjugated molecule according to any of the foregoing aspects, wherein the molecule is a CD38 targeting agent.

Aspect 84: The chelator-conjugated molecule according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 85: A composition comprising:
a quantity of a chelator-conjugated molecule according to any of the foregoing aspects;
a quantity of a radionuclide;
wherein the quantity of the chelator-conjugated molecule comprises a radiolabeled fraction, wherein the chelator moiety chelates the radionuclide and a non-radiolabeled fraction, and wherein the chelator moiety does not chelate any radionuclide.

Aspect 86: The composition of aspect 85, further comprising at least one excipient.

Aspect 87: The composition according to any of the foregoing aspects, wherein the radionuclide is selected from $^{13+}$Ce, $^{43}$Sc, $^{44}$Sc, $+^{7}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 88: A method of manufacturing a chelator-conjugated molecule according to Example 1.

Aspect 89: A method of synthesizing a bifunctional chelator compound according to Example 2, as shown in FIGS. 18-21.

EXAMPLES

Example 1: Preparation of a Radiolabeled Antibody

Preparing a chelator-conjugated antibody using an SCN (thiocyanate) reactive group bifunctional chelator: antibody conjugates are prepared by reacting a concentrated solution of monoclonal antibody with a SCN reactive group bifunctional chelator as disclosed herein in bicarbonate or in phosphate buffers at pH between about 8 and about 9 and by incubation at either about 37° C. or at room temperature. The molar ratio of antibody to bifunctional chelator is, for example, 1:10 or 1:20, or from 1:10 to 1:20. The conjugates are purified from excess of the bifunctional chelator by repeated filtration or centrifugation and by gravity size exclusion chromatography (SEC). During the purification process, the bicarbonate or phosphate buffer can be changed to N-2-Hydroxyethylpiperazine-N-2-ethanesulfonic acid (HEPES; Free Acid) or acetate medium. Conjugates are characterized by size exclusion high performance liquid chromatography (SE-HPLC).

Preparing a chelator-conjugated antibody using an NHS (NHS ester; N-hydroxysuccinimide ester) reactive group bifunctional chelator: The conjugation reaction between an antibody such as an IgG and an NHS ester reactive group bifunctional chelator is, for example, performed in 0.1 M NaHCO$_3$ buffer, pH 7.4, with 10- to 20-fold molar excess of bifunctional chelator to antibody, for 45 minutes to 1 hour, at room temperature/25° C. or 37° C. The conjugates are purified from excess of the bifunctional chelator by repeated filtration or centrifugation and by gravity size exclusion chromatography (SEC). During the purification process, the bicarbonate buffer can be changed to N-2-Hydroxyethylpiperazine-N-2-ethanesulfonic acid (HEPES; Free Acid) or acetate medium. Conjugates are characterized by size exclusion high performance liquid chromatography (SE-HPLC).

Preparing a chelator-conjugated antibody using a PODS (phenyloxadiazolyl methylsulfone) reactive group bifunctional chelator: A PODS reactive group bifunctional linker is conjugated to a monoclonal antibody, such as an IgG in the presence of TCEP, a mild reducing agent that reduces the inter-chain disulfide bonds within an immunoglobin to provide free thiols. The conjugation can be performed according to the methods set forth in U.S. Pat. No. 11,000,604.

In more detail, to a solution of 200 μg of antibody in PBS pH 7.4 (1 mg/mL) 1.33 μL of a fresh TCEP solution (10 mM in water, 10 eq.) is added concurrent with or followed by adding a suitable volume of a solution of a PODS reactive group bifunctional chelator (1 mM in DMSO). The reaction mixture is then stirred on a thermomixer (25° C. or 37° C.) for 30 min, 2 h, or 24 h. The resulting conjugate is then be purified on a size exclusion column (Sephadex G-25 M, PD-10 column, GE Healthcare; dead volume=2.5 mL, eluted with 2 mL of PBS, pH 7.4) and concentrated using centrifugal filtration units with a 50,000 Da molecular weight cut off (AMICON™ Ultra 4 Centrifugal Filtration Units, Millipore Corp., Billerica, MA, USA). The buffer in which the conjugate is dissolved can be changed to N-2-Hydroxyethylpiperazine-N-2-ethanesulfonic acid (HEPES; Free Acid) or acetate medium.

Radiolabeling the conjugate: A chelator-bearing conjugate is first prepared according to the aforementioned examples and then radiolabeled. Where the chelator moiety includes DOTA, DOTAGA or a DOTA derivative as exemplified herein, one radionuclide that is chelated is $^{225}$Ac.

An exemplary labeling reaction for $^{225}$Ac is as follows: A reaction including 15 μl 0.15 M NH$_4$Oac buffer, pH=6.5 and 2 μL (10 pg) chelator-conjugated antibody (5 mg/ml) is mixed in an Eppendorf reaction tube, and 4 μL $^{225}$Ac (10 μCi) in 0.05 M HCl subsequently added. The contents of the tube are mixed with a pipette tip and the reaction mixture incubated at 37° C. for 90 min with shaking at 100 rpm. At the end of the incubation period, 3 μL of a 1 mM DTPA solution is added to the reaction mixture and incubated at room temperature for 20 min to bind the unreacted $^{225}$Ac into the $^{225}$Ac-DTPA complex. Instant thin layer chromatography with 10 cm silica gel strip and 10 mM EDTA/normal saline mobile phase is used to determine the radiochemical purity of $^{225}$Ac-chelator-conjugated antibody through separating $^{225}$Ac-labeled antibody ($^{225}$Ac-chelator-conjugated antibody) from free $^{225}$Ac ($^{225}$Ac-DTPA). In this system, the radiolabeled antibody stays at the point of application and $^{225}$Ac-DTPA moves with the solvent front. The strips are cut in halves and counted in the gamma counter equipped with the multichannel analyzer using channels 72-110 for $^{225}$Ac to exclude its daughters.

Purification: An exemplary radiolabeled targeting agent, such as $^{225}$Ac-chelator-conjugated antibody, is purified either on PD10 columns pre-blocked with 1% I or on Vivaspin centrifugal concentrators with a 50 kDa MW cut-off with 2×1.5 mL washes, 3 min per spin. HPLC analyses of the $^{225}$Ac-chelator-conjugated antibody after purification is conducted using a Waters HPLC system equipped with flow-through Waters UV and Bioscan Radiation detectors, using a TSK3000SW XL column eluted with PBS at pH=7.4 and a flow rate of 1 ml/min.

With respect to any of the bifunctional chelator embodiments disclosed herein that include a cyclohexyl group adjacent to DOTA or a different chelator moiety, the invention also provides corresponding embodiments in which the cyclohexyl group is replaced by a benzyl group. Similarly, with respect to any of the bifunctional chelator embodiments disclosed herein that include a benzyl group adjacent to DOTA or a different chelator moiety, the invention also provides corresponding embodiments in which the benzyl group is replaced by a cyclohexyl group.

Example 2: Solid Phase Synthesis of Bifunctional Chelator Compounds

Synthesis of the Bifunctional Chelator Compound A with PEG3

Figure 19:
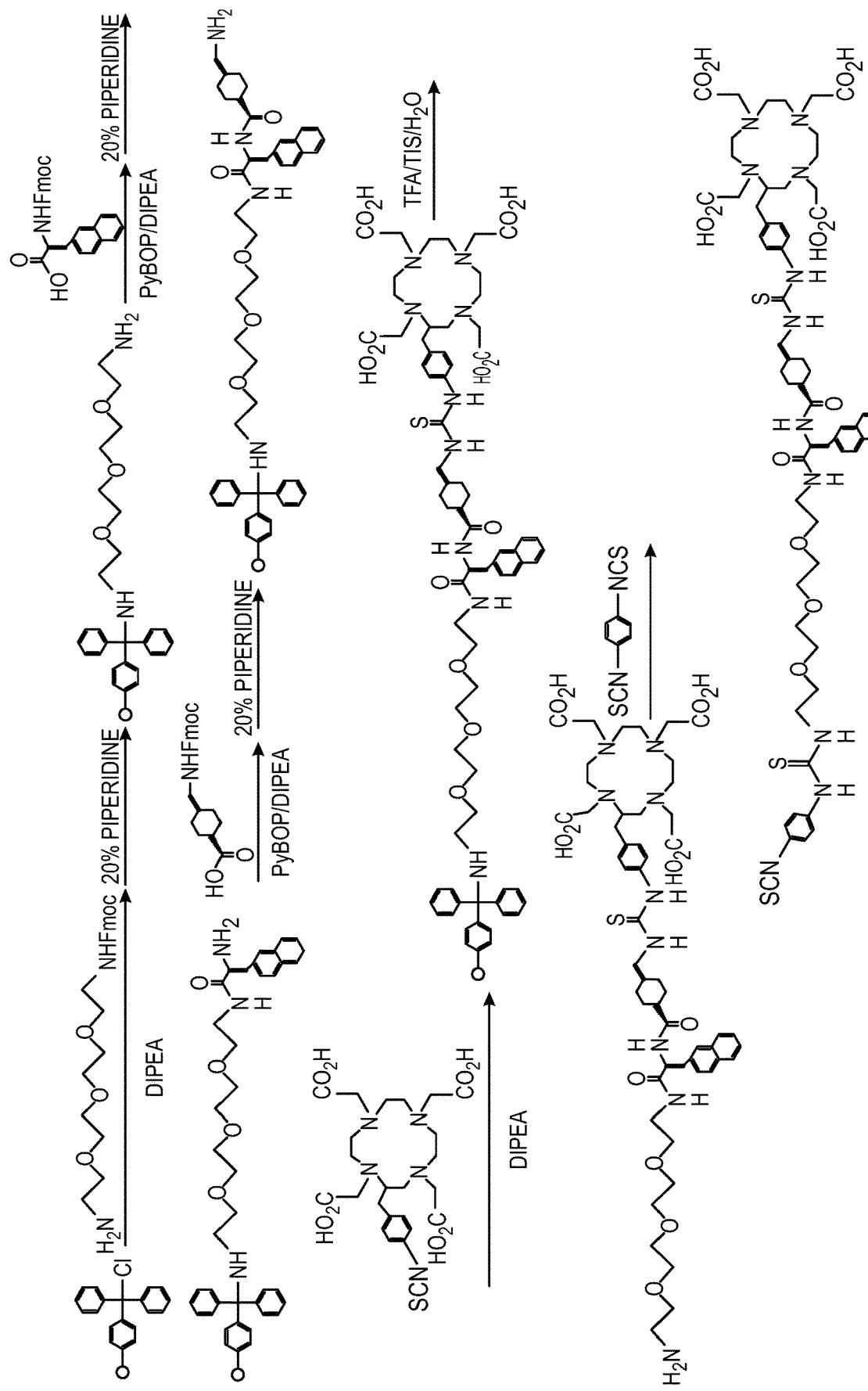
FIG. 19 shows a synthetic scheme of the present disclosure for the synthesis of a bifunctional chelator compound of Formula A shown in FIG. 1.

The synthesis was performed as shown in FIG. 19, wherein the starting materials and commercial sources thereof are described in Table 1.

TABLE 1

| Name | Structure | Supplier | Catalog No. |
|---|---|---|---|
| p-SCN-Bn-DOTA | 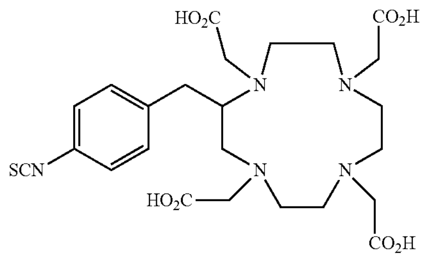 | Macrocyclics, Inc. (Plano, TX USA) | B-205 |
| Trityl chloride resin | 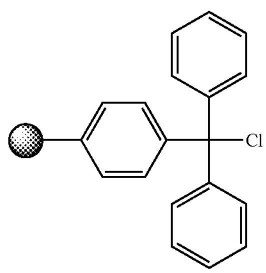 [SMILES: Cc1ccc(C(Cl)(c2ccccc2)c2ccccc2)cc1] | Chem-Impex Intl. Inc. (Wood Dale, IL USA) | 03902 |
| Fmoc-Amino-PEG3-Amine | 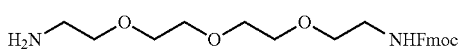 | Conju-Probe, LLC (San Diego, CA USA) | CP-1043 |
| Fmoc-3-(2-naphthyl)-alanine | 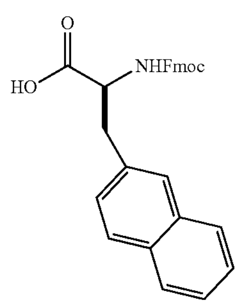 | Chem-Impex | 02588 |
| Fmoc-aminomethyl-cyclohexane carboxylic acid | 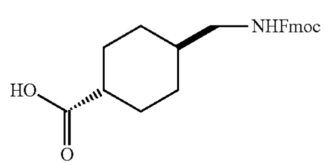 | Sigma-Aldrich (Burlington, MA USA; "Sigma") | 58446 |
| p-phenylene diisothiocyanate | 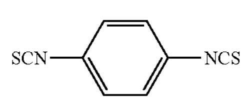 | Sigma | 258555 |

Synthesis of the Bifunctional Chelator Compound A

Figure 20:
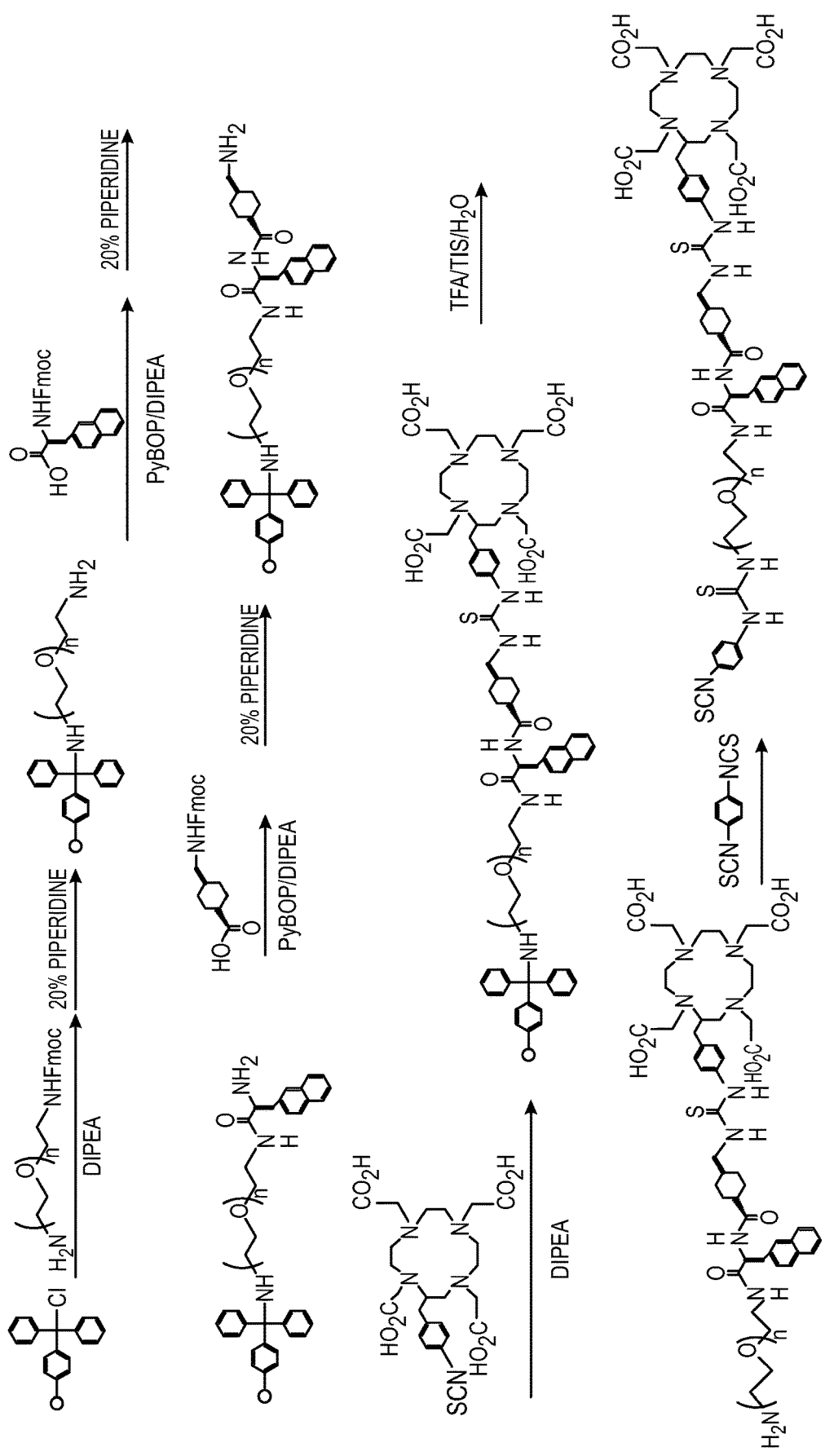
FIG. 20 shows a synthetic scheme of the present disclosure for the synthesis of a bifunctional chelator compound of Formula A shown in FIG. 1.

The synthesis was performed as shown in FIG. 20, wherein the starting materials are described in Table 2.

TABLE 2

| Name | Structure | Supplier | Catalog No. |
| --- | --- | --- | --- |
| p-SCN-Bn-DOTA | 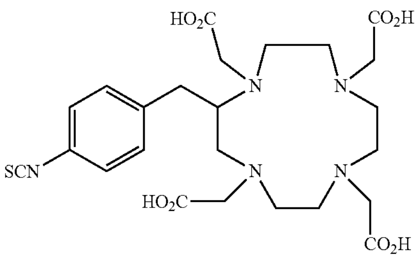 | Macrocyclics | B-205 |
| Trityl chloride resin | 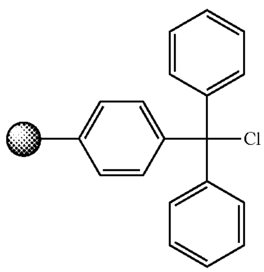 [SMILES: Cc1ccc(C(Cl)(c2ccccc2)c2ccccc2)cc1] | Chem-Impex | 03902 |
| Fmoc-NH-PEG-NH2, 10k | 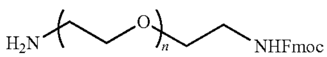 | BioPharma PEG Scientific Inc. (Watertown, MA USA) | HE069005-10K |
| Fmoc-3-(2-naphthyl)-alanine | 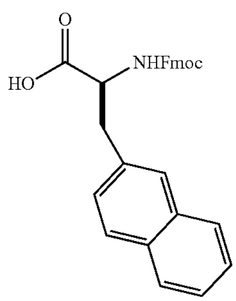 | Chem-Impex | 02588 |
| Fmoc-aminomethyl-cyclohexane carboxylic acid | 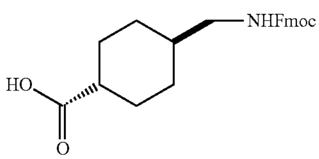 | Sigma | 58446 |
| p-phenylene diisothiocyanate | 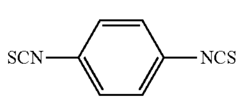 | Sigma | 258555 |

Synthesis of the Bifunctional Chelator Compound B

Figure 21:
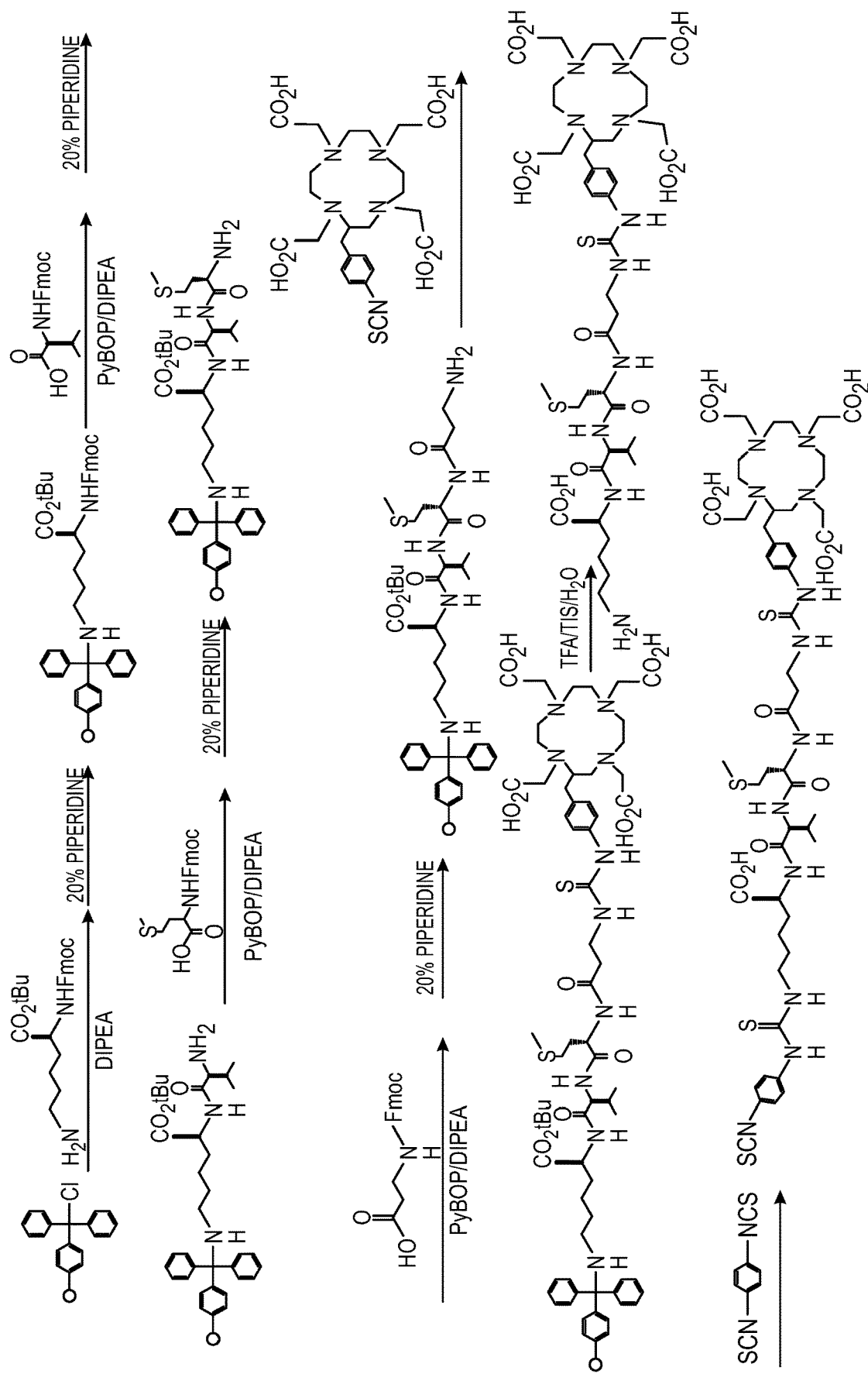
FIG. 21 shows a synthetic scheme of the present disclosure for the synthesis of a bifunctional chelator compound of Formula B shown in FIG. 2.

The synthesis was performed as shown in FIG. 21, wherein the starting materials are described in Table 3.

TABLE 3

| Name | Structure | Supplier | Catalog No. |
|---|---|---|---|
| Trityl chloride resin | 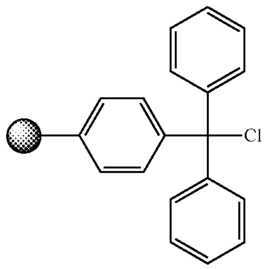 [SMILES: Cc1ccc(C(Cl)(c2ccccc2)c2ccccc2)cc1] | Chem-Impex | 03902 |
| p-SCN-Bn-DOTA | 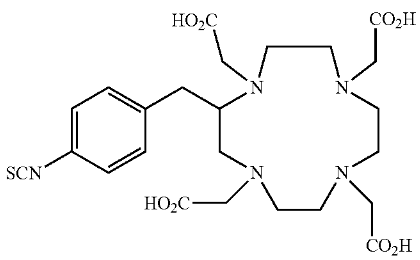 | Macrocyclics | B-205 |
| Fmoc-Lys-OtBu | 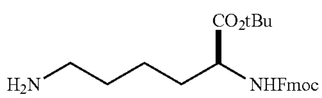 | Chem-Impex | 33496 |
| Fmoc-Val-OH | 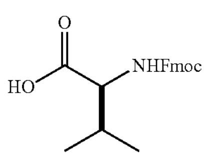 | Sigma | 47638 |
| Fmoc-Met-OH | 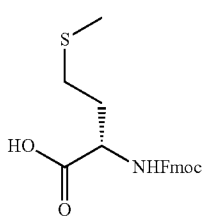 | Sigma | 47634 |
| Fmoc-beta-Ala-OH | 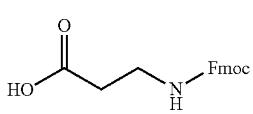 | Sigma | 47587 |
| p-phenylene diisothiocyanate | 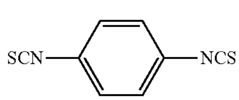 | Sigma | 258555 |

Figure 18:
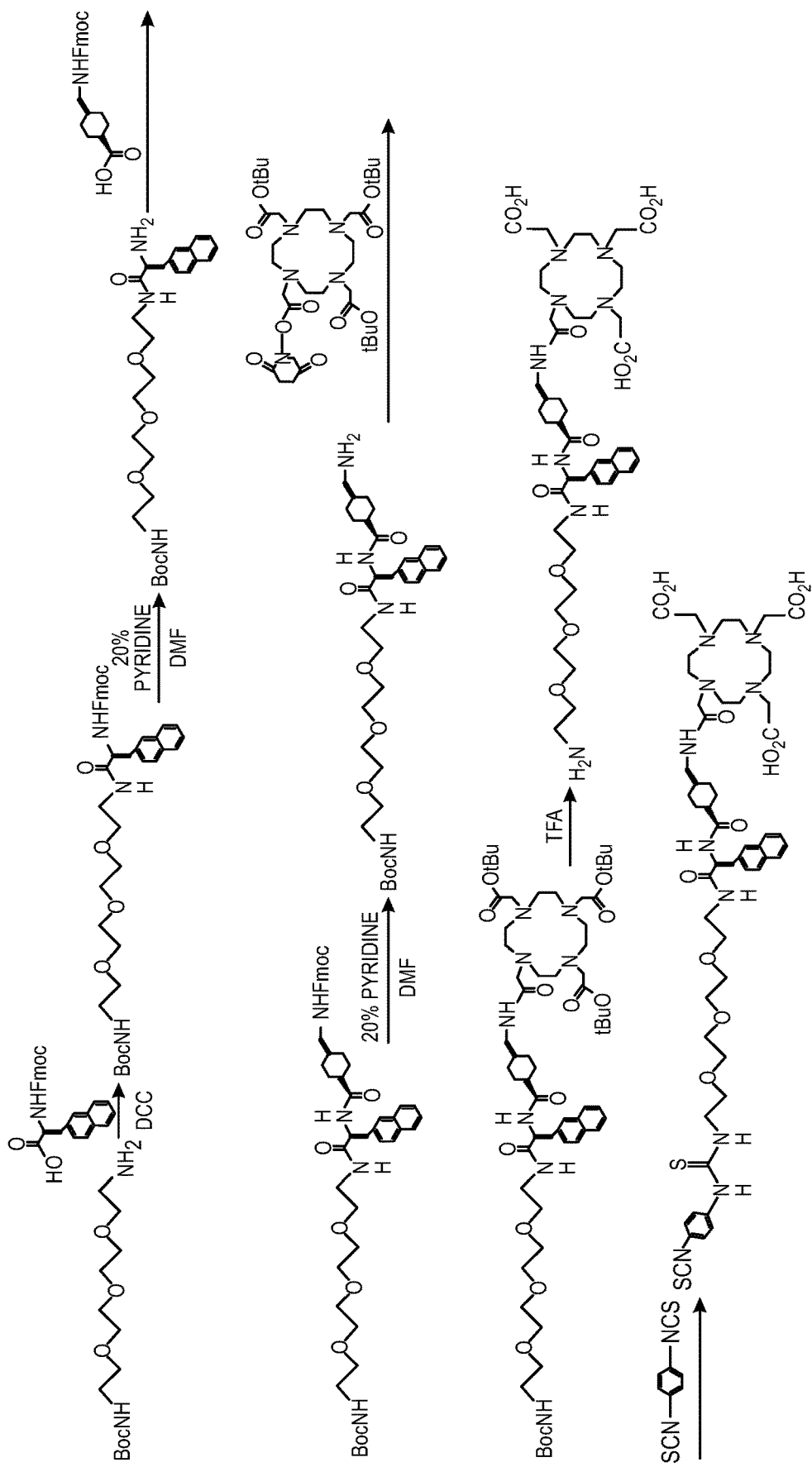
FIG. 18 shows a synthetic scheme of the present disclosure for the synthesis of the bifunctional chelator compound of Formula C shown in FIG. 3.

Synthesis of the Bifunctional Chelator Compound C
The synthesis was performed as shown in FIG. 18.

```
                            SEQUENCE LISTING

Sequence total quantity: 139
SEQ ID NO: 1            moltype = AA  length = 11
FEATURE                 Location/Qualifiers
REGION                  1..11
                        note = Antibody component sequence
source                  1..11
                        mol_type = protein
                        organism = synthetic construct
SEQUENCE: 1
SASQDISNYL N                                                            11

SEQ ID NO: 2            moltype = AA  length = 7
FEATURE                 Location/Qualifiers
REGION                  1..7
                        note = Antibody component sequence
source                  1..7
                        mol_type = protein
                        organism = synthetic construct
SEQUENCE: 2
DTSILHL                                                                 7

SEQ ID NO: 3            moltype = AA  length = 9
FEATURE                 Location/Qualifiers
REGION                  1..9
                        note = Antibody component sequence
source                  1..9
                        mol_type = protein
                        organism = synthetic construct
SEQUENCE: 3
QQYSKFPRT                                                               9

SEQ ID NO: 4            moltype = AA  length = 5
FEATURE                 Location/Qualifiers
REGION                  1..5
                        note = Antibody component sequence
source                  1..5
                        mol_type = protein
                        organism = synthetic construct
SEQUENCE: 4
NYAMN                                                                   5

SEQ ID NO: 5            moltype = AA  length = 17
FEATURE                 Location/Qualifiers
REGION                  1..17
                        note = Antibody component sequence
source                  1..17
                        mol_type = protein
                        organism = synthetic construct
SEQUENCE: 5
WINTHTGDPT YADDFKG                                                      17

SEQ ID NO: 6            moltype = AA  length = 9
FEATURE                 Location/Qualifiers
REGION                  1..9
                        note = Antibody component sequence
source                  1..9
                        mol_type = protein
                        organism = synthetic construct
SEQUENCE: 6
TYGNYAMDY                                                               9

SEQ ID NO: 7            moltype = AA  length = 107
FEATURE                 Location/Qualifiers
REGION                  1..107
                        note = Antibody component sequence
source                  1..107
                        mol_type = protein
                        organism = synthetic construct
SEQUENCE: 7
DIQMTQTTSS LSASLGDRVT ISCSASQDIS NYLNWYQQKP DGTVKLLIYD TSILHLGVPS  60
RFSGSGSGTD YSLTISNLEP EDIATYYCQQ YSKFPRTFGG GTTLEIK               107

SEQ ID NO: 8            moltype = AA  length = 191
FEATURE                 Location/Qualifiers
REGION                  1..191
```

```
                        note = Antibody component sequence
source                  1..191
                        mol_type = protein
                        organism = synthetic construct
SEQUENCE: 8
QIQLVQSGPE LKKPGETVKV SCKASGYMFT NYAMNWVKQA PEKGLKWMGW INTHTGDPTY    60
ADDFKGRIAF SLETSASTAY LQINNLKNED TATYFCVRTY GNYAMDYWGQ GTSVTVSSAK   120
TTAPSVYPLA PVCGDTTGSS VTLGCLVKGY FPEPVTLTWN SGSLSSGVHT FPAVLQSDLY   180
TLSSSVTVTS S                                                       191

SEQ ID NO: 9            moltype = AA   length = 109
FEATURE                 Location/Qualifiers
REGION                  1..109
                        note = Antibody component sequence
source                  1..109
                        mol_type = protein
                        organism = synthetic construct
SEQUENCE: 9
DIQLTQSPSF LSASVGDRVT ITCRASQGIT SYLAWYQQKP GKAPKLLIYA ASALQSGVPS    60
RFSGRGSGTE FTLTISSLQP EDFATYYCQQ VNRGAAITFG HGTRLDIKR               109

SEQ ID NO: 10           moltype = AA   length = 120
FEATURE                 Location/Qualifiers
REGION                  1..120
                        note = Antibody component sequence
VARIANT                 20
                        note = misc_feature - Xaa can be any naturally occurring
                         amino acid
VARIANT                 35
                        note = misc_feature - Xaa can be any naturally occurring
                         amino acid
source                  1..120
                        mol_type = protein
                        organism = synthetic construct
SEQUENCE: 10
QVQLVQSGAE VKKPGSSVRX SCRASGGSST TYAFXWVRQA PGQGLEWMGG IVPIFGTLKY    60
AQKFQDRVTL TADKSTGTAY MELNSLRLDD TAVYYCARAI QLEGRPFDHW GQGTQVTVSA   120

SEQ ID NO: 11           moltype = AA   length = 11
FEATURE                 Location/Qualifiers
REGION                  1..11
                        note = Antibody component sequence
source                  1..11
                        mol_type = protein
                        organism = synthetic construct
SEQUENCE: 11
QASQDIGNNL I                                                        11

SEQ ID NO: 12           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 12
YATNLAN                                                             7

SEQ ID NO: 13           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 13
QQWSSNP                                                             7

SEQ ID NO: 14           moltype = AA   length = 5
FEATURE                 Location/Qualifiers
REGION                  1..5
                        note = Antibody component sequence
source                  1..5
                        mol_type = protein
                        organism = synthetic construct
SEQUENCE: 14
NYYMS                                                               5

SEQ ID NO: 15           moltype = AA   length = 17
```

```
FEATURE                  Location/Qualifiers
REGION                   1..17
                         note = Antibody component sequence
source                   1..17
                         mol_type = protein
                         organism = synthetic construct
SEQUENCE: 15
NIYGGNGGTG YNQKFKG                                                          17

SEQ ID NO: 16            moltype = AA   length = 8
FEATURE                  Location/Qualifiers
REGION                   1..8
                         note = Antibody component sequence
source                   1..8
                         mol_type = protein
                         organism = synthetic construct
SEQUENCE: 16
GDLYAMDY                                                                     8

SEQ ID NO: 17            moltype = AA   length = 98
FEATURE                  Location/Qualifiers
REGION                   1..98
                         note = Antibody component sequence
source                   1..98
                         mol_type = protein
                         organism = synthetic construct
SEQUENCE: 17
VLTQSPSSMS ASLGDRVTIT CQASQDIGNN LIWFQQKPGK SPRPMIYYAT NLANGVPSRF            60
SGSGSGTSYS LTISSMEAED AATYYCQQWS SNPYTFGG                                    98

SEQ ID NO: 18            moltype = AA   length = 106
FEATURE                  Location/Qualifiers
REGION                   1..106
                         note = Antibody component sequence
source                   1..106
                         mol_type = protein
                         organism = synthetic construct
SEQUENCE: 18
AELVKPGASV KLSCKTSGYT FSNYYMSWLK QMPGQNIEWI GNIYGGNGGT GYNQKFKGKA            60
TLTVDKSSST AYMQLSSLTS EDSAVYFCAR GDLYAMDYWG QGTTVT                          106

SEQ ID NO: 19            moltype = AA   length = 245
FEATURE                  Location/Qualifiers
REGION                   1..245
                         note = Antibody component sequence
source                   1..245
                         mol_type = protein
                         organism = synthetic construct
SEQUENCE: 19
MAQVQLQQSG AELVKPGASV KLSCKTSGYT FSNYYMSWLK QMPGQNIEWI GNIYGGNGGT            60
GYNQKFKGKA TLTVDKSSST AYMQLSSLTS EDSAVYFCAR GDLYAMDYWG QGTTVTVSSG           120
GGGSGGGGSG GGGSDIVLTQ SPSSMSASLG DRVTITCQAS QDIGNNLIWF QQKPGKSPRP           180
MIYYATNLAN GVPSRFSGSG SGTSYSLTIS SMEAEDAATY YCQQWSSNPY TFGGGTKLEI           240
KRAAA                                                                      245

SEQ ID NO: 20            moltype = AA   length = 11
FEATURE                  Location/Qualifiers
REGION                   1..11
                         note = Antibody component sequence
source                   1..11
                         mol_type = protein
                         organism = synthetic construct
SEQUENCE: 20
RASQNIDTSI H                                                                11

SEQ ID NO: 21            moltype = AA   length = 7
FEATURE                  Location/Qualifiers
REGION                   1..7
                         note = Antibody component sequence
source                   1..7
                         mol_type = protein
                         organism = synthetic construct
SEQUENCE: 21
YASESIS                                                                      7

SEQ ID NO: 22            moltype = AA   length = 9
FEATURE                  Location/Qualifiers
REGION                   1..9
                         note = Antibody component sequence
```

```
source                    1..9
                          mol_type = protein
                          organism = synthetic construct
SEQUENCE: 22
QQSNYWPLT                                                                       9

SEQ ID NO: 23             moltype = AA  length = 5
FEATURE                   Location/Qualifiers
REGION                    1..5
                          note = Antibody component sequence
source                    1..5
                          mol_type = protein
                          organism = synthetic construct
SEQUENCE: 23
SYWMN                                                                           5

SEQ ID NO: 24             moltype = AA  length = 6
FEATURE                   Location/Qualifiers
REGION                    1..6
                          note = Antibody component sequence
source                    1..6
                          mol_type = protein
                          organism = synthetic construct
SEQUENCE: 24
GYSFTS                                                                          6

SEQ ID NO: 25             moltype = AA  length = 10
FEATURE                   Location/Qualifiers
REGION                    1..10
                          note = Antibody component sequence
source                    1..10
                          mol_type = protein
                          organism = synthetic construct
SEQUENCE: 25
GYSFTSYWMN                                                                     10

SEQ ID NO: 26             moltype = AA  length = 17
FEATURE                   Location/Qualifiers
REGION                    1..17
                          note = Antibody component sequence
source                    1..17
                          mol_type = protein
                          organism = synthetic construct
SEQUENCE: 26
MIHPSDSETR LNQKFKD                                                             17

SEQ ID NO: 27             moltype = AA  length = 10
FEATURE                   Location/Qualifiers
REGION                    1..10
                          note = Antibody component sequence
source                    1..10
                          mol_type = protein
                          organism = synthetic construct
SEQUENCE: 27
MIHPSDSETR                                                                     10

SEQ ID NO: 28             moltype = AA  length = 9
FEATURE                   Location/Qualifiers
REGION                    1..9
                          note = Antibody component sequence
source                    1..9
                          mol_type = protein
                          organism = synthetic construct
SEQUENCE: 28
EMGPYTLDY                                                                       9

SEQ ID NO: 29             moltype = AA  length = 127
FEATURE                   Location/Qualifiers
REGION                    1..127
                          note = Antibody component sequence
source                    1..127
                          mol_type = protein
                          organism = synthetic construct
SEQUENCE: 29
MSVPTQVLGL LLLWLTDARC DILLTQSPAI LSVSPGARVS FSCRASQNID TSIHWYQQRT               60
NGSPRLLIKY ASESISGIPS RFSGSGSGTD FTLSINSVES EDIADYYCQQ SNYWPLTFGA              120
GTKLELK                                                                       127

SEQ ID NO: 30             moltype = AA  length = 141
```

```
FEATURE              Location/Qualifiers
REGION               1..141
                     note = Antibody component sequence
source               1..141
                     mol_type = protein
                     organism = synthetic construct
SEQUENCE: 30
MEWSWVFLFF LSVTTGVHSQ VQLQQPGAEL VRPGASVKLS CKASGYSFTS YWMNWMKQRP    60
GQGLEWIGMI HPSDSETRLN QKFKDKATLT VDKSSSTAYM QLNSPTSEDS AVYYCAREMG   120
PYTLDYWGQG TSVTVSSAST K                                             141

SEQ ID NO: 31        moltype = AA  length = 16
FEATURE              Location/Qualifiers
REGION               1..16
                     note = Antibody component sequence
source               1..16
                     mol_type = protein
                     organism = synthetic construct
SEQUENCE: 31
KSSQSLLNSS NQKNYL                                                    16

SEQ ID NO: 32        moltype = AA  length = 7
FEATURE              Location/Qualifiers
REGION               1..7
                     note = Antibody component sequence
source               1..7
                     mol_type = protein
                     organism = synthetic construct
SEQUENCE: 32
FASTRES                                                               7

SEQ ID NO: 33        moltype = AA  length = 9
FEATURE              Location/Qualifiers
REGION               1..9
                     note = Antibody component sequence
source               1..9
                     mol_type = protein
                     organism = synthetic construct
SEQUENCE: 33
QQHYSTPPT                                                             9

SEQ ID NO: 34        moltype = AA  length = 5
FEATURE              Location/Qualifiers
REGION               1..5
                     note = Antibody component sequence
source               1..5
                     mol_type = protein
                     organism = synthetic construct
SEQUENCE: 34
RYAMS                                                                 5

SEQ ID NO: 35        moltype = AA  length = 6
FEATURE              Location/Qualifiers
REGION               1..6
                     note = Antibody component sequence
source               1..6
                     mol_type = protein
                     organism = synthetic construct
SEQUENCE: 35
GFTFSR                                                                6

SEQ ID NO: 36        moltype = AA  length = 10
FEATURE              Location/Qualifiers
REGION               1..10
                     note = Antibody component sequence
source               1..10
                     mol_type = protein
                     organism = synthetic construct
SEQUENCE: 36
GFTFSRYAMS                                                           10

SEQ ID NO: 37        moltype = AA  length = 15
FEATURE              Location/Qualifiers
REGION               1..15
                     note = Antibody component sequence
source               1..15
                     mol_type = protein
                     organism = synthetic construct
SEQUENCE: 37
```

```
TIFSGGSYTY YPDSV                                                    15

SEQ ID NO: 38            moltype = AA  length = 8
FEATURE                  Location/Qualifiers
REGION                   1..8
                         note = Antibody component sequence
source                   1..8
                         mol_type = protein
                         organism = synthetic construct
SEQUENCE: 38
TIFSGGSY                                                             8

SEQ ID NO: 39            moltype = AA  length = 9
FEATURE                  Location/Qualifiers
REGION                   1..9
                         note = Antibody component sequence
source                   1..9
                         mol_type = protein
                         organism = synthetic construct
SEQUENCE: 39
PNWERTFDY                                                            9

SEQ ID NO: 40            moltype = AA  length = 133
FEATURE                  Location/Qualifiers
REGION                   1..133
                         note = Antibody component sequence
source                   1..133
                         mol_type = protein
                         organism = synthetic construct
SEQUENCE: 40
MESQTQVLMF LLLWVSGACT DIVMTQSPSS LAMSVGQKVT MSCKSSQSLL NSSNQKNYLA   60
WYQQKPGQSP KLLVYFASTR ESGVPDRFMG SGSGTDFTLT ISSVQAEDLA DYFCQQHYST  120
PPTFGGGTKL EIK                                                     133

SEQ ID NO: 41            moltype = AA  length = 133
FEATURE                  Location/Qualifiers
REGION                   1..133
                         note = Antibody component sequence
source                   1..133
                         mol_type = protein
                         organism = synthetic construct
SEQUENCE: 41
MRVLILLWLF TAFPGLLSDV QLQESGPGLV KPSQSLSLTC TVTGYSITSD YAWNWIRQFP   60
GNKLEWMGFV SYSGTTKYNP SLKSRISITR DTSENQFFLQ LNSVTEDTA  TYYCARGYGF  120
DYWGQGTTLT VSS                                                     133

SEQ ID NO: 42            moltype = AA  length = 38
FEATURE                  Location/Qualifiers
REGION                   1..38
                         note = Antibody component sequence
source                   1..38
                         mol_type = protein
                         organism = synthetic construct
SEQUENCE: 42
EIILTQSPTT MAASPGEKIT ITCSASSSIS SHYLHWYQ                            38

SEQ ID NO: 43            moltype = AA  length = 40
FEATURE                  Location/Qualifiers
REGION                   1..40
                         note = Antibody component sequence
source                   1..40
                         mol_type = protein
                         organism = synthetic construct
SEQUENCE: 43
QKSGFSPKLL YRTSNLASGV PARESGSGSG TSYSLTIGTM                          40

SEQ ID NO: 44            moltype = AA  length = 29
FEATURE                  Location/Qualifiers
REGION                   1..29
                         note = Antibody component sequence
source                   1..29
                         mol_type = protein
                         organism = synthetic construct
SEQUENCE: 44
EAEDVATYYC QQGSSLPLTF GAGTKVEIK                                      29

SEQ ID NO: 45            moltype = AA  length = 41
FEATURE                  Location/Qualifiers
REGION                   1..41
```

```
                         note = Antibody component sequence
source                   1..41
                         mol_type = protein
                         organism = synthetic construct
SEQUENCE: 45
EIQLQQSGPE LVKPGASVKV SCKASGYAFT SQNIYWVKQS H                       41

SEQ ID NO: 46            moltype = AA  length = 40
FEATURE                  Location/Qualifiers
REGION                   1..40
                         note = Antibody component sequence
source                   1..40
                         mol_type = protein
                         organism = synthetic construct
SEQUENCE: 46
GKSLEWIGYE PYNVVPMYNP KFKGKATLTV DKSSSSAYIH                         40

SEQ ID NO: 47            moltype = AA  length = 35
FEATURE                  Location/Qualifiers
REGION                   1..35
                         note = Antibody component sequence
source                   1..35
                         mol_type = protein
                         organism = synthetic construct
SEQUENCE: 47
LNSLTSEDSA IYYCARSGSS NFDYWGQGTT LTVSS                              35

SEQ ID NO: 48            moltype = AA  length = 330
FEATURE                  Location/Qualifiers
source                   1..330
                         mol_type = protein
                         organism = Homo sapiens
SEQUENCE: 48
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 49            moltype = AA  length = 216
FEATURE                  Location/Qualifiers
source                   1..216
                         mol_type = protein
                         organism = Homo sapiens
SEQUENCE: 49
MGWIRGRRSR HSWEMSEFHN YNLDLKKSDF STRWQKQRCP VVKSKCRENA SPFFFCCFIA    60
VAMGIRFIIM VTIWSAVFLN SLFNQEVQIP LTESYCGPCP KNWICYKNNC YQFFDESKNW   120
YESQASCMSQ NASLLKVYSK EDQDLLKLVK SYHWMGLVHI PTNGSWQWED GSILSPNLLT   180
IIEMQKGDCA LYASSFKGYI ENCSTPNTYI CMQRTV                            216

SEQ ID NO: 50            moltype = AA  length = 4
FEATURE                  Location/Qualifiers
REGION                   1..4
                         note = fusion protein linker sequence
source                   1..4
                         mol_type = protein
                         organism = synthetic construct
SEQUENCE: 50
IEGR                                                                 4

SEQ ID NO: 51            moltype =    length =
SEQUENCE: 51
000

SEQ ID NO: 52            moltype = AA  length = 345
FEATURE                  Location/Qualifiers
REGION                   1..345
                         note = Fusion protein
source                   1..345
                         mol_type = protein
                         organism = synthetic construct
SEQUENCE: 52
EEELQVIQPD KSVSVAAGES AILHCTVTSL IPVGPIQWFR GAGPARELIY NQKEGHFPRV    60
TTVSESTKRE NMDFSISISN ITPADAGTYY CVKFRKGSPD TEFKSGAGTE LSVRAKPSDK   120
THTCPPCPAP ELLGGPSVFL FPPKPKDTLM ISRTPEVTCV VVDVSHEDPE VKFNWYVDGV   180
EVHNAKTKPR EEQYNSTYRV VSVLTVLHQD WLNGKEYKCK VSNKALPAPI EKTISKAKGQ   240
PREPQVYTLP PSRDELTKNQ VSLTCLVKGF YPSDIAVEWE SNGQPENNYK TTPPVLDSDG   300
SFFLYSKLTV DKSRWQQGNV FSCSVMHEAL HNHYTQKSLS LSPGK                  345
```

```
SEQ ID NO: 53              moltype = AA   length = 345
FEATURE                    Location/Qualifiers
REGION                     1..345
                           note = Fusion protein
source                     1..345
                           mol_type = protein
                           organism = synthetic construct
SEQUENCE: 53
EEELQVIQPD KSVSVAAGES AILHCTVTSL IPVGPIQWFR GAGPARELIY NQKEGHFPRV    60
TTVSESTKRE NMDFSISISN ITPADAGTYY CVKFPRKGSPD TEFKSGAGTE LSVRAKPSDK  120
THTCPPCPAP ELLGGPSVFL FPPKPKDTLM ISRTPEVTCV VVDVSHEDPE VKFNWYVDGV  180
EVHNAKTKPR EEQYNSTYRV VSVLTVLHQD WLNGKEYKCK VSNKALPAPI EKTISKAKGQ  240
PREPQVYTLP PSRDELTKNQ VSLTCLVKGF YPSDIAVEWE SNGQPENNYK TTPPVLDSDG  300
SFFLYSKLTV DKSRWQQGNV FSCSVMHEAL HNHYTQKSLS LSPGK                  345

SEQ ID NO: 54              moltype = AA   length = 347
FEATURE                    Location/Qualifiers
REGION                     1..347
                           note = Fusion protein
source                     1..347
                           mol_type = protein
                           organism = synthetic construct
SEQUENCE: 54
EEELQVIQPD KSVSVAAGES AILHCTVTSL IPVGPIQWFR GAGPARELIY NQKEGHFPRV    60
TTVSESTKRE NMDFSISISN ITPADAGTYY CVKFPRKGSPD TEFKSGAGTE LSVRAKPSES  120
KYGPPCPPCP APEFLGGPSV FLFPPKPKDT LMISRTPEVT CVVVDVSQED PEVQFNWYVD  180
GVEVHNAKTK PREEQFNSTY RVVSVLTVLH QDWLNGKEYK CKVSNKGLPS SIEKTISKAK  240
GQPREPQVYT LPPSQEEMTK NQVSLTCLVK GFYPSDIAVE WESNGQPENN YKTTPPVLDS  300
DGSFFLYSRL TVDKSRWQEG NVFSCSVMHE ALHNHYTQKS LSLSLGK                347

SEQ ID NO: 55              moltype = DNA   length = 25
FEATURE                    Location/Qualifiers
misc_feature               1..25
                           note = Morpholino
source                     1..25
                           mol_type = other DNA
                           organism = synthetic construct
SEQUENCE: 55
cgtcacaggc aggacccact gccca                                         25

SEQ ID NO: 56              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 56
DYAMS                                                                5

SEQ ID NO: 57              moltype = AA   length = 17
FEATURE                    Location/Qualifiers
REGION                     1..17
                           note = Description of Artificial Sequence: Synthetic peptide
source                     1..17
                           mol_type = protein
                           organism = synthetic construct
SEQUENCE: 57
TISDGGTYTY YPDSVKG                                                  17

SEQ ID NO: 58              moltype = AA   length = 10
FEATURE                    Location/Qualifiers
REGION                     1..10
                           note = Description of Artificial Sequence: Synthetic peptide
source                     1..10
                           mol_type = protein
                           organism = synthetic construct
SEQUENCE: 58
EWGDYDGFDY                                                          10

SEQ ID NO: 59              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 59
```

RASQEISGYL S                                                               11

SEQ ID NO: 60           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 60
AASTLDS                                                                    7

SEQ ID NO: 61           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 61
LQYDSYPYT                                                                  9

SEQ ID NO: 62           moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 62
QVQLVESGGG LVKPGGSLRL SCAASGFTFS DYAMSWIRQA PGKGLEWVST ISDGGTYTYY    60
PDSVKGRFTI SRDNAKNSLY LQMNSLRAED TAVYYCAREW GDYDGFDYWG QGTLVTVSS    119

SEQ ID NO: 63           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 63
DIQMTQSPSS LSASVGDRVT ITCRASQEIS GYLSWYQQKP GKAPKRLIYA ASTLDSGVPS    60
RFSGSGSGTE FTLTISSLQP EDFATYYCLQ YDSYPYTFGQ GTKLEIK                 107

SEQ ID NO: 64           moltype = AA  length = 471
FEATURE                 Location/Qualifiers
REGION                  1..471
                        note = Description of Artificial Sequence: Synthetic
                         polypeptide
source                  1..471
                        mol_type = protein
                        organism = synthetic construct
SEQUENCE: 64
MDMRVPAQLL GLLLLWLRGA RCQVQLVESG GGLVKPGGSL RLSCAASGFT FSDYAMSWIR    60
QAPGKGLEWV STISDGGTYT YYPDSVKGRF TISRDNAKNS LYLQMNSLRA EDTAVYYCAR   120
EWGDYDGFDY WGQGTLVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471

SEQ ID NO: 65           moltype = AA  length = 236
FEATURE                 Location/Qualifiers
REGION                  1..236
                        note = Description of Artificial Sequence: Synthetic
                         polypeptide
source                  1..236
                        mol_type = protein
                        organism = synthetic construct
SEQUENCE: 65
MDMRVPAQLL GLLLLWLRGA RCDIQMTQSP SSLSASVGDR VTITCRASQE ISGYLSWYQQ    60
KPGKAPKRLI YAASTLDSGV PSRFSGSGSG TEFTLTISSL QPEDFATYYC LQYDSYPYTF   120
GQGTKLEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 66           moltype = AA  length = 451

```
FEATURE                Location/Qualifiers
REGION                 1..451
                       note = mAb
source                 1..451
                       mol_type = protein
                       organism = synthetic construct
SEQUENCE: 66
QVQLQQSGSE LKKPGASVKV SCKASGYTFT NYGMNWVKQA PGQGLKWMGW INTYTGEPTY   60
TDDFKGRFAF SLDTSVSTAY LQISSLKADD TAVYFCARGG FGSSYWYFDV WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 67          moltype = AA   length = 121
FEATURE                Location/Qualifiers
REGION                 1..121
                       note = mAb
source                 1..121
                       mol_type = protein
                       organism = synthetic construct
SEQUENCE: 67
QVQLQQSGSE LKKPGASVKV SCKASGYTFT NYGMNWVKQA PGQGLKWMGW INTYTGEPTY   60
TDDFKGRFAF SLDTSVSTAY LQISSLKADD TAVYFCARGG FGSSYWYFDV WGQGSLVTVS  120
S                                                                  121

SEQ ID NO: 68          moltype = AA   length = 5
FEATURE                Location/Qualifiers
REGION                 1..5
                       note = mAb
source                 1..5
                       mol_type = protein
                       organism = synthetic construct
SEQUENCE: 68
NYGMN                                                                5

SEQ ID NO: 69          moltype = AA   length = 17
FEATURE                Location/Qualifiers
REGION                 1..17
                       note = mAb
source                 1..17
                       mol_type = protein
                       organism = synthetic construct
SEQUENCE: 69
WINTYTGEPT YTDDFKG                                                  17

SEQ ID NO: 70          moltype = AA   length = 12
FEATURE                Location/Qualifiers
REGION                 1..12
                       note = mAb
source                 1..12
                       mol_type = protein
                       organism = synthetic construct
SEQUENCE: 70
GGFGSSYWYF DV                                                       12

SEQ ID NO: 71          moltype = AA   length = 214
FEATURE                Location/Qualifiers
REGION                 1..214
                       note = mAb
source                 1..214
                       mol_type = protein
                       organism = synthetic construct
SEQUENCE: 71
DIQLTQSPSS LSASVGDRVS ITCKASQDVS IAVAWYQQKP GKAPKLLIYS ASYRYTGVPD   60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 72          moltype = AA   length = 110
FEATURE                Location/Qualifiers
REGION                 1..110
                       note = mAb
source                 1..110
                       mol_type = protein
                       organism = synthetic construct
SEQUENCE: 72
```

```
DIQLTQSPSS LSASVGDRVS ITCKASQDVS IAVAWYQQKP GKAPKLLIYS ASYRYTGVPD   60
RFSGSGSGTD FTLTISSLQP EDFAVYYCQQ HYITPLTFGA GTKVEIKRTV            110

SEQ ID NO: 73           moltype = AA  length = 11
FEATURE                 Location/Qualifiers
REGION                  1..11
                        note = mAb
source                  1..11
                        mol_type = protein
                        organism = synthetic construct
SEQUENCE: 73
KASQDVSIAV A                                                       11

SEQ ID NO: 74           moltype = AA  length = 7
FEATURE                 Location/Qualifiers
REGION                  1..7
                        note = mAb
source                  1..7
                        mol_type = protein
                        organism = synthetic construct
SEQUENCE: 74
SASYRYT                                                             7

SEQ ID NO: 75           moltype = AA  length = 9
FEATURE                 Location/Qualifiers
REGION                  1..9
                        note = mAb
source                  1..9
                        mol_type = protein
                        organism = synthetic construct
SEQUENCE: 75
QQHYITPLT                                                           9

SEQ ID NO: 76           moltype = AA  length = 451
FEATURE                 Location/Qualifiers
REGION                  1..451
                        note = mAb
source                  1..451
                        mol_type = protein
                        organism = synthetic construct
SEQUENCE: 76
QVQLVQSGAE VKKPGASVKV SCKASGYTFT TAGMQWVRQA PGQGLEWMGW INTHSGVPKY   60
AEDFKGRVTI SADTSTSTAY LQLSSLKSED TAVYYCARSG FGSSYWYFDV WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 77           moltype = AA  length = 121
FEATURE                 Location/Qualifiers
REGION                  1..121
                        note = mAb
source                  1..121
                        mol_type = protein
                        organism = synthetic construct
SEQUENCE: 77
QVQLVQSGAE VKKPGASVKV SCKASGYTFT TAGMQWVRQA PGQGLEWMGW INTHSGVPKY   60
AEDFKGRVTI SADTSTSTAY LQLSSLKSED TAVYYCARSG FGSSYWYFDV WGQGTLVTVS  120
S                                                                 121

SEQ ID NO: 78           moltype = AA  length = 5
FEATURE                 Location/Qualifiers
REGION                  1..5
                        note = mAb
source                  1..5
                        mol_type = protein
                        organism = synthetic construct
SEQUENCE: 78
TAGMQ                                                               5

SEQ ID NO: 79           moltype = AA  length = 17
FEATURE                 Location/Qualifiers
REGION                  1..17
                        note = mAb
source                  1..17
                        mol_type = protein
                        organism = synthetic construct
```

```
SEQUENCE: 79
WINTHSGVPK YAEDFKG                                                    17

SEQ ID NO: 80            moltype = AA  length = 12
FEATURE                  Location/Qualifiers
REGION                   1..12
                         note = mAb
source                   1..12
                         mol_type = protein
                         organism = synthetic construct
SEQUENCE: 80
SGFGSSYWYF DV                                                         12

SEQ ID NO: 81            moltype = AA  length = 214
FEATURE                  Location/Qualifiers
REGION                   1..214
                         note = mAb
source                   1..214
                         mol_type = protein
                         organism = synthetic construct
SEQUENCE: 81
DIQMTQSPSS LSASVGDRVT ITCKASQDVS TAVAWYQQKP GKAPKLLIYS ASYRYTGVPS      60
RFSGSGSGTD FTLTISSLQP EDFAVYYCQQ HYITPLTFGQ GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                 214

SEQ ID NO: 82            moltype = AA  length = 110
FEATURE                  Location/Qualifiers
REGION                   1..110
                         note = mAb
source                   1..110
                         mol_type = protein
                         organism = synthetic construct
SEQUENCE: 82
DIQMTQSPSS LSASVGDRVT ITCKASQDVS TAVAWYQQKP GKAPKLLIYS ASYRYTGVPS      60
RFSGSGSGTD FTLTISSLQP EDFAVYYCQQ HYITPLTFGQ GTKLEIKRTV                 110

SEQ ID NO: 83            moltype = AA  length = 11
FEATURE                  Location/Qualifiers
REGION                   1..11
                         note = mAb
source                   1..11
                         mol_type = protein
                         organism = synthetic construct
SEQUENCE: 83
KASQDVSTAV A                                                          11

SEQ ID NO: 84            moltype = AA  length = 7
FEATURE                  Location/Qualifiers
REGION                   1..7
                         note = mAb
source                   1..7
                         mol_type = protein
                         organism = synthetic construct
SEQUENCE: 84
SASYRYT                                                               7

SEQ ID NO: 85            moltype = AA  length = 9
FEATURE                  Location/Qualifiers
REGION                   1..9
                         note = mAb
source                   1..9
                         mol_type = protein
                         organism = synthetic construct
SEQUENCE: 85
QQHYITPLT                                                             9

SEQ ID NO: 86            moltype = AA  length = 450
FEATURE                  Location/Qualifiers
REGION                   1..450
                         note = Antibody heavy chain
source                   1..450
                         mol_type = protein
                         organism = synthetic construct
SEQUENCE: 86
EVQLVESGGG LVQPGGSLRL SCAASGFNIK DTYIHWVRQA PGKGLEWVAR IYPTNGYTRY      60
ADSVKGRFTI SADTSKNTAY LQMNSLRAED TAVYYCSRWG GDGFYAMDYW GQGTLVTVSS      120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS NTKVDKKVEP KSCDKTHTCP PCPAPELLGG      240
```

```
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 87           moltype = AA   length = 214
FEATURE                 Location/Qualifiers
REGION                  1..214
                        note = Antibody light chain
source                  1..214
                        mol_type = protein
                        organism = synthetic construct
SEQUENCE: 87
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 88           moltype = AA   length = 448
FEATURE                 Location/Qualifiers
REGION                  1..448
                        note = Antibody heavy chain
source                  1..448
                        mol_type = protein
                        organism = synthetic construct
SEQUENCE: 88
EVQLVESGGG LVQPGGSLRL SCAASGFTFT DYTMDWVRQA PGKGLEWVAD VNPNSGGSIY    60
NQRFKGRFTL SVDRSKNTLY LQMNSLRAED TAVYYCARNL GPSFYFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPG                                      448

SEQ ID NO: 89           moltype = AA   length = 214
FEATURE                 Location/Qualifiers
REGION                  1..214
                        note = Antibody light chain
source                  1..214
                        mol_type = protein
                        organism = synthetic construct
SEQUENCE: 89
DIQMTQSPSS LSASVGDRVT ITCKASQDVS IGVAWYQQKP GKAPKLLIYS ASYRYTGVPS    60
RFSGSGSGTD FTLTISSLQP EDFATYYCQQ YYIYPYTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 90           moltype = AA   length = 244
FEATURE                 Location/Qualifiers
source                  1..244
                        mol_type = protein
                        organism = Homo sapiens
SEQUENCE: 90
MAAAASPAFL LCLPLLHLLS GWSRAGWVDT HCLCYDFIIT PKSRPEPQWC EVQGLVDERP    60
FLHYDCVNHK AKAFASLGKK VNVTKTWEEQ TETLRDVVDF LKGQLLDIQV ENLIPIEPLT    120
LQARMSCEHE AHGHGRGSWQ FLFNGQKFLL FDSNNRKWTA LHPGAKKMTE KWEKNRDVTM    180
FFQKISLGDC KMWLEEFLMY WEQMLDPTKP PSLAPGTTQP KAMATTLSPW SLLIIFLCFI    240
LAGR                                                                244

SEQ ID NO: 91           moltype = AA   length = 233
FEATURE                 Location/Qualifiers
REGION                  1..233
                        note = Mutated Protein
source                  1..233
                        mol_type = protein
                        organism = synthetic construct
SEQUENCE: 91
SEKSEEINEK DLRKKSELQG TALGNLKQIY YYNSKAITSS EKSADQFLTN TLLFKGFFTG    60
HPWYNDLLVD LGSTAATSEY EGSSVDLYGA YYGYQCAGGT PNKTACMYGG VTLHDNNRLT    120
EEKKVPINLW IDGKQTTVPI DKVKTSKKEV TVQELDLQAR HYLHGKFGLY NSDSFGGKVQ    180
RGLIVFHSSE GSTVSYDLFD AQGQYPDTLL RIYRDNTTIS STSLSISLYL YTT           233

SEQ ID NO: 92           moltype = AA   length = 233
FEATURE                 Location/Qualifiers
REGION                  1..233
                        note = Mutated Protein
source                  1..233
                        mol_type = protein
```

```
                           organism = synthetic construct
SEQUENCE: 92
SEKSEEINEK DLRKKSELQG TALGNLKQIY YYNEKAKTEN KESHDQFLQH TILFKGFFTD    60
HSWYNDLLVD FDSKDIVDKY KGKKVDLYGA YYGYQCAGGT PNKTACMYGG VTLHDNNRLT   120
EEKKVPINLW LDGKQNTVPL ETVKTNKKNV TVQELDLQAR RYLQEKYNLY NSDVFDGKVQ   180
RGLIVFHTST EPSVNYDLFG AQGQYSNTLL RIYRDNKTIN SENMHIAIYL YTS          233

SEQ ID NO: 93              moltype = AA  length = 679
FEATURE                    Location/Qualifiers
REGION                     1..679
                           note = Conjugated Protein
REGION                     460..679
                           note = MISC_FEATURE - Light Chain
source                     1..679
                           mol_type = protein
                           organism = synthetic construct
SEQUENCE: 93
QVQLQQPGAE LVRPGASVKL SCKASGYTFT NYWINWVKQR PGQGLEWIGN IYPSYIYTNY    60
NQEFKDKVTL TVDESSSTAY MQLSSPTSED SAVYYCTRSP YGYDEYGLDY WGQGTSVTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDSGGPSEKS EEINEKDLRK   240
KSELQGTALG NLKQIYYYNE KAKTENKESH DQFLQHTILF KGFFTDHSWY NDLLVDFDSK   300
DIVDKYKGKK VDLYGAYYGY QCAGGTPNKT ACMYGGVTLH DNNRLTEEKK VPINLWLDGK   360
QNTVPLETVK TNKKNVTVQE LDLQARRYLQ EKYNLYNSDV FDGKVQRGLI VFHTSTEPSV   420
NYDLFGAQGQ YSNTLLRIYR DNKTINSENM HIDIYLYTSD IVMTQSPSSL TVTAGEKVTM   480
NCKSSQSLLN SRNQKNYLTW YQQKPGQPPK LLIYWASTRE SGVPDRFTGS GSGTDFTLTI   540
SSVQAEDLAV YYCQNDYVYP LTFGAGTKLE LKRADAAPTV SIFPPSSEQL TSGGASVVCF   600
LNNFYPKDIN VKWKIDGSER QNGVLNSWTD QDSKDSTYSM SSTLTLTKDE YERHNSYTCE   660
ATHKTSTSPI VKSFNRNES                                                679

SEQ ID NO: 94              moltype = AA  length = 672
FEATURE                    Location/Qualifiers
REGION                     1..672
                           note = Mutated and Conjugated Protein
REGION                     459..672
                           note = MISC_FEATURE - Light Chain
source                     1..672
                           mol_type = protein
                           organism = synthetic construct
SEQUENCE: 94
EVQLQQSGPD LVKPGASVKI SCKASGYSFT GYYMHWVKQS HGKSLEWIGR INPNNGVTLY    60
NQKFKDKAIL TVDKSSTTAY MELRSLTSED SAVYYCARST MITNYVMDYW GQVTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNEK AKTENKESHD QFLQHTILFK GFFTDHSWYN DLLVDFDSKD   300
IVDKYKGKKV DLYGAYYGYQ CAGGTPNKTA CMYGGVTLHD NNRLTEEKKV PINLWLDGKQ   360
NTVPLETVKT NKKNVTVQEL DLQARRYLQE KYNLYNSDVF DGKVQRGLIV FHTSTEPSVN   420
YDLFGAQGQY SNTLLRIYRD NKTINSENMH IAIYLYTSSI VMTQTPTSLL VSAGDRVTIT   480
CKASQSVSND VAWYQQKPGQ SPKLLISYTS SRYAGVPDRF SGSGSGTDFT LTISSVQAED   540
LAVYFCQQDY NSPPTFGGGT KLEIKRADAA PTVSIFPPSS EQLTSGGASV VCFLNNFYPK   600
DINVKWKIDG SERQNGVLNS WTDQDSKDST YSMSSTLTLT KDEYERHNSY TCEATHKTST   660
SPIVKSFNRN ES                                                       672

SEQ ID NO: 95              moltype = AA  length = 672
FEATURE                    Location/Qualifiers
REGION                     1..672
                           note = Mutated and Conjugated Protein
REGION                     459..672
                           note = MISC_FEATURE - Light Chain
source                     1..672
                           mol_type = protein
                           organism = synthetic construct
SEQUENCE: 95
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLTNTLLFK GFFTGHPWYN DLLVDLGSTA   300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFDAQGQY PDTLLRIYRD NTTISSTSLS ISLYLYTTSI VMTQTPTSLL VSAGDRVTIT   480
CKASQSVSND VAWYQQKPGQ SPKLLISYTS SRYAGVPDRF SGSGYGTDFT LTISSVQAED   540
AAVYFCQQDY NSPPTFGGGT KLEIKRADAA PTVSIFPPSS EQLTSGGASV VCFLNNFYPK   600
DINVKWKIDG SERQNGVLNS WTDQDSKDST YSMSSTLTLT KDEYERHNSY TCEATHKTST   660
SPIVKSFNRN ES                                                       672

SEQ ID NO: 96              moltype = AA  length = 458
FEATURE                    Location/Qualifiers
REGION                     1..458
```

```
                          note = Synthetic polypeptide
source                    1..458
                          mol_type = protein
                          organism = synthetic construct
SEQUENCE: 96
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLTNTLLFK GFFTGHPWYN DLLVDLGSTA   300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFDAQGQY PDTLLRIYRD NTTISSTSLS ISLYLYTT                          458

SEQ ID NO: 97             moltype = AA   length = 214
FEATURE                   Location/Qualifiers
REGION                    1..214
                          note = Synthetic polypeptide
source                    1..214
                          mol_type = protein
                          organism = synthetic construct
SEQUENCE: 97
SIVMTQTPTS LLVSAGDRVT ITCKASQSVS NDVAWYQQKP GQSPKLLISY TSSRYAGVPD    60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNES                              214

SEQ ID NO: 98             moltype = AA   length = 233
FEATURE                   Location/Qualifiers
REGION                    1..233
                          note = Mutated Protein
source                    1..233
                          mol_type = protein
                          organism = synthetic construct
SEQUENCE: 98
SEKSEEINEK DLRKKSELQG TALGNLKQIY YYNEKAITEN KESDDQFLEN TLLFKGFFTG    60
HPWYNDLLVD LGSKDATNKY KGKKVDLYGA YYGYQCAGGT PNKTACMYGG VTLHDNNRLT   120
EEKKVPINLW IDGKQTTVPI DKVKTSKKEV TVQELDLQAR HYLHGKFGLY NSDSFGGKVQ   180
RGLIVFHSSE GSTVSYDLFD AQGQYPDTLL RIYRDNKTIN SENLHIALYL YTT          233

SEQ ID NO: 99             moltype = AA   length = 215
FEATURE                   Location/Qualifiers
REGION                    1..215
                          note = Synthetic polypeptide
source                    1..215
                          mol_type = protein
                          organism = synthetic construct
SEQUENCE: 99
SIVMTQTPTS LLVSAGDRVT ITCKASQSVS NDVAWYQQKP GQSPKLLISY TSSRYAGVPD    60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESK                             215

SEQ ID NO: 100            moltype = AA   length = 215
FEATURE                   Location/Qualifiers
REGION                    1..215
                          note = Synthetic polypeptide
source                    1..215
                          mol_type = protein
                          organism = synthetic construct
SEQUENCE: 100
SIVMTQTPTS LLVSAGDRVT ITCKASQSVS NDVAWYQQKP GQSPKLLISY TSSRYAGVPD    60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESC                             215

SEQ ID NO: 101            moltype = AA   length = 216
FEATURE                   Location/Qualifiers
REGION                    1..216
                          note = Synthetic polypeptide
source                    1..216
                          mol_type = protein
                          organism = synthetic construct
SEQUENCE: 101
SIVMTQTPTS LLVSAGDRVT ITCKASQSVS NDVAWYQQKP GQSPKLLISY TSSRYAGVPD    60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESKC                            216
```

```
SEQ ID NO: 102          moltype = AA   length = 222
FEATURE                 Location/Qualifiers
REGION                  1..222
                        note = Synthetic polypeptide
source                  1..222
                        mol_type = protein
                        organism = synthetic construct
SEQUENCE: 102
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DS                      222

SEQ ID NO: 103          moltype = AA   length = 225
FEATURE                 Location/Qualifiers
REGION                  1..225
                        note = Synthetic polypeptide
source                  1..225
                        mol_type = protein
                        organism = synthetic construct
SEQUENCE: 103
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGP                   225

SEQ ID NO: 104          moltype = AA   length = 223
FEATURE                 Location/Qualifiers
REGION                  1..223
                        note = Synthetic polypeptide
source                  1..223
                        mol_type = protein
                        organism = synthetic construct
SEQUENCE: 104
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSK                     223

SEQ ID NO: 105          moltype = AA   length = 226
FEATURE                 Location/Qualifiers
REGION                  1..226
                        note = Synthetic polypeptide
source                  1..226
                        mol_type = protein
                        organism = synthetic construct
SEQUENCE: 105
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPK                  226

SEQ ID NO: 106          moltype = AA   length = 223
FEATURE                 Location/Qualifiers
REGION                  1..223
                        note = Synthetic polypeptide
source                  1..223
                        mol_type = protein
                        organism = synthetic construct
SEQUENCE: 106
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSC                     223

SEQ ID NO: 107          moltype = AA   length = 226
FEATURE                 Location/Qualifiers
REGION                  1..226
                        note = Synthetic polypeptide
source                  1..226
                        mol_type = protein
                        organism = synthetic construct
SEQUENCE: 107
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPC                  226

SEQ ID NO: 108          moltype = AA   length = 224
```

```
FEATURE               Location/Qualifiers
REGION                1..224
                      note = Synthetic polypeptide
source                1..224
                      mol_type = protein
                      organism = synthetic construct
SEQUENCE: 108
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSKC                    224

SEQ ID NO: 109         moltype = AA   length = 227
FEATURE                Location/Qualifiers
REGION                 1..227
                       note = Synthetic polypeptide
source                 1..227
                       mol_type = protein
                       organism = synthetic construct
SEQUENCE: 109
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPKC                 227

SEQ ID NO: 110         moltype = AA   length = 673
FEATURE                Location/Qualifiers
REGION                 1..673
                       note = Mutated and Conjugated Protein
REGION                 459..672
                       note = MISC_FEATURE - Light Chain
source                 1..673
                       mol_type = protein
                       organism = synthetic construct
SEQUENCE: 110
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFDAQGQY PDTLLRIYRD NTTISSTSLS ISLYLYTTSI VMTQTPTSLL VSAGDRVTIT   480
CKASQSVSND VAWYQQKPGQ SPKLLISYTS SRYAGVPDRF SGSGYGTDFT LTISSVQAED   540
AAVYFCQQDY NSPPTFGGGT KLEIKRADAA PTVSIFPPSS EQLTSGGASV VCFLNNFYPK   600
DINVKWKIDG SERQNGVLNS WTDQDSKDST YSMSSTLTLT KDEYERHNSY TCEATHKTST   660
SPIVKSFNRN ESK                                                     673

SEQ ID NO: 111         moltype = AA   length = 459
FEATURE                Location/Qualifiers
REGION                 1..459
                       note = Synthetic polypeptide
source                 1..459
                       mol_type = protein
                       organism = synthetic construct
SEQUENCE: 111
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFDAQGQY PDTLLRIYRD NTTISSTSLS ISLYLYTTK                         459

SEQ ID NO: 112         moltype = AA   length = 673
FEATURE                Location/Qualifiers
REGION                 1..673
                       note = Mutated and Conjugated Protein
REGION                 459..672
                       note = MISC_FEATURE - Light Chain
source                 1..673
                       mol_type = protein
                       organism = synthetic construct
SEQUENCE: 112
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
```

```
SELQGTALGN LKQIYYYNSK AITSSEKSAD QFLTNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ    360
TTVPIDKVKT SKKEVTVQEL DLQARHYLHG KFGLYNSDSF GGKVQRGLIV FHSSEGSTVS    420
YDLFDAQGQY PDTLLRIYRD NTTISSTSLS ISLYLYTTSI VMTQTPTSLL VSAGDRVTIT    480
CKASQSVSND VAWYQQKPGQ SPKLLISYTS SRYAGVPDRF SGSGYGTDFT LTISSVQAED    540
AAVYFCQQDY NSPPTFGGGT KLEIKRADAA PTVSIFPPSS EQLTSGGASV VCFLNNFYPK    600
DINVKWKIDG SERQNGVLNS WTDQDSKDST YSMSSTLTLT KDEYERHNSY TCEATHKTST    660
SPIVKSFNRN ESC                                                      673

SEQ ID NO: 113           moltype = AA  length = 459
FEATURE                  Location/Qualifiers
REGION                   1..459
                         note = Synthetic polypeptide
source                   1..459
                         mol_type = protein
                         organism = synthetic construct
SEQUENCE: 113
EVQLQQSGPD LVKPGASVKI SCKASGYSFT GYYMHWVKQS PGKGLEWIGR INPNNGVTLY     60
NQKFKDKATL TVDKSSTTAY MELRSLTSED SAVYYCARST MITNYVMDYW GQGTSVTVSS    120
AKTTPPSVYP LAPGSAAQTN SMVTLGCLVK GYFPEPVTVT WNSGSLSSGV HTFPAVLQSD    180
LYTLSSSVTV PSSTWPSETV TCNVAHPASS TKVDKKIVPR DSGGPSEKSE EINEKDLRKK    240
SELQGTALGN LKQIYYYNSK AITSSEKSAD QFLTNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ    360
TTVPIDKVKT SKKEVTVQEL DLQARHYLHG KFGLYNSDSF GGKVQRGLIV FHSSEGSTVS    420
YDLFDAQGQY PDTLLRIYRD NTTISSTSLS ISLYLYTTC                           459

SEQ ID NO: 114           moltype = AA  length = 674
FEATURE                  Location/Qualifiers
REGION                   1..674
                         note = Mutated and Conjugated Protein
REGION                   459..672
                         note = MISC_FEATURE - Light Chain
source                   1..674
                         mol_type = protein
                         organism = synthetic construct
SEQUENCE: 114
EVQLQQSGPD LVKPGASVKI SCKASGYSFT GYYMHWVKQS PGKGLEWIGR INPNNGVTLY     60
NQKFKDKATL TVDKSSTTAY MELRSLTSED SAVYYCARST MITNYVMDYW GQGTSVTVSS    120
AKTTPPSVYP LAPGSAAQTN SMVTLGCLVK GYFPEPVTVT WNSGSLSSGV HTFPAVLQSD    180
LYTLSSSVTV PSSTWPSETV TCNVAHPASS TKVDKKIVPR DSGGPSEKSE EINEKDLRKK    240
SELQGTALGN LKQIYYYNSK AITSSEKSAD QFLTNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ    360
TTVPIDKVKT SKKEVTVQEL DLQARHYLHG KFGLYNSDSF GGKVQRGLIV FHSSEGSTVS    420
YDLFDAQGQY PDTLLRIYRD NTTISSTSLS ISLYLYTTSI VMTQTPTSLL VSAGDRVTIT    480
CKASQSVSND VAWYQQKPGQ SPKLLISYTS SRYAGVPDRF SGSGYGTDFT LTISSVQAED    540
AAVYFCQQDY NSPPTFGGGT KLEIKRADAA PTVSIFPPSS EQLTSGGASV VCFLNNFYPK    600
DINVKWKIDG SERQNGVLNS WTDQDSKDST YSMSSTLTLT KDEYERHNSY TCEATHKTST    660
SPIVKSFNRN ESKC                                                     674

SEQ ID NO: 115           moltype = AA  length = 460
FEATURE                  Location/Qualifiers
REGION                   1..460
                         note = Synthetic polypeptide
source                   1..460
                         mol_type = protein
                         organism = synthetic construct
SEQUENCE: 115
EVQLQQSGPD LVKPGASVKI SCKASGYSFT GYYMHWVKQS PGKGLEWIGR INPNNGVTLY     60
NQKFKDKATL TVDKSSTTAY MELRSLTSED SAVYYCARST MITNYVMDYW GQGTSVTVSS    120
AKTTPPSVYP LAPGSAAQTN SMVTLGCLVK GYFPEPVTVT WNSGSLSSGV HTFPAVLQSD    180
LYTLSSSVTV PSSTWPSETV TCNVAHPASS TKVDKKIVPR DSGGPSEKSE EINEKDLRKK    240
SELQGTALGN LKQIYYYNSK AITSSEKSAD QFLTNTLLFK GFFTGHPWYN DLLVDLGSTA    300
ATSEYEGSSV DLYGAYYGYQ CAGGTPNKTA CMYGGVTLHD NNRLTEEKKV PINLWIDGKQ    360
TTVPIDKVKT SKKEVTVQEL DLQARHYLHG KFGLYNSDSF GGKVQRGLIV FHSSEGSTVS    420
YDLFDAQGQY PDTLLRIYRD NTTISSTSLS ISLYLYTTKC                          460

SEQ ID NO: 116           moltype = AA  length = 5
FEATURE                  Location/Qualifiers
source                   1..5
                         mol_type = protein
                         organism = synthetic construct
SEQUENCE: 116
GYYMH                                                                  5

SEQ ID NO: 117           moltype = AA  length = 17
FEATURE                  Location/Qualifiers
source                   1..17
                         mol_type = protein
                         organism = synthetic construct
```

```
SEQUENCE: 117
RINPNNGVTL YNQKFKD                                                    17

SEQ ID NO: 118           moltype = AA  length = 11
FEATURE                  Location/Qualifiers
source                   1..11
                         mol_type = protein
                         organism = synthetic construct
SEQUENCE: 118
STMITNYVMD Y                                                          11

SEQ ID NO: 119           moltype = AA  length = 11
FEATURE                  Location/Qualifiers
source                   1..11
                         mol_type = protein
                         organism = synthetic construct
SEQUENCE: 119
KASQSVSNDV A                                                          11

SEQ ID NO: 120           moltype = AA  length = 7
FEATURE                  Location/Qualifiers
source                   1..7
                         mol_type = protein
                         organism = synthetic construct
SEQUENCE: 120
YTSSRYA                                                               7

SEQ ID NO: 121           moltype = AA  length = 9
FEATURE                  Location/Qualifiers
source                   1..9
                         mol_type = protein
                         organism = synthetic construct
SEQUENCE: 121
QQDYNSPPT                                                             9

SEQ ID NO: 122           moltype = AA  length = 29
FEATURE                  Location/Qualifiers
source                   1..29
                         mol_type = protein
                         organism = synthetic construct
SEQUENCE: 122
KISGGGGSGG GGSGGGGSGG GGSGGGGSS                                       29

SEQ ID NO: 123           moltype = AA  length = 21
FEATURE                  Location/Qualifiers
source                   1..21
                         mol_type = protein
                         organism = synthetic construct
SEQUENCE: 123
SPNSASHSGS APQTSSAPGS Q                                               21

SEQ ID NO: 124           moltype = AA  length = 452
FEATURE                  Location/Qualifiers
source                   1..452
                         mol_type = protein
                         organism = synthetic construct
SEQUENCE: 124
EVQLLESGGG LVQPGGSLRL SCAVSGFTFN SFAMSWVRQA PGKGLEWVSA ISGSGGGTYY     60
ADSVKGRFTI SRDNSKNTLY LQMNSLRAED TAVYFCAKDK ILWFGEPVFD YWGQGTLVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 125           moltype = AA  length = 5
FEATURE                  Location/Qualifiers
source                   1..5
                         mol_type = protein
                         organism = synthetic construct
SEQUENCE: 125
SFAMS                                                                 5

SEQ ID NO: 126           moltype = AA  length = 17
FEATURE                  Location/Qualifiers
source                   1..17
                         mol_type = protein
                         organism = synthetic construct
```

```
SEQUENCE: 126
AISGSGGGTY YADSVKG                                                    17

SEQ ID NO: 127         moltype = AA   length = 13
FEATURE                Location/Qualifiers
source                 1..13
                       mol_type = protein
                       organism = synthetic construct
SEQUENCE: 127
DKILWFGEPV FDY                                                        13

SEQ ID NO: 128         moltype = AA   length = 214
FEATURE                Location/Qualifiers
source                 1..214
                       mol_type = protein
                       organism = synthetic construct
SEQUENCE: 128
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPPTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 129         moltype = AA   length = 11
FEATURE                Location/Qualifiers
source                 1..11
                       mol_type = protein
                       organism = synthetic construct
SEQUENCE: 129
RASQSVSSYL A                                                          11

SEQ ID NO: 130         moltype = AA   length = 7
FEATURE                Location/Qualifiers
source                 1..7
                       mol_type = protein
                       organism = synthetic construct
SEQUENCE: 130
DASNRAT                                                                7

SEQ ID NO: 131         moltype = AA   length = 9
FEATURE                Location/Qualifiers
source                 1..9
                       mol_type = protein
                       organism = synthetic construct
SEQUENCE: 131
QQRSNWPPT                                                              9

SEQ ID NO: 132         moltype = AA   length = 449
FEATURE                Location/Qualifiers
source                 1..449
                       mol_type = protein
                       organism = synthetic construct
SEQUENCE: 132
QVQLVQSGAE VAKPGTSVKL SCKASGYTFT DYWMQWVKQR PGQGLEWIGT IYPGDGDTGY      60
AQKFQGKATL TADKSSKTVY MHLSSLASED SAVYYCARGD YYGSNSLDYW GQGTSVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP PCPAPELLGG     240
PSVFLFPPKP KDTLMISRTP EVTCVVVDVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSRDE     360
LIKNQVSLIC LVKGFYPSDI AVEWESNGQP ENNYKTTPPV LDSDGSFFLY SKLTVDKSRW     420
QQGNVFSCSV MHEALHNHYT QKSLSLSPG                                      449

SEQ ID NO: 133         moltype = AA   length = 5
FEATURE                Location/Qualifiers
source                 1..5
                       mol_type = protein
                       organism = synthetic construct
SEQUENCE: 133
DYWMQ                                                                  5

SEQ ID NO: 134         moltype = AA   length = 17
FEATURE                Location/Qualifiers
source                 1..17
                       mol_type = protein
                       organism = synthetic construct
SEQUENCE: 134
TIYPGDGDTG YAQKFQG                                                    17

SEQ ID NO: 135         moltype = AA   length = 11
FEATURE                Location/Qualifiers
```

```
                                -continued source                  1..11
                        mol_type = protein
                        organism = synthetic construct
SEQUENCE: 135
GDYYGSNSLD Y                                                         11

SEQ ID NO: 136          moltype = AA  length = 214
FEATURE                 Location/Qualifiers
source                  1..214
                        mol_type = protein
                        organism = synthetic construct
SEQUENCE: 136
DIVMTQSHLS MSTSLGDPVS ITCKASQDVS TVVAWYQQKP GQSPRRLIYS ASYRYIGVPD    60
RFTGSGAGTD FTFTISSVQA EDLAVYYCQQ HYSPPYTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 137          moltype = AA  length = 11
FEATURE                 Location/Qualifiers
source                  1..11
                        mol_type = protein
                        organism = synthetic construct
SEQUENCE: 137
KASQDVSTVV A                                                         11

SEQ ID NO: 138          moltype = AA  length = 7
FEATURE                 Location/Qualifiers
source                  1..7
                        mol_type = protein
                        organism = synthetic construct
SEQUENCE: 138
SASYRYI                                                               7

SEQ ID NO: 139          moltype = AA  length = 9
FEATURE                 Location/Qualifiers
source                  1..9
                        mol_type = protein
                        organism = synthetic construct
SEQUENCE: 139
QQHYSPPYT                                                             9
```

What is claimed is:

1. A bifunctional chelator compound comprising a formula

R—L$_1$—M wherein R is a reactive group, wherein L$_1$ comprises

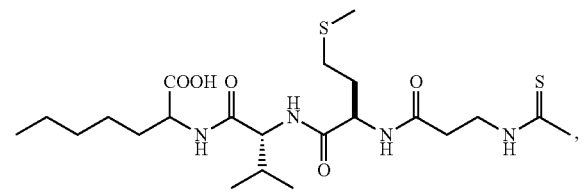 [SMILES: CCCCCC(NC(=O)[C@H](NC(=O)[C@@H](CCSC)NC(=O)CCNC(C)=S)C(C)C)C(=O)O]

and wherein M is a chelator moiety.

2. The bifunctional chelator compound of claim 1, wherein M comprises a formula selected from a group consisting of:

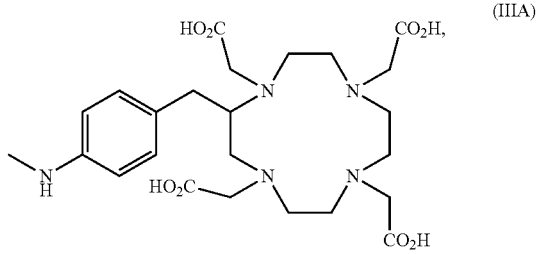 (IIIA)

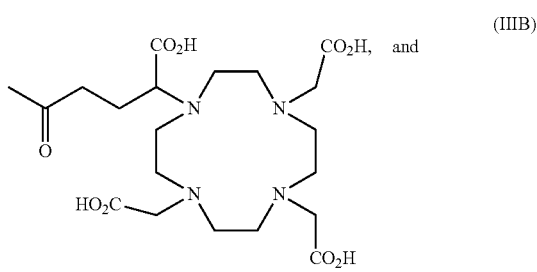 (IIIB)

(IIIC)

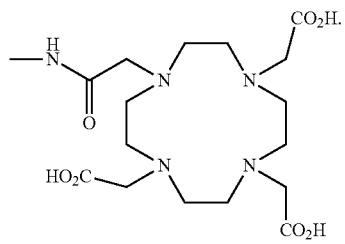

3. The bifunctional chelator compound of claim 1, wherein R comprises a formula selected from a group consisting of:

(IIID)

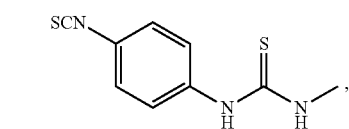

-continued (IIIE)

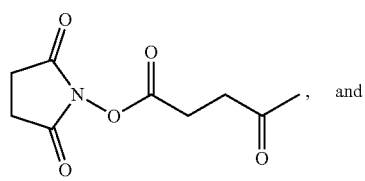

, and (IIIF)

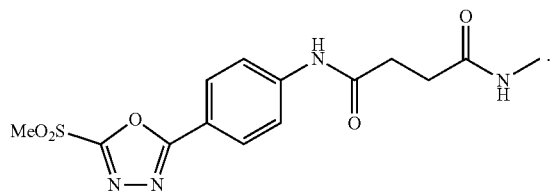

4. The bifunctional chelator of claim 1, further comprising at least one radionuclide, wherein the at least one radionuclide is chelated by the chelator moiety, and wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

5. A conjugate of the bifunctional chelator compound of claim 1 with a molecule comprising a primary amine group or a free thiol group.

6. The conjugate of claim 5, wherein the molecule comprising a primary amine group or a free thiol group is a peptide or a protein.

7. The conjugate of claim 5, wherein the molecule comprising a primary amine group or a free thiol group comprises an antibody, a monoclonal antibody, an antigen-binding fragment of an antibody, an antigen-binding fragment of a monoclonal antibody, an immunoglobulin heavy chain, an immunoglobulin heavy chain variable region, immunoglobulin light chain, an immunoglobulin light chain variable region, a nanobody, a scFv molecule, or an antibody mimetic protein.

8. The bifunctional chelator compound of claim 2, comprising the formula:

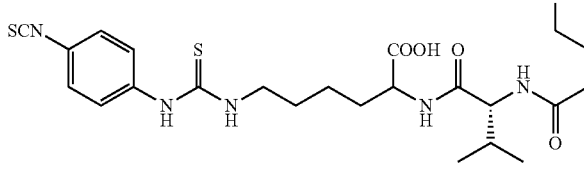
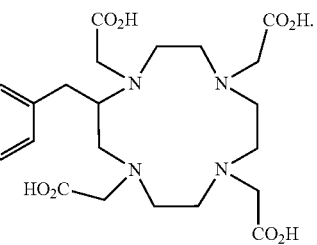

9. A conjugate of the bifunctional chelator compound of claim 8 with a molecule comprising a primary amine group.

10. The conjugate of claim 9, wherein the molecule comprising a primary amine group is a peptide or a protein.

11. The conjugate of claim 9, wherein the molecule comprising a primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

12. The conjugate of claim 9, further comprising a radionuclide chelated by the chelator moiety, wherein the radionuclide is $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{201}$Tl, $^{203}$Pb, $^{212}$Pb, $^{212}$Bi, $^{213}$Bi, $^{225}$Ac, or $^{227}$Th.

13. A method for manufacturing a chelator-conjugated molecule, comprising:
reacting a molecule comprising at least one primary amine group with a bifunctional chelator compound according to claim 1 wherein the reactive group is a N-hydroxysuccinimide ester (NHS) reactive group or an isothiocyanate (SCN) reactive group, to conjugate the bifunctional chelator compound to the molecule; or
reacting a molecule comprising at least one free thiol group with a bifunctional chelator compound according to claim 1 wherein the reactive group is a phenyloxadiazolyl methylsulfone (PODS) reactive group, to conjugate the bifunctional chelator compound to the molecule.

14. A method for manufacturing a chelator-conjugated molecule, comprising: reacting a molecule comprising at least one free thiol group with a bifunctional chelator compound according to claim 1, wherein the reactive group is a phenyloxadiazolyl methylsulfone (PODS) reactive group, to conjugate the bifunctional chelator compound to the molecule; and reducing a disulfide bond to generate the at least one free thiol group of the molecule.

15. The method of claim 13, wherein the molecule comprising at least one primary amine group is a peptide or a protein, and the molecule comprising at least one free thiol group is a peptide or a protein.

16. The method of claim 13, wherein the molecule comprising at least one primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein; and the molecule comprising at least one free thiol group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

17. The method of claim 13, further comprising chelating a radionuclide to the chelator moiety of the bifunctional chelator compound before or after performing the conjugation.

18. A method for manufacturing a chelator-conjugated molecule, comprising: reacting a molecule comprising at least one primary amine group with a bifunctional chelator compound comprising the structure 19. The method of claim 18, wherein the molecule comprising at least one primary amine group is a peptide or a protein.

20. The method of claim 18, wherein the molecule comprising at least one primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

21. The method of claim 18, further comprising:
chelating a radionuclide to the chelator-conjugated molecule.

22. The method of claim 21, wherein the radionuclide is $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{201}$Tl, $^{203}$Pb, $^{212}$Pb, $^{212}$Bi, $^{213}$Bi, $^{225}$Ac, or $^{227}$Th.

23. The bifunctional chelator compound of claim 2, wherein R comprises a formula selected from a group consisting of:

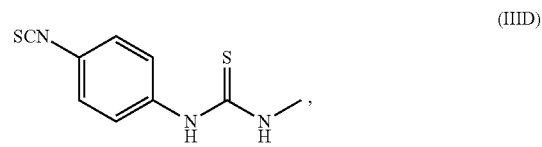

(IIID)

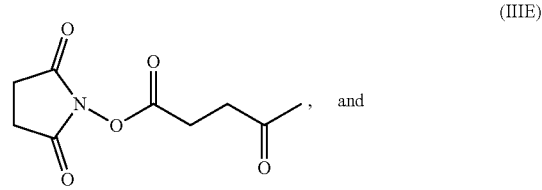

(IIIE)

and

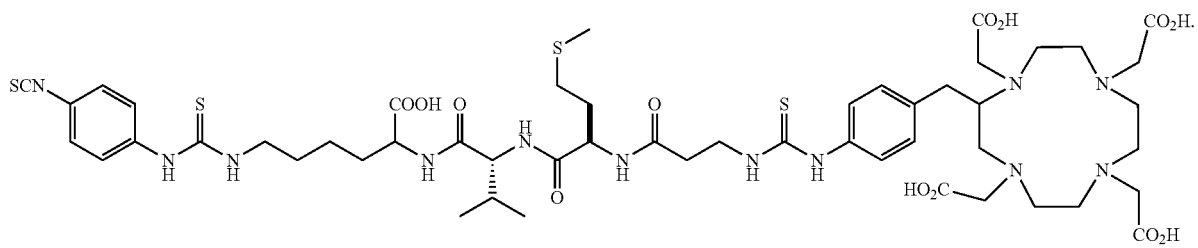

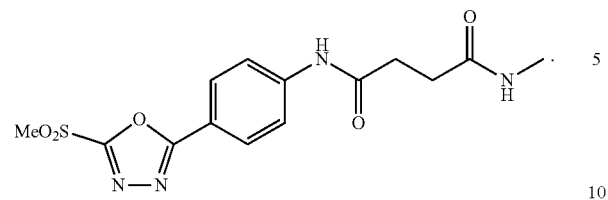
(IIIF)
* * * * *